(12) United States Patent
Newton

(10) Patent No.: US 12,702,579 B2
(45) Date of Patent: Aug. 11, 2026

(54) CONDUITS INCLUDING AT LEAST ONE CONDUIT POROUS MATERIAL

(71) Applicant: PUREWICK CORPORATION, Covington, GA (US)

(72) Inventor: Camille Rose Newton, Bonsall, CA (US)

(73) Assignee: PUREWICK CORPORATION, Covington, GA (US)

( * ) Notice: Subject to any disclaimer, the term of this patent is extended or adjusted under 35 U.S.C. 154(b) by 123 days.

(21) Appl. No.: 18/553,625

(22) PCT Filed: Apr. 6, 2022

(86) PCT No.: PCT/US2022/023594
§ 371 (c)(1),
(2) Date: Oct. 2, 2023

(87) PCT Pub. No.: WO2022/216776
PCT Pub. Date: Oct. 13, 2022

(65) Prior Publication Data

US 2024/0180737 A1 Jun. 6, 2024

Related U.S. Application Data

(60) Provisional application No. 63/172,975, filed on Apr. 9, 2021.

(51) Int. Cl.
*A61F 5/451* (2006.01)
*A61F 5/44* (2006.01)
*A61F 5/455* (2006.01)

(52) U.S. Cl.
CPC ............ *A61F 5/4404* (2013.01); *A61F 5/451* (2013.01); *A61F 5/455* (2013.01)

(58) Field of Classification Search
CPC ......... A61F 5/4404; A61F 5/451; A61F 5/455
See application file for complete search history.

(56) References Cited

U.S. PATENT DOCUMENTS 737,443 A 8/1903 Mooers
976,883 A 11/1910 Keagy et al.
(Continued)

FOREIGN PATENT DOCUMENTS

AU 2018216821 A1 8/2019
AU 2021299304 A1 2/2023
(Continued)

OTHER PUBLICATIONS

US 9,908,683 B2, 03/2018, Sandhausen et al. (withdrawn)
(Continued)

*Primary Examiner* — Guy K Townsend
(74) *Attorney, Agent, or Firm* — Ballard Spahr LLP

(57) ABSTRACT

Embodiments disclosed herein include conduits including at least one conduit porous material, fluid collection assemblies and systems including the same, and methods of using and forming the same. An example conduit includes at least one wall at least partially defining at least an inlet, and outlet downstream from the inlet, and a passageway extending from the inlet to the outlet. The conduit also includes at least one conduit porous material disposed in the passageway. The conduit porous material may at least partially occupy the passageway and may extend along at least a portion of a length of the conduit measured from the inlet to the outlet. The conduit may be configured for use in a fluid collection system for collecting one or more bodily fluids (e.g., urine, amniotic fluid, blood, etc.).

23 Claims, 11 Drawing Sheets

(56) References Cited

U.S. PATENT DOCUMENTS 1,015,905 A 1/1912 Northrop
1,032,841 A 7/1912 Koenig
1,178,644 A 4/1916 Johnson
1,229,423 A 6/1917 Eckenrode
1,387,726 A 8/1921 Karge
1,742,080 A 12/1929 Jones
1,979,899 A 11/1934 Obrien et al.
2,241,010 A 5/1941 Chipley
2,262,772 A 11/1941 Peder
2,326,881 A 8/1943 Packer
2,379,346 A 6/1945 Farrell
2,485,555 A 10/1949 Bester
2,571,357 A 10/1951 Charles
2,613,670 A 10/1952 Edward
2,616,426 A 11/1952 Adele
2,644,234 A 7/1953 Earl
2,648,335 A 8/1953 Chambers
2,789,560 A 4/1957 Weimer
2,859,786 A 11/1958 Tupper
2,944,551 A 7/1960 Carl
2,968,046 A 1/1961 Duke
2,971,512 A 2/1961 Reinhardt
3,032,038 A 5/1962 Swinn
3,077,883 A 2/1963 Hill
3,087,938 A 4/1963 Hans et al.
3,114,916 A 12/1963 Hadley
3,169,528 A 2/1965 Knox et al.
3,171,506 A 3/1965 Therkel
3,175,719 A 3/1965 Herndon
3,194,238 A 7/1965 Breece
3,198,994 A 8/1965 Hildebrandt et al.
3,221,742 A 12/1965 Egon
3,312,221 A 4/1967 Overment
3,312,981 A 4/1967 Mcguire et al.
3,349,768 A 10/1967 Keane
3,356,091 A 12/1967 Patterson
3,362,590 A 1/1968 Gene
3,366,116 A 1/1968 Huck
3,368,564 A 2/1968 Selix
3,369,940 A 2/1968 Slautterback
3,398,848 A 8/1968 Donovan
3,400,717 A 9/1968 Bruce et al.
3,406,688 A 10/1968 Bruce
3,411,504 A 11/1968 Glassman
3,424,163 A 1/1969 Gravdahl
3,425,471 A 2/1969 Yates
3,434,565 A 3/1969 Fischer
3,447,536 A 6/1969 Snyder
3,511,241 A 5/1970 Lee
3,512,185 A 5/1970 Ellis
3,520,300 A 7/1970 Flower
3,528,423 A 9/1970 Lee
3,608,552 A 9/1971 Broerman
3,613,123 A 10/1971 Langstrom
3,648,700 A 3/1972 Warner
3,651,810 A 3/1972 Ormerod
3,661,155 A 5/1972 Lindan
3,683,918 A 8/1972 Pizzella
3,699,815 A 10/1972 Holbrook
3,720,554 A 3/1973 Stumpf
3,721,243 A 3/1973 Greth et al.
3,726,277 A 4/1973 Hirschman
3,727,788 A 4/1973 Holbrook
3,730,411 A 5/1973 Brockmuller
3,742,952 A 7/1973 Magers et al.
3,742,953 A 7/1973 Lee
3,757,355 A 9/1973 Allen et al.
3,788,324 A 1/1974 Lim
3,843,016 A 10/1974 Bornhorst et al.
3,863,638 A 2/1975 Rogers et al.
3,863,798 A 2/1975 Kurihara et al.
3,864,759 A 2/1975 Horiuchi
3,865,109 A 2/1975 Elmore et al.
3,881,486 A 5/1975 Fenton
3,881,489 A 5/1975 Hartwell
3,915,189 A 10/1975 Holbrook et al.
3,931,650 A 1/1976 Miller
3,931,819 A 1/1976 Weedle
3,964,786 A 6/1976 Mashuda
3,998,228 A 12/1976 Poidomani
3,999,550 A 12/1976 Martin
4,006,793 A 2/1977 Robinson
4,015,604 A 4/1977 Csillag
4,020,843 A 5/1977 Kanall
4,022,211 A 5/1977 Timmons et al.
4,022,213 A 5/1977 Stein
4,023,216 A 5/1977 Li
4,027,776 A 6/1977 Douglas
4,031,897 A 6/1977 Graetz
4,042,337 A 8/1977 Griffith
4,064,962 A 12/1977 Hunt
4,069,817 A 1/1978 Fenole et al.
4,084,589 A 4/1978 Kulvi
4,096,897 A 6/1978 Cammarata
4,116,197 A 9/1978 Bermingham
4,140,739 A 2/1979 Cotten
4,180,178 A 12/1979 Turner
4,187,953 A 2/1980 Turner
4,194,508 A 3/1980 Anderson
4,197,849 A 4/1980 Bostick
4,200,102 A 4/1980 Duhamel et al.
4,202,058 A 5/1980 Anderson
4,203,503 A 5/1980 Bertotti et al.
4,209,076 A 6/1980 Bertotti et al.
D255,935 S 7/1980 Cullis et al.
4,223,677 A 9/1980 Anderson
4,233,025 A 11/1980 Larson et al.
4,233,978 A 11/1980 Hickey
4,246,901 A 1/1981 Frosch et al.
4,253,542 A 3/1981 Ruspa et al.
4,257,418 A 3/1981 Hessner
4,270,539 A 6/1981 Frosch et al.
4,280,498 A 7/1981 Jensen
4,281,655 A 8/1981 Terauchi
4,292,916 A 10/1981 Bradley et al.
4,330,239 A 5/1982 Gannaway
4,345,341 A 8/1982 Saito
4,349,029 A 9/1982 Mott
4,352,356 A 10/1982 Tong
4,356,012 A 10/1982 Hofstetter
4,360,933 A 11/1982 Kimura et al.
4,365,363 A 12/1982 Windauer
4,372,299 A 2/1983 Fixel
4,375,841 A 3/1983 Vielbig
4,387,726 A 6/1983 Denard
4,403,991 A 9/1983 Hill
4,421,511 A 12/1983 Steer et al.
4,425,130 A 1/1984 Desmarais
4,446,986 A 5/1984 Bowen et al.
4,453,938 A 6/1984 Brendling
4,457,314 A 7/1984 Knowles
4,457,758 A 7/1984 Norton
4,476,879 A 10/1984 Jackson
4,512,771 A 4/1985 Norton
4,526,688 A 7/1985 Schmidt et al.
4,528,703 A 7/1985 Kraus
4,533,354 A 8/1985 Jensen
4,533,357 A 8/1985 Hall
D280,438 S 9/1985 Wendt
4,551,141 A 11/1985 Mcneil
4,553,968 A 11/1985 Komis
4,568,341 A 2/1986 Mitchell et al.
4,581,026 A 4/1986 Schneider
4,583,983 A 4/1986 Einhorn et al.
4,589,516 A 5/1986 Inoue et al.
4,601,716 A 7/1986 Smith
4,610,675 A 9/1986 Triunfol
4,620,333 A 11/1986 Ritter
4,626,250 A 12/1986 Schneider
4,627,846 A 12/1986 Ternstroem
4,631,061 A 12/1986 Martin
4,645,275 A 2/1987 Pucci
4,650,477 A 3/1987 Johnson
4,655,754 A 4/1987 Richmond et al.

(56) References Cited

U.S. PATENT DOCUMENTS 4,656,675 A 4/1987 Fajnsztajn
4,681,570 A 7/1987 Dalton
4,681,572 A 7/1987 Tokarz et al.
4,681,577 A 7/1987 Stern et al.
4,692,160 A 9/1987 Nussbaumer
4,707,864 A 11/1987 Ikematsu et al.
4,713,065 A 12/1987 Koot
4,713,066 A 12/1987 Komis
4,723,953 A 2/1988 Pratt et al.
4,735,841 A 4/1988 Sourdet
4,743,236 A 5/1988 Manschot
4,747,166 A 5/1988 Kuntz
4,752,944 A 6/1988 Conrads et al.
4,759,753 A 7/1988 Schneider et al.
4,769,215 A 9/1988 Ehrenkranz
4,771,484 A 9/1988 Mozell
4,772,280 A 9/1988 Rooyakkers
4,775,458 A 10/1988 Forester
4,784,654 A 11/1988 Beecher
4,790,830 A 12/1988 Hamacher
4,790,835 A 12/1988 Elias
4,791,686 A 12/1988 Taniguchi et al.
4,795,449 A 1/1989 Schneider et al.
4,798,603 A 1/1989 Meyer et al.
4,799,928 A 1/1989 Crowley
4,804,377 A 2/1989 Hanifl et al.
4,812,053 A 3/1989 Bhattacharjee
4,813,943 A 3/1989 Smith
4,820,291 A 4/1989 Terauchi et al.
4,820,297 A 4/1989 Kaufman et al.
4,841,728 A 6/1989 Jean et al.
4,846,818 A 7/1989 Keldahl et al.
4,846,819 A 7/1989 Welch
4,846,824 A 7/1989 Lassen et al.
4,846,909 A 7/1989 Klug et al.
4,857,064 A 8/1989 Mendoza
4,865,595 A 9/1989 Heyden
4,872,299 A 10/1989 Troutner et al.
4,875,898 A 10/1989 Eakin
4,880,417 A 11/1989 Yabrov et al.
4,882,794 A 11/1989 Stewart
4,883,465 A 11/1989 Brennan
4,886,498 A 12/1989 Newton
4,886,508 A 12/1989 Washington
4,886,509 A 12/1989 Mattsson
4,889,532 A 12/1989 Metz et al.
4,889,533 A 12/1989 Beecher
4,890,691 A 1/1990 Ching-ho
4,895,140 A 1/1990 Bellak
4,903,254 A 2/1990 Haas
4,904,248 A 2/1990 Vaillancourt
D306,759 S 3/1990 D'Alo
4,905,692 A 3/1990 More
4,911,262 A 3/1990 Tani et al.
4,930,997 A 6/1990 Bennett
4,936,838 A 6/1990 Cross et al.
4,950,262 A 8/1990 Takagi
4,955,922 A 9/1990 Terauchi
4,957,487 A 9/1990 Gerow
4,965,460 A 10/1990 Tanaka et al.
4,986,823 A 1/1991 Anderson et al.
4,987,849 A 1/1991 Sherman
5,002,541 A 3/1991 Conkling et al.
5,004,463 A 4/1991 Nigay
5,013,308 A 5/1991 Sullivan et al.
5,030,229 A 7/1991 Yang
5,031,248 A 7/1991 Kemper
5,045,077 A 9/1991 Blake
5,045,283 A 9/1991 Patel
5,049,144 A 9/1991 Payton
5,053,339 A 10/1991 Patel
5,057,092 A 10/1991 Webster
5,058,088 A 10/1991 Haas et al.
5,071,347 A 12/1991 Mcguire
5,078,707 A 1/1992 Peter
5,084,037 A 1/1992 Barnett
5,100,396 A 3/1992 Zamierowski
5,102,404 A 4/1992 Goldberg et al.
5,112,324 A 5/1992 Wallace
5,134,994 A 8/1992 Say
5,137,033 A 8/1992 Norton
5,147,301 A 9/1992 Ruvio
5,176,667 A 1/1993 Debring
5,195,997 A 3/1993 Carns
5,196,654 A 3/1993 Diflora et al.
5,199,444 A 4/1993 Wheeler
5,203,699 A 4/1993 Mcguire
5,234,419 A 8/1993 Bryant et al.
5,244,458 A 9/1993 Takasu
5,246,454 A 9/1993 Peterson
5,267,988 A 12/1993 Farkas
5,275,307 A 1/1994 Freese
5,282,795 A 2/1994 Finney
5,295,979 A 3/1994 DeLaurentis et al.
5,295,983 A 3/1994 Kubo
5,300,052 A 4/1994 Kubo
5,304,749 A 4/1994 Crandell
5,312,383 A 5/1994 Kubalak
5,318,550 A 6/1994 Cermak et al.
5,330,457 A 7/1994 Cohen
5,330,459 A 7/1994 Lavon et al.
5,334,174 A 8/1994 Street
5,334,176 A 8/1994 Buenger et al.
5,340,840 A 8/1994 Park et al.
D354,129 S 1/1995 Salvadori
D354,560 S 1/1995 Chase
5,382,244 A 1/1995 Telang
5,397,315 A 3/1995 Schmidt et al.
5,409,014 A 4/1995 Napoli et al.
5,409,475 A 4/1995 Steer
5,411,495 A 5/1995 Willingham
5,423,784 A 6/1995 Metz
5,423,788 A 6/1995 Rollins et al.
5,437,836 A 8/1995 Yamada
5,455,091 A 10/1995 Oreglia et al.
5,456,246 A 10/1995 Schmieding et al.
5,466,229 A 11/1995 Elson et al.
5,478,334 A 12/1995 Bernstein
5,499,977 A 3/1996 Marx
5,525,407 A 6/1996 Yang
5,543,042 A 8/1996 Filan et al.
D373,928 S 9/1996 Green
5,582,604 A 12/1996 Ahr et al.
5,592,950 A 1/1997 Kopelowicz
5,593,389 A 1/1997 Chang
5,605,161 A 2/1997 Cross
5,614,699 A 3/1997 Yashiro et al.
5,618,277 A 4/1997 Goulter
5,628,735 A 5/1997 Skow
5,632,736 A 5/1997 Block
5,636,643 A 6/1997 Argenta et al.
5,637,104 A 6/1997 Ball et al.
5,641,277 A 6/1997 Gondek
D380,543 S 7/1997 Piontek et al.
5,662,633 A 9/1997 Doak et al.
5,674,212 A 10/1997 Osborn et al.
5,678,564 A 10/1997 Lawrence et al.
5,681,297 A 10/1997 Hashimoto et al.
5,687,429 A 11/1997 Rahlff
5,695,485 A 12/1997 Duperret et al.
5,695,487 A 12/1997 Cohen et al.
5,700,254 A 12/1997 Mcdowall et al.
5,701,612 A 12/1997 Daneshvar
5,705,777 A 1/1998 Flanigan et al.
5,735,835 A 4/1998 Holland
5,735,837 A 4/1998 Ishikawa
5,752,944 A 5/1998 Dann et al.
5,763,333 A 6/1998 Suzuki et al.
5,772,644 A 6/1998 Bark et al.
5,792,132 A 8/1998 Garcia
5,827,243 A 10/1998 Palestrant
5,827,247 A 10/1998 Kay
5,827,250 A 10/1998 Fujioka et al.
5,827,257 A 10/1998 Fujioka et al.

(56) References Cited

U.S. PATENT DOCUMENTS

D401,699 S 11/1998 Herchenbach et al.
5,859,393 A 1/1999 Cummins et al.
5,865,378 A 2/1999 Hollinshead et al.
5,873,869 A 2/1999 Hammons et al.
5,876,393 A 3/1999 Ahr et al.
5,887,291 A 3/1999 Bellizzi
5,891,125 A 4/1999 Plumley
5,894,608 A 4/1999 Birbara
5,895,349 A 4/1999 Tihon
D409,303 S 5/1999 Oepping
5,911,222 A 6/1999 Lawrence et al.
5,956,782 A 9/1999 Olguin
5,957,904 A 9/1999 Holland
5,968,026 A 10/1999 Osborn et al.
5,972,505 A 10/1999 Phillips et al.
6,007,524 A 12/1999 Schneider
6,007,526 A 12/1999 Passalaqua et al.
D421,307 S 2/2000 Harmanoglu
6,039,060 A 3/2000 Rower
6,050,983 A 4/2000 Moore et al.
6,059,762 A 5/2000 Boyer et al.
6,061,905 A 5/2000 Logic
6,063,064 A 5/2000 Tuckey et al.
6,083,602 A 7/2000 Caldwell et al.
6,098,625 A 8/2000 Winkler
6,105,174 A 8/2000 Karlsten et al.
6,113,582 A 9/2000 Dwork
6,117,163 A 9/2000 Bierman
6,123,398 A 9/2000 Arai et al.
6,129,718 A 10/2000 Wada et al.
6,131,964 A 10/2000 Sareshwala
6,152,902 A 11/2000 Christian et al.
6,164,569 A 12/2000 Hollinshead et al.
6,177,606 B1 1/2001 Etheredge et al.
6,209,142 B1 4/2001 Mattsson et al.
6,220,050 B1 4/2001 Cooksey
6,244,311 B1 6/2001 Hand et al.
6,248,096 B1 6/2001 Dwork et al.
6,263,887 B1 7/2001 Dunn
6,283,246 B1 9/2001 Nishikawa
6,296,627 B1 10/2001 Edwards
6,311,339 B1 11/2001 Kraus
6,316,688 B1 11/2001 Hammons et al.
6,336,919 B1 1/2002 Davis et al.
6,338,729 B1 1/2002 Wada et al.
6,352,525 B1 3/2002 Wakabayashi
6,394,988 B1 5/2002 Hashimoto
6,395,956 B1 5/2002 Glasgow et al.
6,398,742 B1 6/2002 Kim
6,406,463 B1 6/2002 Brown
6,409,712 B1 6/2002 Dutari et al.
6,415,888 B2 7/2002 An et al.
6,416,500 B1 7/2002 Wada et al.
6,417,750 B1 7/2002 Sohn
6,423,045 B1 7/2002 Wise et al.
6,428,521 B1 8/2002 Droll
6,428,522 B1 8/2002 Dipalma et al.
6,446,454 B1 9/2002 Lee et al.
6,461,340 B1 10/2002 Lenker et al.
6,467,570 B1 10/2002 Herold
6,475,198 B1 11/2002 Lipman et al.
6,479,726 B1 11/2002 Cole et al.
6,491,673 B1 12/2002 Palumbo et al.
6,508,794 B1 1/2003 Palumbo et al.
6,524,292 B1 2/2003 Dipalma et al.
6,526,603 B1 3/2003 Murphy
6,540,729 B1 4/2003 Wada et al.
6,547,771 B2 4/2003 Robertson et al.
6,551,293 B1 4/2003 Mitchell
6,569,133 B2 5/2003 Cheng et al.
D476,518 S 7/2003 Doppelt
6,592,560 B2 7/2003 Snyder et al.
6,610,038 B1 8/2003 Dipalma et al.
6,618,868 B2 9/2003 Minnick
6,620,142 B1 9/2003 Flueckiger
6,629,651 B1 10/2003 Male et al.
6,635,037 B1 10/2003 Bennett
6,635,038 B2 10/2003 Scovel
6,652,495 B1 11/2003 Walker
6,666,850 B1 12/2003 Ahr et al.
6,685,684 B1 2/2004 Falconer
6,695,828 B1 2/2004 Dipalma et al.
6,699,174 B1 3/2004 Bennett
6,700,034 B1 3/2004 Lindsay et al.
6,702,793 B1 3/2004 Sweetser et al.
6,706,027 B2 3/2004 Harvie et al.
6,732,384 B2 5/2004 Scott
6,736,977 B1 5/2004 Hall et al.
6,740,066 B2 5/2004 Wolff et al.
6,764,477 B1 7/2004 Chen et al.
6,783,519 B2 8/2004 Samuelsson
6,796,974 B2 9/2004 Palumbo et al.
6,814,547 B2 11/2004 Childers et al.
6,848,719 B2 2/2005 Rowley
6,849,065 B2 2/2005 Schmidt et al.
6,857,137 B2 2/2005 Otto
6,878,647 B1 4/2005 Rezai et al.
6,885,690 B2 4/2005 Aggerstam et al.
6,888,044 B2 5/2005 Fell et al.
6,893,425 B2 5/2005 Dunn et al.
6,912,737 B2 7/2005 Ernest et al.
6,918,899 B2 7/2005 Harvie
6,979,324 B2 12/2005 Bybordi et al.
7,018,366 B2 3/2006 Easter
7,066,411 B2 6/2006 Male et al.
7,087,043 B2 8/2006 Dolan
7,122,023 B1 10/2006 Hinoki
7,125,399 B2 10/2006 Miskie
7,131,964 B2 11/2006 Harvie
7,135,012 B2 11/2006 Harvie
7,141,043 B2 11/2006 Harvie
D533,972 S 12/2006 La
7,160,273 B2 1/2007 Greter et al.
7,166,092 B2 1/2007 Elson et al.
7,171,699 B2 2/2007 Ernest et al.
7,171,871 B2 2/2007 Kozak
7,179,951 B2 2/2007 Krishnaswamy-mirle et al.
7,181,781 B1 2/2007 Trabold et al.
7,186,245 B1 3/2007 Cheng et al.
7,192,424 B2 3/2007 Cooper
7,219,764 B1 5/2007 Forbes
7,220,250 B2 5/2007 Suzuki et al.
D562,975 S 2/2008 Otto
7,335,189 B2 2/2008 Harvie
7,358,282 B2 4/2008 Krueger et al.
7,390,320 B2 6/2008 Machida et al.
7,438,706 B2 10/2008 Koizumi et al.
7,488,310 B2 2/2009 Yang
7,491,194 B1 2/2009 Oliwa
D591,106 S 4/2009 Dominique et al.
7,513,381 B2 4/2009 Heng et al.
7,520,872 B2 4/2009 Biggie et al.
D593,801 S 6/2009 Wilson et al.
7,540,364 B2 6/2009 Sanderson
7,549,511 B2 6/2009 Marocco
7,549,512 B2 6/2009 Newberry
7,585,293 B2 9/2009 Vermaak
7,588,560 B1 9/2009 Dunlop
7,637,905 B2 12/2009 Saadat et al.
7,658,730 B2 2/2010 Conley
7,665,359 B2 2/2010 Barber
7,682,347 B2 3/2010 Parks et al.
7,687,004 B2 3/2010 Allen
7,695,459 B2 4/2010 Gilbert et al.
7,695,460 B2 4/2010 Wada et al.
7,699,818 B2 4/2010 Gilbert
7,699,831 B2 4/2010 Bengtson et al.
7,722,584 B2 5/2010 Tanaka et al.
7,727,206 B2 6/2010 Gorres
7,740,620 B2 6/2010 Gilbert et al.
7,749,205 B2 7/2010 Tazoe et al.
7,755,497 B2 7/2010 Wada et al.
7,766,887 B2 8/2010 Burns et al.
7,803,144 B1 9/2010 Vollrath

(56) References Cited

U.S. PATENT DOCUMENTS

D625,407 S 10/2010 Koizumi et al.
7,806,879 B2 10/2010 Brooks et al.
7,811,272 B2 10/2010 Lindsay et al.
7,815,067 B2 10/2010 Matsumoto et al.
7,833,169 B2 11/2010 Hannon
7,857,806 B2 12/2010 Karpowicz et al.
7,866,942 B2 1/2011 Harvie
7,871,385 B2 1/2011 Levinson et al.
7,875,010 B2 1/2011 Frazier et al.
7,901,389 B2 3/2011 Mombrinie
7,927,320 B2 4/2011 Goldwasser et al.
7,927,321 B2 4/2011 Marland
7,931,634 B2 4/2011 Swiecicki et al.
7,939,706 B2 5/2011 Okabe et al.
7,946,443 B2 5/2011 Stull et al.
7,947,025 B2 5/2011 Buglino et al.
7,963,419 B2 6/2011 Burney et al.
7,976,519 B2 7/2011 Bubb et al.
7,981,087 B2 7/2011 Gesler, III
7,993,318 B2 8/2011 Olsson et al.
8,015,627 B2 9/2011 Baker et al.
8,016,071 B1 9/2011 Martinus et al.
8,028,460 B2 10/2011 Williams
8,047,398 B2 11/2011 Dimartino et al.
8,083,094 B2 12/2011 Caulfield et al.
8,128,608 B2 3/2012 Thevenin
8,156,941 B1 4/2012 Simms
8,167,860 B1 5/2012 Siegel
8,181,651 B2 5/2012 Pinel
8,181,819 B2 5/2012 Burney et al.
8,211,063 B2 7/2012 Bierman et al.
8,221,369 B2 7/2012 Parks et al.
8,241,262 B2 8/2012 Mahnensmith
8,277,426 B2 10/2012 Wilcox et al.
8,287,508 B1 10/2012 Sanchez
8,303,554 B2 11/2012 Tsai et al.
8,322,565 B2 12/2012 Caulfield et al.
8,337,477 B2 12/2012 Parks et al.
D674,241 S 1/2013 Bickert et al.
8,343,122 B2 1/2013 Gorres
8,343,125 B2 1/2013 Kawazoe et al.
8,353,074 B2 1/2013 Krebs
8,353,886 B2 1/2013 Bester et al.
D676,241 S 2/2013 Merrill
8,388,587 B1 3/2013 Gmuer et al.
8,388,588 B2 3/2013 Wada et al.
D679,807 S 4/2013 Burgess et al.
8,425,482 B2 4/2013 Khoubnazar
8,434,586 B2 5/2013 Pawelski et al.
8,449,510 B2 5/2013 Martini et al.
D684,260 S 6/2013 Lund et al.
8,470,230 B2 6/2013 Caulfield et al.
8,479,941 B2 7/2013 Matsumoto et al.
8,479,949 B2 7/2013 Henkel
8,500,719 B1 8/2013 Simpson et al.
8,512,301 B2 8/2013 Ma
8,529,530 B2 9/2013 Koch et al.
8,535,284 B2 9/2013 Joder et al.
8,546,639 B2 10/2013 Wada et al.
8,551,062 B2 10/2013 Kay
8,551,075 B2 10/2013 Bengtson
8,568,376 B2 10/2013 Delattre et al.
D694,404 S 11/2013 Burgess et al.
8,585,683 B2 11/2013 Bengtson et al.
8,652,112 B2 2/2014 Johannison et al.
8,669,412 B2 3/2014 Fernkvist et al.
D702,973 S 4/2014 Norland et al.
8,702,667 B1 4/2014 Johnson
8,703,032 B2 4/2014 Menon et al.
D704,330 S 5/2014 Cicatelli
D704,510 S 5/2014 Mason et al.
D705,423 S 5/2014 Walsh Cutler
D705,926 S 5/2014 Burgess et al.
8,714,394 B2 5/2014 Wulf
8,715,267 B2 5/2014 Bengtson et al.
8,740,852 B2 6/2014 Aviles
8,757,425 B2 6/2014 Copeland
8,777,032 B2 7/2014 Biesecker et al.
8,808,260 B2 8/2014 Koch et al.
8,864,730 B2 10/2014 Conway et al.
8,881,923 B2 11/2014 Higginson
8,882,731 B2 11/2014 Suzuki et al.
8,936,585 B2 1/2015 Carson et al.
D729,581 S 5/2015 Boroski
9,028,460 B2 5/2015 Medeiros
9,056,698 B2 6/2015 Noer
9,078,792 B2 7/2015 Ruiz
9,145,879 B2 9/2015 Pirovano et al.
9,173,602 B2 11/2015 Gilbert
9,173,799 B2 11/2015 Tanimoto et al.
9,187,220 B2 11/2015 Biesecker et al.
9,199,772 B2 12/2015 Krippendorf
9,233,020 B2 1/2016 Matsumiya
9,248,058 B2 2/2016 Conway et al.
9,308,118 B1 4/2016 Dupree et al.
9,309,029 B2 4/2016 Incorvia et al.
9,333,281 B2 5/2016 Giezendanner et al.
9,381,108 B2 7/2016 Longoni et al.
9,382,047 B2 7/2016 Schmidtner et al.
9,402,424 B2 8/2016 Roy
9,415,191 B2 8/2016 Aviles
9,456,937 B2 10/2016 Ellis
9,480,595 B2 11/2016 Baham et al.
9,517,865 B2 12/2016 Albers et al.
D777,941 S 1/2017 Piramoon
9,533,806 B2 1/2017 Ding et al.
9,550,611 B2 1/2017 Hodge
9,555,930 B2 1/2017 Campbell et al.
9,623,159 B2 4/2017 Locke
D789,522 S 6/2017 Burgess et al.
9,687,849 B2 6/2017 Bruno et al.
9,694,949 B2 7/2017 Hendricks et al.
9,709,048 B2 7/2017 Kinjo
9,732,754 B2 8/2017 Huang et al.
9,737,433 B2 8/2017 Joh
9,752,564 B2 9/2017 Arceno et al.
9,788,992 B2 10/2017 Harvie
D804,907 S 12/2017 Sandoval
D806,236 S 12/2017 Lin
9,868,564 B2 1/2018 Mcgirr et al.
D814,239 S 4/2018 Arora
D817,484 S 5/2018 Lafond
9,968,908 B2 5/2018 Ladrech et al.
10,010,393 B1 7/2018 Nguyen et al.
10,037,640 B2 7/2018 Gordon
10,058,470 B2 8/2018 Phillips
10,098,990 B2 10/2018 Koch et al.
D835,264 S 12/2018 Mozzicato et al.
D835,779 S 12/2018 Mozzicato et al.
D840,533 S 2/2019 Mozzicato et al.
D840,534 S 2/2019 Mozzicato et al.
10,225,376 B2 3/2019 Perez Martinez
10,226,376 B2 * 3/2019 Sanchez .................. A61F 5/443
10,258,517 B1 4/2019 Maschino et al.
D848,612 S 5/2019 Mozzicato et al.
10,307,305 B1 6/2019 Hodges
10,335,121 B2 7/2019 Desai
D856,512 S 8/2019 Cowart et al.
10,376,406 B2 8/2019 Newton
10,376,407 B2 8/2019 Newton
10,390,989 B2 8/2019 Sanchez et al.
D858,144 S 9/2019 Fu
10,406,039 B2 9/2019 Villarreal
10,407,222 B2 9/2019 Allen
10,478,356 B2 11/2019 Griffin
10,500,108 B1 12/2019 Maschino et al.
10,502,198 B2 12/2019 Stumpf et al.
10,538,366 B2 1/2020 Pentelovitch et al.
10,569,938 B2 2/2020 Zhao et al.
10,577,156 B2 3/2020 Dagnelie et al.
RE47,930 E 4/2020 Cho
10,618,721 B2 4/2020 Vazin
D884,390 S 5/2020 Wang
10,669,079 B2 6/2020 Freedman et al.

(56) References Cited

U.S. PATENT DOCUMENTS

D892,315 S 8/2020 Airy
10,730,672 B2 8/2020 Bertram et al.
10,737,848 B2 8/2020 Philip et al.
10,765,854 B2 9/2020 Law et al.
10,766,670 B2 9/2020 Kittmann
10,806,623 B2 10/2020 VanMiddendorp et al.
10,806,642 B2 10/2020 Tagomori et al.
D901,214 S 11/2020 Hu
10,849,799 B2 12/2020 Nishikawa et al.
10,857,025 B2 12/2020 Davis et al.
10,865,017 B1 12/2020 Cowart et al.
10,889,412 B2 1/2021 West et al.
10,913,581 B2 2/2021 Stahlecker
D912,244 S 3/2021 Rehm et al.
10,952,889 B2 3/2021 Newton et al.
10,973,378 B2 4/2021 Ryu et al.
10,973,678 B2 4/2021 Newton et al.
10,974,874 B2 4/2021 Ragias et al.
11,000,401 B2 5/2021 Ecklund et al.
11,002,165 B2 5/2021 Poulin
D923,365 S 6/2021 Wang
11,020,567 B2 6/2021 Rule et al.
11,026,829 B2 6/2021 Harvie
11,027,900 B2 6/2021 Liu
11,045,346 B2 6/2021 Argent et al.
D928,946 S 8/2021 Sanchez et al.
11,090,183 B2 8/2021 Sanchez et al.
11,160,695 B2 11/2021 Febo et al.
11,160,697 B2 11/2021 Maschino et al.
11,168,420 B2 11/2021 Kinugasa et al.
11,179,506 B2 11/2021 Barr et al.
11,199,116 B2 12/2021 Ostromecki et al.
11,207,206 B2 12/2021 Sharma et al.
D941,998 S 1/2022 Tretheway et al.
11,226,376 B2 1/2022 Yamauchi et al.
11,253,389 B2 2/2022 Sharma et al.
11,253,407 B2 2/2022 Miao et al.
11,326,586 B2 5/2022 Milner et al.
11,369,508 B2 6/2022 Ecklund et al.
11,369,524 B2 6/2022 Hubbard et al.
11,376,152 B2 7/2022 Sanchez et al.
11,382,786 B2 * 7/2022 Sanchez ................ A61F 5/4404
11,382,788 B2 7/2022 Hjorth et al.
11,389,318 B2 7/2022 Radl et al.
11,395,871 B2 7/2022 Radl et al.
11,399,990 B2 8/2022 Suyama
11,426,303 B2 8/2022 Davis et al.
11,446,174 B2 9/2022 Newton
11,504,265 B2 11/2022 Godinez et al.
11,529,252 B2 12/2022 Glithero et al.
11,547,788 B2 1/2023 Radl et al.
11,806,266 B2 * 11/2023 Sanchez .................. A61F 5/443
11,813,189 B2 11/2023 Hussey et al.
11,839,567 B2 12/2023 Davis et al.
D1,010,109 S 1/2024 Ecklund et al.
11,857,716 B2 1/2024 Lee et al.
11,865,030 B2 1/2024 Davis et al.
11,890,221 B2 2/2024 Ulreich et al.
11,911,160 B2 2/2024 Woodard et al.
11,925,575 B2 3/2024 Newton
11,938,053 B2 3/2024 Austermann et al.
11,944,740 B2 4/2024 Hughett et al.
11,994,122 B2 5/2024 Bodain
11,998,475 B2 6/2024 Becker et al.
12,023,457 B2 7/2024 Mann et al.
12,042,422 B2 7/2024 Davis et al.
12,048,644 B2 7/2024 Davis
D1,038,385 S 8/2024 Ecklund et al.
12,064,372 B2 8/2024 Godinez et al.
12,070,432 B2 8/2024 Tourchak et al.
12,090,083 B2 9/2024 Ecklund et al.
12,121,468 B2 * 10/2024 Sanchez .................. A61F 5/455
12,133,813 B2 11/2024 Ulreich et al.
12,138,195 B2 11/2024 Alder et al.
D1,054,019 S 12/2024 Miyawaki
12,161,579 B2 12/2024 Sanchez et al.
D1,059,585 S 1/2025 Miyawaki
D1,059,586 S 1/2025 Miyawaki
12,186,229 B2 1/2025 Davis et al.
12,193,962 B2 1/2025 Newton et al.
12,208,031 B2 1/2025 Knapp et al.
12,233,003 B2 2/2025 Newton
D1,067,424 S 3/2025 Naughton et al.
12,245,966 B2 3/2025 Newton
12,257,173 B2 3/2025 Newton et al.
12,274,638 B2 * 4/2025 Spector ................ A61F 5/4405
D1,074,995 S 5/2025 Laffay et al.
12,324,765 B2 6/2025 Sanchez et al.
12,350,190 B2 7/2025 Hughett, Sr. et al.
12,447,042 B2 10/2025 Martin et al.
12,465,515 B2 11/2025 Brooks
D1,104,255 S 12/2025 Hanna et al.
D1,107,222 S 12/2025 Ecklund et al.
2001/0037097 A1 11/2001 Cheng et al.
2001/0037098 A1 11/2001 Snyder
2001/0054426 A1 12/2001 Knudson et al.
2002/0019614 A1 2/2002 Woon
2002/0026161 A1 2/2002 Grundke
2002/0026163 A1 2/2002 Grundke
2002/0033200 A1 3/2002 Alex et al.
2002/0042945 A1 4/2002 Sands
2002/0087131 A1 7/2002 Wolff et al.
2002/0091364 A1 7/2002 Prabhakar
2002/0189992 A1 12/2002 Schmidt et al.
2002/0193760 A1 12/2002 Thompson
2002/0193762 A1 12/2002 Suydam
2003/0004436 A1 1/2003 Schmidt et al.
2003/0018309 A1 1/2003 Breznock
2003/0032931 A1 2/2003 Grundke et al.
2003/0032944 A1 2/2003 Cawood
2003/0073964 A1 4/2003 Palumbo et al.
2003/0074724 A1 4/2003 Sands
2003/0097100 A1 5/2003 Watson
2003/0120178 A1 6/2003 Heki
2003/0129178 A1 7/2003 Wegman et al.
2003/0157859 A1 8/2003 Ishikawa
2003/0181880 A1 9/2003 Schwartz
2003/0195484 A1 10/2003 Harvie
2003/0204173 A1 10/2003 Burns et al.
2003/0233079 A1 12/2003 Parks et al.
2004/0002687 A1 1/2004 Burns et al.
2004/0006321 A1 1/2004 Cheng et al.
2004/0015141 A1 1/2004 Cheng et al.
2004/0056122 A1 3/2004 Male et al.
2004/0084465 A1 5/2004 Luburic
2004/0098794 A1 5/2004 Ernest et al.
2004/0102753 A1 5/2004 Butler
2004/0127872 A1 7/2004 Petryk et al.
2004/0128749 A1 7/2004 Scott
2004/0143229 A1 7/2004 Easter
2004/0147863 A1 7/2004 Diaz et al.
2004/0147894 A1 7/2004 Mizutani et al.
2004/0147895 A1 7/2004 Mizutani et al.
2004/0158221 A1 8/2004 Mizutani et al.
2004/0176731 A1 * 9/2004 Cheng ..................... A61F 5/455 604/329
2004/0176746 A1 9/2004 Forral
2004/0181201 A1 9/2004 Mizutani et al.
2004/0187200 A1 9/2004 Otto et al.
2004/0191919 A1 9/2004 Unger et al.
2004/0194792 A1 10/2004 Zhuang et al.
2004/0200936 A1 10/2004 Opperthauser
2004/0207530 A1 10/2004 Nielsen
2004/0236292 A1 11/2004 Tazoe et al.
2004/0243075 A1 12/2004 Harvie
2004/0254547 A1 12/2004 Okabe et al.
2005/0010182 A1 1/2005 Parks et al.
2005/0010197 A1 1/2005 Lau et al.
2005/0033248 A1 2/2005 Machida et al.
2005/0065471 A1 3/2005 Kuntz
2005/0070861 A1 3/2005 Okabe et al.
2005/0070862 A1 3/2005 Tazoe et al.
2005/0082300 A1 4/2005 Modrell et al.
2005/0097662 A1 5/2005 Leimkuhler et al.

(56) References Cited

U.S. PATENT DOCUMENTS

2005/0101924 A1 5/2005 Elson et al.
2005/0119630 A1 6/2005 Harvie
2005/0131361 A1 6/2005 Miskie
2005/0137557 A1 6/2005 Swiecicki et al.
2005/0137560 A1 6/2005 Mizutani et al.
2005/0137561 A1 6/2005 Mizutani et al.
2005/0148984 A1 7/2005 Lindsay et al.
2005/0154360 A1 7/2005 Harvie
2005/0177070 A1 8/2005 Levinson et al.
2005/0197645 A1 9/2005 Karpowicz et al.
2005/0215969 A1 9/2005 Mizutani et al.
2005/0273069 A1 12/2005 Mizutani et al.
2005/0273920 A1 12/2005 Marinas
2005/0277903 A1 12/2005 Mizutani et al.
2005/0277904 A1 12/2005 Chase et al.
2005/0279359 A1 12/2005 LeBlanc et al.
2006/0004332 A1 1/2006 Marx
2006/0005307 A1 1/2006 Arguelles
2006/0015080 A1 1/2006 Mahnensmith
2006/0015081 A1 1/2006 Suzuki et al.
2006/0016778 A1 1/2006 Park
2006/0069359 A1 3/2006 Dipalma et al.
2006/0079852 A1 4/2006 Bubb et al.
2006/0079854 A1 4/2006 Kay et al.
2006/0100596 A1 5/2006 Miskie
2006/0111648 A1 5/2006 Vermaak
2006/0113334 A1 6/2006 Mikhail et al.
2006/0155214 A1 7/2006 Wightman
2006/0166350 A1 7/2006 Lowe et al.
2006/0171997 A1 8/2006 Gruenbacher et al.
2006/0180566 A1 8/2006 Mataya
2006/0200102 A1 9/2006 Cooper
2006/0229575 A1 10/2006 Boiarski
2006/0229576 A1 10/2006 Conway et al.
2006/0231648 A1 10/2006 Male et al.
2006/0235266 A1 10/2006 Nan
2006/0235359 A1 10/2006 Marland
2006/0241553 A1 10/2006 Harvie
2006/0269439 A1 11/2006 White
2006/0277670 A1 12/2006 Baker et al.
2007/0006368 A1 1/2007 Key et al.
2007/0010797 A1 1/2007 Nishtala et al.
2007/0016152 A1 1/2007 Karpowicz et al.
2007/0025886 A1 2/2007 Yong
2007/0038194 A1 2/2007 Wada et al.
2007/0055209 A1 3/2007 Patel et al.
2007/0073252 A1 3/2007 Forgrave
2007/0106177 A1 5/2007 Hama
2007/0117880 A1 5/2007 Elson et al.
2007/0118993 A1 5/2007 Bates
2007/0135786 A1 6/2007 Schmidt et al.
2007/0137718 A1 6/2007 Rushlander et al.
2007/0149935 A1 6/2007 Dirico
2007/0191804 A1 8/2007 Coley
2007/0203464 A1 8/2007 Green et al.
2007/0214553 A1 9/2007 Carromba et al.
2007/0225663 A1 9/2007 Watt et al.
2007/0225666 A1 9/2007 Otto
2007/0225668 A1 9/2007 Otto
2007/0266486 A1 11/2007 Ramirez
2007/0270716 A1 11/2007 Wu et al.
2007/0282309 A1 12/2007 Bengtson et al.
2008/0004576 A1 1/2008 Tanaka et al.
2008/0015526 A1 1/2008 Reiner et al.
2008/0015527 A1 1/2008 House
2008/0033386 A1 2/2008 Okabe et al.
2008/0041869 A1 2/2008 Backaert
2008/0077099 A1 3/2008 House
2008/0091153 A1 4/2008 Harvie
2008/0091158 A1 4/2008 Yang
2008/0114327 A1 5/2008 Barge
2008/0140033 A1 6/2008 Burgess et al.
2008/0167634 A1 7/2008 Kouta et al.
2008/0183157 A1 7/2008 Walters
2008/0200884 A1 8/2008 Perkins et al.
2008/0215031 A1 9/2008 Belfort et al.
2008/0234642 A1 9/2008 Patterson et al.
2008/0269703 A1 10/2008 Collins et al.
2008/0281282 A1 11/2008 Finger et al.
2008/0287894 A1 11/2008 Van Den Heuvel et al.
2008/0312550 A1 12/2008 Nishtala et al.
2009/0025717 A1 1/2009 Pinel
2009/0048570 A1 2/2009 Jensen
2009/0056003 A1 3/2009 Ivie et al.
2009/0069761 A1 3/2009 Vogel
2009/0069765 A1 3/2009 Wortham
2009/0120179 A1 5/2009 Nylander et al.
2009/0192482 A1 7/2009 Dodge et al.
2009/0199857 A1 8/2009 Peake et al.
2009/0226541 A1 9/2009 Scholz et al.
2009/0234312 A1 9/2009 Otoole et al.
2009/0247968 A1 10/2009 Brooks et al.
2009/0251510 A1 10/2009 Noro et al.
2009/0254040 A1 10/2009 Bierman et al.
2009/0259206 A1 10/2009 Kai et al.
2009/0264840 A1 10/2009 Virginio
2009/0270822 A1 10/2009 Medeiros
2009/0281510 A1 11/2009 Fisher
2009/0283982 A1 11/2009 Thomas
2009/0306610 A1 12/2009 Van Den Heuvel et al.
2010/0004612 A1 1/2010 Thevenin
2010/0030189 A1 2/2010 Fleming
2010/0031429 A1 2/2010 Kim et al.
2010/0032789 A1 2/2010 Schoen et al.
2010/0058660 A1 3/2010 Williams
2010/0121289 A1 5/2010 Parks et al.
2010/0160882 A1 6/2010 Lowe
2010/0174250 A1 7/2010 Hu et al.
2010/0179493 A1 7/2010 Heagle et al.
2010/0185168 A1 7/2010 Graauw et al.
2010/0198172 A1 8/2010 Wada et al.
2010/0211032 A1 8/2010 Tsai et al.
2010/0234820 A1 9/2010 Tsai et al.
2010/0241104 A1 9/2010 Gilbert
2010/0263113 A1 10/2010 Shelton et al.
2010/0310845 A1 12/2010 Bond et al.
2011/0022011 A1 1/2011 Edward
2011/0028920 A1 2/2011 Johannison
2011/0028922 A1 2/2011 Kay et al.
2011/0034889 A1 2/2011 Smith
2011/0036837 A1 2/2011 Shang
2011/0040267 A1 2/2011 Wada et al.
2011/0040271 A1 2/2011 Rogers et al.
2011/0054426 A1 3/2011 Stewart et al.
2011/0060299 A1 3/2011 Wada et al.
2011/0060300 A1 3/2011 Weig et al.
2011/0077495 A1 3/2011 Gilbert
2011/0077606 A1 3/2011 Wilcox et al.
2011/0087337 A1 4/2011 Forsell
2011/0145993 A1 6/2011 Rader et al.
2011/0152802 A1 6/2011 Dicamillo et al.
2011/0152842 A1 6/2011 Graffam et al.
2011/0164147 A1 7/2011 Takahashi et al.
2011/0172620 A1 7/2011 Khambatta
2011/0172625 A1 7/2011 Wada et al.
2011/0198904 A1 8/2011 Thomas et al.
2011/0202024 A1 8/2011 Cozzens
2011/0238023 A1 9/2011 Slayton
2011/0240648 A1 10/2011 Tucker
2011/0251572 A1 10/2011 Nishtala et al.
2011/0265889 A1 11/2011 Tanaka et al.
2011/0276020 A1 11/2011 Mitsui
2012/0004079 A1 1/2012 Hyacinth
2012/0029452 A1 2/2012 Roedsten
2012/0035577 A1 2/2012 Tomes et al.
2012/0041400 A1 2/2012 Christensen
2012/0059328 A1 3/2012 Dikeman et al.
2012/0066825 A1 3/2012 Birbara et al.
2012/0103347 A1 5/2012 Wheaton et al.
2012/0116336 A1 5/2012 Sharma et al.
2012/0137420 A1 6/2012 Gordon et al.
2012/0165768 A1 6/2012 Sekiyama et al.
2012/0209216 A1 8/2012 Jensen et al.
2012/0209225 A1 8/2012 Hu et al.

(56) References Cited

U.S. PATENT DOCUMENTS

2012/0210503 A1 8/2012 Anzivino et al.
2012/0215187 A1 8/2012 Tippet et al.
2012/0233761 A1 9/2012 Huang
2012/0245541 A1 9/2012 Suzuki et al.
2012/0245542 A1 9/2012 Suzuki et al.
2012/0245547 A1 9/2012 Wilcox et al.
2012/0253303 A1 10/2012 Suzuki et al.
2012/0271259 A1 10/2012 Ulert
2012/0296305 A1 11/2012 Barraza Khaled et al.
2012/0316522 A1 12/2012 Carter et al.
2012/0330256 A1 12/2012 Wilcox et al.
2013/0006206 A1 1/2013 Wada et al.
2013/0019374 A1 1/2013 Schwartz
2013/0036544 A1 2/2013 Lee et al.
2013/0045651 A1 2/2013 Esteves et al.
2013/0046258 A1 2/2013 Chambers
2013/0053804 A1 2/2013 Soerensen et al.
2013/0096523 A1 4/2013 Chang et al.
2013/0110059 A1 5/2013 Kossow et al.
2013/0138064 A1 5/2013 Stroebech et al.
2013/0144240 A1 6/2013 Ellis
2013/0150813 A1 6/2013 Gordon et al.
2013/0158494 A1 6/2013 Ong et al.
2013/0165880 A1 6/2013 Amos et al.
2013/0211385 A1 8/2013 Lazarus
2013/0218112 A1 8/2013 Thompson
2013/0245496 A1 9/2013 Wells et al.
2013/0245586 A1 9/2013 Jha
2013/0274711 A1 10/2013 O'Day
2013/0292537 A1 11/2013 Dirico
2013/0324954 A1 12/2013 Friedrich
2013/0330501 A1 12/2013 Aizenberg et al.
2014/0005647 A1 1/2014 Shuffler et al.
2014/0031774 A1 1/2014 Bengtson
2014/0039432 A1 2/2014 Dunbar et al.
2014/0039440 A1 2/2014 Doescher
2014/0058347 A1 2/2014 Marquette
2014/0107595 A1 4/2014 Blott et al.
2014/0107599 A1 4/2014 Fink et al.
2014/0157499 A1 6/2014 Suzuki et al.
2014/0171889 A1 6/2014 Hopman et al.
2014/0182051 A1 7/2014 Tanimoto et al.
2014/0196189 A1 7/2014 Lee et al.
2014/0230831 A1 8/2014 Zaltsberg et al.
2014/0257231 A1 9/2014 Wang et al.
2014/0303582 A1 10/2014 Wright et al.
2014/0316381 A1 10/2014 Reglin
2014/0325746 A1 11/2014 Block
2014/0343516 A1 11/2014 Coulthard et al.
2014/0348139 A1 11/2014 Gomez Martinez
2014/0352050 A1 12/2014 Yao et al.
2014/0371628 A1 12/2014 Desai
2015/0045757 A1 2/2015 Lee et al.
2015/0047114 A1 2/2015 Ramirez
2015/0048089 A1 2/2015 Robertson
2015/0135423 A1 5/2015 Sharpe et al.
2015/0157300 A1 6/2015 Ealovega et al.
2015/0209188 A1 7/2015 Scheremet et al.
2015/0209194 A1 7/2015 Heyman
2015/0267862 A1 9/2015 Mishler
2015/0290421 A1 10/2015 Glickman et al.
2015/0290425 A1 10/2015 Macy et al.
2015/0320583 A1 11/2015 Harvie
2015/0329255 A1 11/2015 Rzepecki
2015/0342799 A1 12/2015 Michiels et al.
2015/0359660 A1 12/2015 Harvie
2015/0359996 A1 12/2015 Arora et al.
2015/0366699 A1 12/2015 Nelson
2015/0374535 A1 12/2015 Davis et al.
2016/0008193 A1 1/2016 Schulke
2016/0029998 A1 2/2016 Brister et al.
2016/0030228 A1 2/2016 Jones
2016/0038356 A1 2/2016 Yao et al.
2016/0051395 A1 2/2016 Ugarte M.D.
2016/0058322 A1 3/2016 Brister et al.
2016/0060001 A1 3/2016 Wada et al.
2016/0100976 A1 4/2016 Conway et al.
2016/0106604 A1 4/2016 Timm
2016/0113809 A1 4/2016 Kim
2016/0135792 A1 5/2016 Cai
2016/0136338 A1 5/2016 Lee et al.
2016/0183689 A1 6/2016 Miner
2016/0256022 A1 9/2016 Le
2016/0270982 A1 9/2016 Raycheck et al.
2016/0278662 A1 9/2016 Brister et al.
2016/0327553 A1 11/2016 Edwards et al.
2016/0357400 A1 12/2016 Penha et al.
2016/0366699 A1 12/2016 Zhang et al.
2016/0367226 A1* 12/2016 Newton ............... A01K 23/005
2016/0367411 A1 12/2016 Justiz et al.
2016/0374848 A1 12/2016 Sanchez et al.
2017/0007438 A1 1/2017 Harvie
2017/0014560 A1 1/2017 Minskoff et al.
2017/0042724 A1 2/2017 Ugarte
2017/0042748 A1 2/2017 Griffin
2017/0049605 A1 2/2017 Wisniewski
2017/0100276 A1 4/2017 Joh
2017/0107312 A1 4/2017 Hinayama et al.
2017/0128638 A1 5/2017 Giezendanner et al.
2017/0136209 A1 5/2017 Burnett et al.
2017/0143534 A1 5/2017 Sanchez
2017/0165100 A1 6/2017 Jackson et al.
2017/0165405 A1 6/2017 Muser et al.
2017/0189225 A1 7/2017 Voorhees et al.
2017/0202692 A1 7/2017 Laniado
2017/0216081 A1 8/2017 Accosta
2017/0238911 A1 8/2017 Duval
2017/0246026 A1 8/2017 Laniado
2017/0252014 A1 9/2017 Siller Gonzalez et al.
2017/0252202 A9 9/2017 Sanchez et al.
2017/0266031 A1* 9/2017 Sanchez .................. A61F 5/443
2017/0266658 A1 9/2017 Bruno et al.
2017/0281399 A1 10/2017 Vanmiddendorp et al.
2017/0281419 A1 10/2017 Pintado
2017/0312116 A1 11/2017 Laniado
2017/0312405 A1 11/2017 Newton
2017/0325788 A1 11/2017 Ealovega et al.
2017/0333244 A1 11/2017 Laniado
2017/0340489 A1 11/2017 Yamada
2017/0348139 A1 12/2017 Newton et al.
2017/0354532 A1 12/2017 Holt
2017/0354551 A1 12/2017 Gawley et al.
2017/0367873 A1 12/2017 Grannum
2018/0002075 A1 1/2018 Lee
2018/0008451 A1 1/2018 Stroebech
2018/0008804 A1 1/2018 Laniado
2018/0021218 A1 1/2018 Brosch et al.
2018/0028349 A1 2/2018 Newton et al.
2018/0037384 A1 2/2018 Archeny et al.
2018/0049910 A1 2/2018 Newton
2018/0064572 A1 3/2018 Wiltshire
2018/0104131 A1 4/2018 Killian
2018/0127187 A1 5/2018 Sewell
2018/0149635 A1 5/2018 Abir
2018/0169281 A1 6/2018 Russell et al.
2018/0193215 A1 7/2018 Davies et al.
2018/0200101 A1 7/2018 Su
2018/0214297 A1 8/2018 Hughett et al.
2018/0215649 A1 8/2018 Wada et al.
2018/0221216 A1 8/2018 Benz et al.
2018/0228642 A1 8/2018 Davis et al.
2018/0229014 A1 8/2018 Guirguis et al.
2018/0256384 A1 9/2018 Kasirye
2018/0271694 A1 9/2018 Fernandez et al.
2018/0280236 A1 10/2018 Ludin et al.
2018/0317892 A1 11/2018 Catlin
2018/0325748 A1 11/2018 Sharma et al.
2019/0001029 A1 1/2019 Davie et al.
2019/0001030 A1 1/2019 Braga et al.
2019/0021899 A1 1/2019 Vlet
2019/0029869 A1 1/2019 Huchthausen
2019/0038451 A1 2/2019 Harvie
2019/0046102 A1 2/2019 Kushnir et al.
2019/0059938 A1 2/2019 Holsten

(56) References Cited

U.S. PATENT DOCUMENTS

2019/0060138 A1 2/2019 Marquez et al.
2019/0091059 A1 3/2019 Gabriel
2019/0100362 A1 4/2019 Meyers et al.
2019/0133126 A1 5/2019 Modak et al.
2019/0133814 A1 5/2019 Tammen et al.
2019/0142624 A1* 5/2019 Sanchez .................. A61F 5/453 604/319
2019/0224036 A1* 7/2019 Sanchez .................. A61F 5/455
2019/0226189 A1 7/2019 Braxton
2019/0240079 A1 8/2019 Tuli
2019/0247222 A1 8/2019 Ecklund et al.
2019/0247223 A1 8/2019 Brun et al.
2019/0247623 A1 8/2019 Helm et al.
2019/0282391 A1 9/2019 Johannes et al.
2019/0314189 A1 10/2019 Acosta
2019/0314190 A1 10/2019 Sanchez et al.
2019/0321587 A1 10/2019 Mcmenamin et al.
2019/0344934 A1 11/2019 Faerber et al.
2019/0365303 A1 12/2019 Bullington et al.
2019/0365307 A1 12/2019 Laing et al.
2019/0365561 A1 12/2019 Newton et al.
2019/0374373 A1 12/2019 Joh
2020/0008985 A1 1/2020 Nguyen et al.
2020/0016012 A1 1/2020 Dutkiewicz
2020/0030595 A1 1/2020 Boukidjian et al.
2020/0040561 A1 2/2020 Sugawara
2020/0046544 A1 2/2020 Godinez et al.
2020/0055638 A1 2/2020 Lau et al.
2020/0070392 A1 3/2020 Huber et al.
2020/0085609 A1 3/2020 Schelch et al.
2020/0085610 A1 3/2020 Cohn et al.
2020/0086090 A1 3/2020 Von Weymarn-schärli et al.
2020/0107518 A1 4/2020 Hiroshima et al.
2020/0129322 A1 4/2020 Leuckel
2020/0171217 A9 6/2020 Braga et al.
2020/0179177 A1 6/2020 Erdem et al.
2020/0187918 A1 6/2020 Wiygul
2020/0206015 A1 7/2020 Langer
2020/0206039 A1 7/2020 Mclain
2020/0214910 A1 7/2020 Varona et al.
2020/0216898 A1 7/2020 Hubbell
2020/0216989 A1 7/2020 Kinugasa et al.
2020/0229964 A1 7/2020 Staali et al.
2020/0231343 A1 7/2020 Freedman et al.
2020/0232841 A1 7/2020 Satish et al.
2020/0246172 A1 8/2020 Ho
2020/0246203 A1 8/2020 Tulk et al.
2020/0255189 A1 8/2020 Liu
2020/0261280 A1 8/2020 Heyman
2020/0276046 A1 9/2020 Staali et al.
2020/0306075 A1 10/2020 Newton et al.
2020/0315837 A1 10/2020 Radl et al.
2020/0315838 A1 10/2020 Eckert
2020/0315872 A1 10/2020 Viens et al.
2020/0315874 A1 10/2020 Viens et al.
2020/0331672 A1 10/2020 Bertram et al.
2020/0345332 A1 11/2020 Duval
2020/0352774 A1 11/2020 Rabinowitz et al.
2020/0353135 A1 11/2020 Gregory et al.
2020/0367677 A1 11/2020 Silsby et al.
2020/0369444 A1 11/2020 Silsby et al.
2020/0375781 A1 12/2020 Staali et al.
2020/0375810 A1 12/2020 Carlin et al.
2020/0384242 A1 12/2020 Havard et al.
2020/0385179 A1 12/2020 Mccourt
2020/0390591 A1 12/2020 Glithero et al.
2020/0390592 A1 12/2020 Merrill
2020/0398024 A1 12/2020 Fletter et al.
2020/0405521 A1 12/2020 Glasroe
2020/0405523 A1 12/2020 Obst et al.
2021/0007910 A1 1/2021 Furukawa
2021/0008771 A1 1/2021 Huber et al.
2021/0009323 A1 1/2021 Markarian et al.
2021/0020072 A1 1/2021 Moehring et al.
2021/0023279 A1 1/2021 Radl et al.
2021/0059853 A1 3/2021 Davis et al.
2021/0061523 A1 3/2021 Bytheway
2021/0069005 A1 3/2021 Sanchez et al.
2021/0069008 A1 3/2021 Blabas et al.
2021/0069009 A1 3/2021 Im
2021/0069030 A1 3/2021 Nishikawa et al.
2021/0077993 A1 3/2021 Nazareth et al.
2021/0113749 A1 4/2021 Radl et al.
2021/0121318 A1 4/2021 Pinlac
2021/0137724 A1 5/2021 Ecklund et al.
2021/0138190 A1 5/2021 Erbey et al.
2021/0154055 A1 5/2021 Villarreal
2021/0170079 A1 6/2021 Radl et al.
2021/0178390 A1 6/2021 Oueslati et al.
2021/0186742 A1 6/2021 Newton et al.
2021/0186744 A1* 6/2021 Spector .................. A61F 5/455
2021/0206144 A1 7/2021 Ewell
2021/0211568 A1 7/2021 Zhou et al.
2021/0212865 A1 7/2021 Wallajapet et al.
2021/0220162 A1 7/2021 Jamison
2021/0220163 A1 7/2021 Mayrand
2021/0228400 A1 7/2021 Glithero
2021/0228401 A1 7/2021 Becker et al.
2021/0228795 A1 7/2021 Hughett et al.
2021/0229877 A1 7/2021 Ragias et al.
2021/0236323 A1 8/2021 Austermann et al.
2021/0236324 A1 8/2021 Sweeney
2021/0251814 A1 8/2021 Jönegren et al.
2021/0267787 A1 9/2021 Nazemi
2021/0275343 A1* 9/2021 Sanchez ................ A61F 5/4404
2021/0275344 A1 9/2021 Wing
2021/0290454 A1 9/2021 Yamada
2021/0290464 A1 9/2021 Furuta
2021/0315726 A1 10/2021 Lin
2021/0315727 A1 10/2021 Jiang
2021/0353449 A1 11/2021 Sharma et al.
2021/0353450 A1 11/2021 Sharma et al.
2021/0361469 A1 11/2021 Liu et al.
2021/0369495 A1 12/2021 Cheng et al.
2021/0386925 A1 12/2021 Hartwell et al.
2021/0393433 A1 12/2021 Godinez et al.
2022/0015958 A1 1/2022 Ito
2022/0023091 A1 1/2022 Ecklund et al.
2022/0026546 A1 1/2022 Aono et al.
2022/0031290 A1 2/2022 Weed
2022/0031523 A1 2/2022 Pierpoint
2022/0039995 A1* 2/2022 Johannes ................ A61F 5/455
2022/0047410 A1 2/2022 Walthall
2022/0062025 A1 3/2022 Shields et al.
2022/0062027 A1 3/2022 Mitchell et al.
2022/0062028 A1 3/2022 Mitchell et al.
2022/0062029 A1 3/2022 Johannes et al.
2022/0066825 A1 3/2022 Saraf et al.
2022/0071811 A1 3/2022 Cheng et al.
2022/0071826 A1 3/2022 Kulkarni et al.
2022/0104965 A1 4/2022 Vaninetti et al.
2022/0104976 A1 4/2022 Hoeger et al.
2022/0104981 A1 4/2022 Jones
2022/0117773 A1 4/2022 Davis et al.
2022/0117774 A1 4/2022 Meyer et al.
2022/0117775 A1 4/2022 Jones et al.
2022/0118165 A1 4/2022 Knapp et al.
2022/0133524 A1 5/2022 Davis
2022/0151817 A1 5/2022 Mann
2022/0160949 A1 5/2022 Simiele et al.
2022/0168159 A1 6/2022 Triado et al.
2022/0193312 A1 6/2022 Lee et al.
2022/0211536 A1 7/2022 Johannes et al.
2022/0218510 A1 7/2022 Metzger et al.
2022/0229053 A1 7/2022 Levin et al.
2022/0241106 A1 8/2022 Johannes et al.
2022/0248836 A1 8/2022 Cagle et al.
2022/0257407 A1 8/2022 Johannes et al.
2022/0265460 A1 8/2022 Coker
2022/0265462 A1 8/2022 Alder et al.
2022/0270711 A1 8/2022 Feala et al.
2022/0273482 A1 9/2022 Johannes et al.
2022/0280357 A1 9/2022 Jagannathan et al.
2022/0280710 A1 9/2022 Agrawal et al.

(56) References Cited

U.S. PATENT DOCUMENTS

2022/0287689 A1* 9/2022 Johannes ................ A61F 5/453
2022/0287691 A1 9/2022 Wormser et al.
2022/0287867 A1 9/2022 Jones et al.
2022/0287868 A1 9/2022 Garvey et al.
2022/0296408 A1 9/2022 Evans et al.
2022/0305191 A1 9/2022 Joseph et al.
2022/0313222 A1 10/2022 Austermann et al.
2022/0313474 A1 10/2022 Kriscovich et al.
2022/0331170 A1 10/2022 Erdem et al.
2022/0339023 A1 10/2022 Davis et al.
2022/0339024 A1 10/2022 Johannes et al.
2022/0354685 A1 11/2022 Davis et al.
2022/0362049 A1 11/2022 Austermann et al.
2022/0370231 A1 11/2022 Wang et al.
2022/0370234 A1 11/2022 Hughett et al.
2022/0370235 A1 11/2022 Johannes et al.
2022/0370237 A1 11/2022 Parmar et al.
2022/0387001 A1 12/2022 Askenazi et al.
2022/0387693 A1 12/2022 Bannwart et al.
2022/0395390 A1 12/2022 Brooks
2022/0395391 A1 12/2022 Saunders et al.
2022/0401252 A1 12/2022 Warren
2022/0409419 A1 12/2022 Garvey et al.
2022/0409422 A1 12/2022 Schneider et al.
2023/0018845 A1 1/2023 Lee
2023/0020563 A1 1/2023 Sharma et al.
2023/0031640 A1 2/2023 Hughett et al.
2023/0037159 A1 2/2023 Brennan et al.
2023/0049924 A1 2/2023 Johannes et al.
2023/0052238 A1 2/2023 Oluwasogo
2023/0062994 A1 3/2023 Ecklund et al.
2023/0070347 A1 3/2023 Watson et al.
2023/0073708 A1 3/2023 Xu et al.
2023/0089032 A1 3/2023 Hughett et al.
2023/0091118 A1 3/2023 Watson
2023/0099821 A1* 3/2023 Radl ..................... A61M 1/742 604/321
2023/0099991 A1 3/2023 Bianchi et al.
2023/0105001 A1 4/2023 Whittome et al.
2023/0110577 A1 4/2023 Choi
2023/0138269 A1* 5/2023 Abdelal ................ A61F 5/4404 604/347
2023/0145365 A1 5/2023 Martin et al.
2023/0155253 A1 5/2023 Yin et al.
2023/0190511 A1 6/2023 Sharma et al.
2023/0210504 A1 7/2023 Kuroda et al.
2023/0210685 A1 7/2023 Fallows et al.
2023/0218426 A1 7/2023 Hughett
2023/0240884 A1 8/2023 Davis et al.
2023/0248562 A1 8/2023 Sanchez et al.
2023/0248564 A1 8/2023 Mann et al.
2023/0255812 A1 8/2023 Sanchez et al.
2023/0255813 A1 8/2023 Sanchez et al.
2023/0255815 A1* 8/2023 Newton .................. A61F 5/455 604/349
2023/0263650 A1 8/2023 Sanchez et al.
2023/0263655 A1 8/2023 Johannes et al.
2023/0277360 A1 9/2023 Lambert et al.
2023/0277362 A1 9/2023 Davis et al.
2023/0285178 A1 9/2023 Sanchez et al.
2023/0293339 A1 9/2023 James
2023/0301846 A1 9/2023 Greenwood
2023/0355423 A1 11/2023 Stevenson et al.
2023/0389900 A1 12/2023 Xie et al.
2023/0404791 A1 12/2023 Ecklund et al.
2024/0008444 A1 1/2024 Su et al.
2024/0009023 A1 1/2024 Johannes et al.
2024/0024170 A1 1/2024 Scott
2024/0033148 A1 2/2024 Gordon et al.
2024/0041638 A1 2/2024 Johannes et al.
2024/0058157 A1 2/2024 Davis
2024/0058160 A1 2/2024 Young Joyner et al.
2024/0058161 A1 2/2024 Ulreich et al.
2024/0058520 A1 2/2024 Yin et al.
2024/0065881 A1 2/2024 Kuroda et al.
2024/0082044 A1 3/2024 Nguyen et al.
2024/0099874 A1* 3/2024 Sanchez .................. A61F 5/453
2024/0108268 A1 4/2024 Woodard et al.
2024/0110318 A1 4/2024 Bendt et al.
2024/0122773 A1 4/2024 Nguyen et al.
2024/0123134 A1 4/2024 Kharkar et al.
2024/0130885 A1 4/2024 Young Joyner et al.
2024/0148539 A1 5/2024 Austermann et al.
2024/0156633 A1 5/2024 Fallows et al.
2024/0164935 A1* 5/2024 Newton ................ A61F 5/4404
2024/0180737 A1* 6/2024 Newton ................ A61F 5/4404
2024/0252343 A1 8/2024 Voda
2024/0261131 A1 8/2024 Garvey et al.
2024/0268986 A1 8/2024 Barnes et al.
2024/0268989 A1 8/2024 Martin et al.
2024/0268991 A1 8/2024 Davis
2024/0269027 A1 8/2024 Tourchak et al.
2024/0285425 A1 8/2024 Donohoe et al.
2024/0325190 A1 10/2024 Minchew et al.
2024/0341998 A1 10/2024 Julian et al.
2024/0358539 A1 10/2024 Gallup
2024/0358542 A1 10/2024 Richardson et al.
2024/0374414 A1 11/2024 Richardson et al.
2025/0009552 A1 1/2025 Blabas et al.
2025/0073055 A1 3/2025 Ecklund et al.
2025/0107920 A1 4/2025 Fallows et al.
2025/0107921 A1 4/2025 Sanchez et al.
2025/0367358 A1 12/2025 Smith et al.

FOREIGN PATENT DOCUMENTS

AU 2022349367 A1 4/2024
CA 2165286 C 9/1999
CA 2335223 A1 1/2000
CA 2354132 A1 6/2000
CA 2359091 C 9/2003
CA 2488867 C 8/2007
CA 3031934 A1 2/2018
CA 3050918 A1 8/2018
CA 3098571 A1 11/2019
CA 3144181 A1 1/2021
CA 3188651 A1 7/2023
CN 2269203 Y 12/1997
CN 1332620 A 1/2002
CN 1434693 A 8/2003
CN 1533755 A 10/2004
CN 1579348 A 2/2005
CN 1602825 A 4/2005
CN 1638708 A 7/2005
CN 1720888 A 1/2006
CN 2936204 Y 8/2007
CN 101262836 A 9/2008
CN 101522148 A 9/2009
CN 102159159 A 8/2011
CN 202184840 U 4/2012
CN 102481441 A 5/2012
CN 202463712 U 10/2012
CN 202950810 U 5/2013
CN 103533968 A 1/2014
CN 103717180 A 4/2014
CN 204562697 U 8/2015
CN 105411783 A 3/2016
CN 105451607 A 3/2016
CN 105451693 A 3/2016
CN 105534632 A 5/2016
CN 105616072 A 6/2016
CN 106132360 A 11/2016
CN 106137631 A 11/2016
CN 205849719 U 1/2017
CN 205924282 U 2/2017
CN 106726089 A 5/2017
CN 107847384 A 3/2018
CN 107920912 A 4/2018
CN 108420590 A 8/2018
CN 207785556 U 8/2018
CN 110171118 A 8/2019
CN 209285902 U 8/2019
CN 110381883 A 10/2019
CN 111465375 A 7/2020

(56) References Cited

FOREIGN PATENT DOCUMENTS

| | | | |
|---|---|---|---|
| CN | 211198839 | U | 8/2020 |
| CN | 111991136 | A | 11/2020 |
| CN | 112022488 | A | 12/2020 |
| CN | 212234893 | U | 12/2020 |
| CN | 112312867 | A | 2/2021 |
| CN | 212466312 | U | 2/2021 |
| CN | 112566550 | A | 3/2021 |
| CN | 112603184 | A | 4/2021 |
| CN | 213490035 | U | 6/2021 |
| CN | 114007493 | A | 2/2022 |
| CN | 114375187 | A | 4/2022 |
| CN | 116096332 | A | 5/2023 |
| DE | 1516466 | A1 | 6/1969 |
| DE | 2721330 | A1 | 11/1977 |
| DE | 2742298 | A1 | 3/1978 |
| DE | 3104356 | A1 | 9/1982 |
| DE | 9407554.9 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 202005013173 | U1 | 6/2006 |
| DE | 102005037762 | B3 | 9/2006 |
| DE | 202006018506 | U1 | 3/2007 |
| DE | 102011103783 | A1 | 12/2012 |
| DE | 102012112818 | A1 | 6/2014 |
| DE | 202015104597 | U1 | 7/2016 |
| DE | 102018118570 | A1 | 2/2020 |
| DE | 102020121462 | B3 | 1/2022 |
| DK | 9600118 | | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0220962 | A1 | 5/1987 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0483730 | A1 | 5/1992 |
| EP | 0610638 | A1 | 8/1994 |
| EP | 0613355 | A1 | 9/1994 |
| EP | 0711536 | A1 | 5/1996 |
| EP | 0613355 | B1 | 1/1997 |
| EP | 0680296 | B1 | 5/1997 |
| EP | 0787472 | A1 | 8/1997 |
| EP | 0945231 | A2 | 9/1999 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2470251 | B1 | 12/2014 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3777801 | A1 | 2/2021 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3749230 | B1 | 3/2023 |
| EP | 3569205 | B1 | 6/2023 |
| EP | 4192402 | A1 | 6/2023 |
| EP | 4218702 | A1 | 8/2023 |
| EP | 3624742 | B1 | 1/2024 |
| EP | 4382082 | A2 | 6/2024 |
| EP | 4445881 | A2 | 10/2024 |
| EP | 4464288 | A2 | 11/2024 |
| EP | 4215134 | B1 | 1/2025 |
| EP | 4494611 | A2 | 1/2025 |
| EP | 4527361 | A2 | 3/2025 |
| FR | 2294812 | A1 | 7/1976 |
| FR | 2826704 | A1 | 1/2003 |
| GB | 871820 | A | 7/1961 |
| GB | 0873045 | A | 7/1961 |
| GB | 996370 | A | 6/1965 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2415386 | A | 12/2005 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58130026 | A | 8/1983 |
| JP | S58188016 | U | 12/1983 |
| JP | S59118161 | A | 7/1984 |
| JP | S61502100 | A | 9/1986 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H0515928 | U | 3/1993 |
| JP | H05123349 | A | 5/1993 |
| JP | H05123350 | A | 5/1993 |
| JP | H0625981 | U | 4/1994 |
| JP | H0626264 | U | 4/1994 |
| JP | 3087938 | B2 | 10/1995 |
| JP | H085630 | A | 1/1996 |
| JP | H08117271 | A | 5/1996 |
| JP | H08510924 | A | 11/1996 |
| JP | 2686634 | B2 | 12/1997 |
| JP | H1038669 | A | 2/1998 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000152953 | A | 6/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |

(56) References Cited

FOREIGN PATENT DOCUMENTS

| | | | |
|---|---|---|---|
| JP | 2002502667 | A | 1/2002 |
| JP | 2002102285 | A | 4/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003227004 | A | 8/2003 |
| JP | 2003528691 | A | 9/2003 |
| JP | 2004057578 | A | 2/2004 |
| JP | 2004130056 | A | 4/2004 |
| JP | 2004267400 | A | 9/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 12/2005 |
| JP | 2006026108 | A | 2/2006 |
| JP | 3123547 | B2 | 6/2006 |
| JP | 2006136491 | A | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2008278928 | A | 11/2008 |
| JP | 2009500111 | A | 1/2009 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | A | 8/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011522584 | A | 8/2011 |
| JP | 2011202664 | A | 10/2011 |
| JP | 2011218130 | A | 11/2011 |
| JP | 2011224070 | A | 11/2011 |
| JP | 3175719 | U | 4/2012 |
| JP | 2012522014 | A | 9/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |
| JP | 2015221390 | A | 12/2015 |
| JP | 2016521191 | A | 7/2016 |
| JP | 2017014698 | A | 1/2017 |
| JP | 3208707 | U | 2/2017 |
| JP | 3209321 | U | 3/2017 |
| JP | 2017070400 | A | 4/2017 |
| JP | 2017512603 | A | 5/2017 |
| JP | 2017127596 | A | 7/2017 |
| JP | 2017201272 | A | 11/2017 |
| JP | 2019010375 | A | 1/2019 |
| JP | 2019076342 | A | 5/2019 |
| JP | 2019525811 | A | 9/2019 |
| JP | 2019170942 | A | 10/2019 |
| JP | 2019533492 | A | 11/2019 |
| JP | 2020510464 | A | 4/2020 |
| JP | 2020520775 | A | 7/2020 |
| JP | 2020124425 | A | 8/2020 |
| JP | 2021007472 | A | 1/2021 |
| JP | 2021041145 | A | 3/2021 |
| JP | 2021074491 | A | 5/2021 |
| JP | 2021120686 | A | 8/2021 |
| JP | 2021520952 | A | 8/2021 |
| JP | 2021522009 | A | 8/2021 |
| JP | 2021522013 | A | 8/2021 |
| JP | 2021522019 | A | 8/2021 |
| JP | 7129493 | B2 | 8/2022 |
| JP | 2022554252 | A | 12/2022 |
| JP | 2023532132 | A | 7/2023 |
| KR | 200290061 | Y1 | 9/2002 |
| KR | 20030047451 | A | 6/2003 |
| KR | 20080005516 | A | 1/2008 |
| KR | 20090072069 | A | 7/2009 |
| KR | 20090104426 | A | 10/2009 |
| KR | 20090110359 | A | 10/2009 |
| KR | 101035745 | B1 | 5/2011 |
| KR | 20120005922 | A | 1/2012 |
| KR | 20140039485 | A | 4/2014 |
| KR | 101432639 | B1 | 8/2014 |
| KR | 20180022173 | A | 3/2018 |
| KR | 20180106659 | A | 10/2018 |
| KR | 20180108774 | A | 10/2018 |
| KR | 101976679 | B1 | 5/2019 |
| KR | 101998130 | B1 | 7/2019 |
| KR | 20230034343 | A | 3/2023 |
| PT | 2068717 | E | 6/2013 |
| SE | 505542 | C2 | 9/1997 |
| TW | 408207 | B | 10/2000 |
| TW | 202123903 | A | 7/2021 |
| WO | 8101957 | A1 | 7/1981 |
| WO | 8804558 | A1 | 6/1988 |
| WO | 9104714 | A2 | 4/1991 |
| WO | 9104714 | A3 | 6/1991 |
| WO | 9220299 | A3 | 2/1993 |
| WO | 9303690 | A1 | 3/1993 |
| WO | 9307839 | A1 | 4/1993 |
| WO | 9309736 | A2 | 5/1993 |
| WO | 9309736 | A3 | 6/1993 |
| WO | 9416914 | A1 | 8/1994 |
| WO | 9514448 | A2 | 6/1995 |
| WO | 9600096 | A1 | 1/1996 |
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0025651 | A1 | 5/2000 |
| WO | 0033773 | A1 | 6/2000 |
| WO | 0057784 | A1 | 10/2000 |
| WO | 0069377 | A1 | 11/2000 |
| WO | 0079497 | A1 | 12/2000 |
| WO | 0145618 | A1 | 6/2001 |
| WO | 0145621 | A1 | 6/2001 |
| WO | 02094160 | A1 | 11/2002 |
| WO | 03013967 | A1 | 2/2003 |
| WO | 03015671 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005003725 | A2 | 1/2005 |
| WO | 2005051252 | A1 | 6/2005 |
| WO | 2005060558 | A2 | 7/2005 |
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |

(56) References Cited

FOREIGN PATENT DOCUMENTS

| | | | | |
|---|---|---|---|---|
| WO | 2007128156 A3 | | 2/2008 | |
| WO | 2008026106 A2 | | 3/2008 | |
| WO | 2008078117 A1 | | 7/2008 | |
| WO | 2008104019 A1 | | 9/2008 | |
| WO | 2008141471 A1 | | 11/2008 | |
| WO | 2009004368 A1 | | 1/2009 | |
| WO | 2009004369 A1 | | 1/2009 | |
| WO | 2009052496 A1 | | 4/2009 | |
| WO | 2009052502 A1 | | 4/2009 | |
| WO | 2009007702 A4 | | 7/2009 | |
| WO | 2009101738 A1 | | 8/2009 | |
| WO | 2010058192 A1 | | 5/2010 | |
| WO | 2010030122 A3 | | 7/2010 | |
| WO | 2010101915 A3 | | 1/2011 | |
| WO | 2011018132 A1 | | 2/2011 | |
| WO | 2011018133 A1 | | 2/2011 | |
| WO | 2011024864 A1 | | 3/2011 | |
| WO | 2011054118 A1 | | 5/2011 | |
| WO | 2011079132 A1 | | 6/2011 | |
| WO | 2011107972 A1 | | 9/2011 | |
| WO | 2011108972 A1 | | 9/2011 | |
| WO | 2011117292 A1 | | 9/2011 | |
| WO | 2011123219 A1 | | 10/2011 | |
| WO | 2011132043 A1 | | 10/2011 | |
| WO | 2012012908 A1 | | 2/2012 | |
| WO | 2012020506 A1 | | 2/2012 | |
| WO | 2012065274 A1 | | 5/2012 | |
| WO | 2012097462 A1 | | 7/2012 | |
| WO | 2012098796 A1 | | 7/2012 | |
| WO | 2012101288 A1 | | 8/2012 | |
| WO | 2012175916 A1 | | 12/2012 | |
| WO | 2013018435 A1 | | 2/2013 | |
| WO | 2013033429 A1 | | 3/2013 | |
| WO | 2013055434 A1 | | 4/2013 | |
| WO | 2013082397 A1 | | 6/2013 | |
| WO | 2013103291 A2 | | 7/2013 | |
| WO | 2013131109 A1 | | 9/2013 | |
| WO | 2013167478 A1 | | 11/2013 | |
| WO | 2013177716 A1 | | 12/2013 | |
| WO | 2014041534 A1 | | 3/2014 | |
| WO | 2014046420 A1 | | 3/2014 | |
| WO | 2014118518 A1 | | 8/2014 | |
| WO | 2014160852 A1 | | 10/2014 | |
| WO | 2015023599 A1 | | 2/2015 | |
| WO | 2015052348 A1 | | 4/2015 | |
| WO | 2015068384 A1 | | 5/2015 | |
| WO | 2015169403 A1 | | 11/2015 | |
| WO | 2015170307 A1 | | 11/2015 | |
| WO | 2015197462 A1 | | 12/2015 | |
| WO | 2016051385 A1 | | 4/2016 | |
| WO | 2016055989 A1 | | 4/2016 | |
| WO | 2016071894 A1 | | 5/2016 | |
| WO | 2016103242 A1 | | 6/2016 | |
| WO | 2016116915 A1 | | 7/2016 | |
| WO | 2016124203 A1 | | 8/2016 | |
| WO | 2016139448 A1 | | 9/2016 | |
| WO | 2016166562 A1 | | 10/2016 | |
| WO | 2016167535 A1 | | 10/2016 | |
| WO | 2016191574 A1 | | 12/2016 | |
| WO | 2016200088 A1 | | 12/2016 | |
| WO | 2016200361 A1 | | 12/2016 | |
| WO | 2016204731 A1 | | 12/2016 | |
| WO | 2017001532 A2 | | 1/2017 | |
| WO | 2017075226 A1 | | 5/2017 | |
| WO | 2017100511 A1 | | 6/2017 | |
| WO | 2017152198 A1 | | 9/2017 | |
| WO | 2017153357 A1 | | 9/2017 | |
| WO | 2017162559 A1 | | 9/2017 | |
| WO | 2017205446 A1 | | 11/2017 | |
| WO | 2017209779 A1 | | 12/2017 | |
| WO | WO-2017210524 A1 | * | 12/2017 | ............ A61F 5/455 |
| WO | 2018022414 A1 | | 2/2018 | |
| WO | 2018044781 A1 | | 3/2018 | |
| WO | 2018056953 A1 | | 3/2018 | |
| WO | 2018090550 A1 | | 5/2018 | |
| WO | 2018138513 A1 | | 8/2018 | |
| WO | 2018144318 A1 | | 8/2018 | |
| WO | 2018144463 A1 | | 8/2018 | |
| WO | 2018150263 A1 | | 8/2018 | |
| WO | 2018150268 A1 | | 8/2018 | |
| WO | 2018152156 A1 | | 8/2018 | |
| WO | 2018183791 A1 | | 10/2018 | |
| WO | 2018150267 A3 | | 11/2018 | |
| WO | 2018200721 A1 | | 11/2018 | |
| WO | 2018235026 A1 | | 12/2018 | |
| WO | 2018235065 A1 | | 12/2018 | |
| WO | 2019004404 A1 | | 1/2019 | |
| WO | 2019038732 A1 | | 2/2019 | |
| WO | 2019041005 A1 | | 3/2019 | |
| WO | 2019044217 A1 | | 3/2019 | |
| WO | 2019044218 A1 | | 3/2019 | |
| WO | 2019044219 A1 | | 3/2019 | |
| WO | 2019050959 A1 | | 3/2019 | |
| WO | 2019065541 A1 | | 4/2019 | |
| WO | 2019096845 A1 | | 5/2019 | |
| WO | 2019150385 A1 | | 8/2019 | |
| WO | 2019161094 A1 | | 8/2019 | |
| WO | 2019188566 A1 | | 10/2019 | |
| WO | 2019190593 A1 | | 10/2019 | |
| WO | 2019212949 A1 | | 11/2019 | |
| WO | 2019212950 A1 | | 11/2019 | |
| WO | 2019212951 A1 | | 11/2019 | |
| WO | 2019212952 A1 | | 11/2019 | |
| WO | 2019212954 A1 | | 11/2019 | |
| WO | 2019212955 A1 | | 11/2019 | |
| WO | 2019214787 A1 | | 11/2019 | |
| WO | 2019214788 A1 | | 11/2019 | |
| WO | 2019226826 A1 | | 11/2019 | |
| WO | WO-2019212956 A1 | * | 11/2019 | ............ A61F 5/451 |
| WO | 2019239433 A1 | | 12/2019 | |
| WO | 2020000994 A1 | | 1/2020 | |
| WO | 2020020618 A1 | | 1/2020 | |
| WO | 2020033752 A1 | | 2/2020 | |
| WO | 2020038822 A1 | | 2/2020 | |
| WO | 2020088409 A1 | | 5/2020 | |
| WO | 2020049394 A3 | | 6/2020 | |
| WO | 2020120657 A1 | | 6/2020 | |
| WO | 2020152575 A1 | | 7/2020 | |
| WO | 2020182923 A1 | | 9/2020 | |
| WO | 2020204967 A1 | | 10/2020 | |
| WO | 2020205939 A1 | | 10/2020 | |
| WO | 2020209898 A1 | | 10/2020 | |
| WO | 2020242790 A1 | | 12/2020 | |
| WO | 2020251893 A1 | | 12/2020 | |
| WO | 2020256865 A1 | | 12/2020 | |
| WO | 2021007144 A1 | | 1/2021 | |
| WO | 2021007345 A1 | | 1/2021 | |
| WO | 2021010844 A1 | | 1/2021 | |
| WO | 2021016026 A1 | | 1/2021 | |
| WO | 2021016056 A1 | | 1/2021 | |
| WO | 2021016300 A1 | | 1/2021 | |
| WO | 2021025919 A1 | | 2/2021 | |
| WO | 2021034886 A1 | | 2/2021 | |
| WO | 2021041123 A1 | | 3/2021 | |
| WO | 2021046501 A1 | | 3/2021 | |
| WO | 2021086868 A1 | | 5/2021 | |
| WO | 2021094352 A1 | | 5/2021 | |
| WO | 2021094639 A1 | | 5/2021 | |
| WO | 2021097067 A1 | | 5/2021 | |
| WO | 2021102296 A1 | | 5/2021 | |
| WO | 2021107025 A1 | | 6/2021 | |
| WO | 2021138411 A1 | | 7/2021 | |
| WO | 2021138414 A1 | | 7/2021 | |
| WO | 2021154686 A1 | | 8/2021 | |
| WO | 2021155206 A1 | | 8/2021 | |
| WO | 2021170075 A1 | | 9/2021 | |
| WO | 2021173436 A1 | | 9/2021 | |
| WO | 2021188817 A1 | | 9/2021 | |
| WO | 2021195384 A1 | | 9/2021 | |
| WO | 2021205995 A1 | | 10/2021 | |
| WO | 2021207621 A1 | | 10/2021 | |
| WO | 2021211568 A1 | | 10/2021 | |
| WO | 2021211801 A1 | | 10/2021 | |
| WO | 2021211914 A1 | | 10/2021 | |

(56) References Cited

FOREIGN PATENT DOCUMENTS

| | | | |
|---|---|---|---|
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022029662 | A1 | 2/2022 |
| WO | 2022031943 | A1 | 2/2022 |
| WO | 2022035745 | A1 | 2/2022 |
| WO | 2022051220 | A1 | 3/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150290 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022173803 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2022251184 | A1 | 12/2022 |
| WO | 2022251425 | A1 | 12/2022 |
| WO | 2022271783 | A1 | 12/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023018656 | A1 | 2/2023 |
| WO | 2023018657 | A1 | 2/2023 |
| WO | 2023023777 | A1 | 3/2023 |
| WO | 2023034139 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049156 | A1 | 3/2023 |
| WO | 2023049175 | A1 | 3/2023 |
| WO | 2023086394 | A1 | 5/2023 |
| WO | 2023146529 | A1 | 8/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023163725 | A1 | 8/2023 |
| WO | 2023191764 | A1 | 10/2023 |
| WO | 2023244238 | A1 | 12/2023 |
| WO | 2024043871 | A1 | 2/2024 |
| WO | 2024058788 | A1 | 3/2024 |
| WO | 2024253655 | A1 | 12/2024 |
| WO | 2025034959 | A1 | 2/2025 |
| WO | 2025038087 | A1 | 2/2025 |
| WO | 2025038088 | A1 | 2/2025 |
| WO | 2025048789 | A1 | 3/2025 |
| WO | 2025071622 | A1 | 4/2025 |
| WO | 2025179267 | A1 | 8/2025 |
| WO | 2026035497 | A1 | 2/2026 |

OTHER PUBLICATIONS

Advisory Action for U.S. Appl. No. 16/433,773 mailed Dec. 29, 2023.

Advisory Action for U.S. Appl. No. 16/449,039 mailed Jan. 25, 2024.

Advisory Action for U.S. Appl. No. 16/452,258 mailed Apr. 8, 2024.

Advisory Action for U.S. Appl. No. 16/478,180 mailed Jun. 7, 2024.

Advisory Action for U.S. Appl. No. 16/904,868 mailed Jan. 2, 2024.

Advisory Action for U.S. Appl. No. 17/051,585 mailed Oct. 8, 2024.

Advisory Action for U.S. Appl. No. 17/179,116 mailed Jan. 8, 2024.

Advisory Action for U.S. Appl. No. 17/444,792 mailed Jul. 8, 2024.

Advisory Action for U.S. Appl. No. 17/446,256 mailed Dec. 8, 2023.

Advisory Action for U.S. Appl. No. 17/446,256 mailed Nov. 19, 2024.

Advisory Action for U.S. Appl. No. 17/446,654 mailed Apr. 15, 2024.

Advisory Action for U.S. Appl. No. 17/450,864 mailed Mar. 21, 2024.

Advisory Action for U.S. Appl. No. 17/451,345 mailed Jul. 3, 2024.

Advisory Action for U.S. Appl. No. 17/451,354 mailed Jan. 30, 2024.

Advisory Action for U.S. Appl. No. 17/453,260 mailed Dec. 22, 2023.

Advisory Action for U.S. Appl. No. 17/501,591 mailed Feb. 22, 2024.

Advisory Action for U.S. Appl. No. 17/597,673 mailed Jan. 7, 2025.

Advisory Action for U.S. Appl. No. 17/645,821 mailed Jul. 2, 2024.

Advisory Action for U.S. Appl. No. 17/646,771 mailed Feb. 29, 2024.

Advisory Action for U.S. Appl. No. 17/653,137 mailed Dec. 1, 2023.

Advisory Action for U.S. Appl. No. 17/653,137 mailed Nov. 20, 2024.

Advisory Action for U.S. Appl. No. 17/653,920 mailed Oct. 28, 2024.

Advisory Action for U.S. Appl. No. 17/655,464 mailed Dec. 13, 2023.

Advisory Action for U.S. Appl. No. 17/661,090 mailed Feb. 26, 2024.

Advisory Action for U.S. Appl. No. 17/663,330 mailed Feb. 27, 2024.

Advisory Action for U.S. Appl. No. 17/664,487 mailed Mar. 13, 2024.

Advisory Action for U.S. Appl. No. 17/808,354 mailed Jun. 12, 2024.

Advisory Action for U.S. Appl. No. 18/003,029 mailed Jan. 8, 2025.

Advisory Action for U.S. Appl. No. 18/134,857 mailed Oct. 23, 2024.

Advisory Action for U.S. Appl. No. 18/139,523 mailed Apr. 24, 2024.

Advisory Action for U.S. Appl. No. 18/140,163 mailed Jun. 3, 2024.

Advisory Action for U.S. Appl. No. 18/140,751 mailed Apr. 24, 2024.

Advisory Action for U.S. Appl. No. 18/164,800 mailed Feb. 12, 2024.

Advisory Action for U.S. Appl. No. 18/164,800 mailed Jan. 8, 2025.

Communication of Notice of Opposition of European Application No. 17807547.9 mailed Jan. 5, 2024.

Corrected Notice of Allowability for U.S. Appl. No. 16/369,676 mailed Dec. 7, 2023.

Corrected Notice of Allowability for U.S. Appl. No. 17/326,980 mailed Feb. 8, 2024.

Corrected Notice of Allowability for U.S. Appl. No. 17/450,864 mailed Oct. 24, 2024.

Corrected Notice of Allowability for U.S. Appl. No. 17/501,591 mailed Aug. 9, 2024.

(56) References Cited

OTHER PUBLICATIONS

Corrected Notice of Allowability for U.S. Appl. No. 17/646,771 mailed Jan. 17, 2025.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Corrected Notice of Allowability for U.S. Appl. No. 17/664,914 mailed Aug. 9, 2024.
Corrected Notice of Allowability for U.S. Appl. No. 18/426,795 mailed Dec. 4, 2024.
Final Office Action for U.S. Appl. No. 16/433,773 mailed Sep. 9, 2024.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/452,258 mailed Jan. 6, 2025.
Final Office Action for U.S. Appl. No. 16/478,180 mailed Feb. 28, 2024.
Final Office Action for U.S. Appl. No. 17/051,399 mailed Jan. 8, 2024.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/444,792 mailed Apr. 3, 2024.
Final Office Action for U.S. Appl. No. 17/446,256 mailed Aug. 7, 2024.
Final Office Action for U.S. Appl. No. 17/446,654 mailed Dec. 18, 2024.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/450,864 mailed Dec. 28, 2023.
Final Office Action for U.S. Appl. No. 17/451,345 mailed Apr. 18, 2024.
Final Office Action for U.S. Appl. No. 17/451,354 mailed Oct. 28, 2024.
Final Office Action for U.S. Appl. No. 17/595,747 mailed Dec. 12, 2024.
Final Office Action for U.S. Appl. No. 17/597,673 mailed Oct. 22, 2024.
Final Office Action for U.S. Appl. No. 17/645,821 mailed Apr. 3, 2024.
Final Office Action for U.S. Appl. No. 17/646,771 mailed Dec. 21, 2023.
Final Office Action for U.S. Appl. No. 17/653,137 mailed Aug. 7, 2024.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/661,090 mailed Dec. 11, 2023.
Final Office Action for U.S. Appl. No. 17/663,330 mailed Dec. 12, 2023.
Final Office Action for U.S. Appl. No. 17/664,487 mailed Jan. 13, 2025.
Final Office Action for U.S. Appl. No. 17/664,487 mailed Jan. 4, 2024.
Final Office Action for U.S. Appl. No. 17/808,354 mailed Apr. 10, 2024.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/139,523 mailed Dec. 22, 2023.
Final Office Action for U.S. Appl. No. 18/140,163 mailed Mar. 27, 2024.
Final Office Action for U.S. Appl. No. 18/140,751 mailed Jan. 17, 2024.
Final Office Action for U.S. Appl. No. 18/164,800 mailed Dec. 6, 2023.
Final Office Action for U.S. Appl. No. 18/164,800 mailed Oct. 22, 2024.
International Search Report and Written Opinion from International Application No. PCT/US2023/024805 mailed Dec. 14, 2023.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077208 mailed May 10, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
Issue Notification for U.S. Appl. No. 16/369,676 mailed Oct. 2, 2024.
Issue Notification for U.S. Appl. No. 16/449,039 mailed Jun. 19, 2024.
Issue Notification for U.S. Appl. No. 16/452,145 mailed Oct. 23, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/179,116 mailed Dec. 25, 2024.
Issue Notification for U.S. Appl. No. 17/326,980 mailed Jul. 10, 2024.
Issue Notification for U.S. Appl. No. 17/447,123 mailed Nov. 13, 2024.
Issue Notification for U.S. Appl. No. 17/448,811 mailed Jul. 3, 2024.
Issue Notification for U.S. Appl. No. 17/450,864 mailed Jan. 8, 2025.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/657,474 mailed Jun. 19, 2024.
Issue Notification for U.S. Appl. No. 17/662,700 mailed Oct. 23, 2024.
Issue Notification for U.S. Appl. No. 17/663,046 mailed Dec. 20, 2023.
Issue Notification for U.S. Appl. No. 17/664,914 mailed Nov. 6, 2024.

(56) References Cited

OTHER PUBLICATIONS

Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/198,464 mailed Nov. 20, 2024.
Issue Notification for U.S. Appl. No. 18/299,788 mailed Feb. 21, 2024.
Issue Notification for U.S. Appl. No. 18/389,009 mailed Dec. 18, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 16/904,868 mailed Mar. 12, 2024.
Non-Final Office Action for U.S. Appl. No. 17/051,585 mailed Jan. 8, 2024.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/378,015 mailed Jul. 5, 2024.
Non-Final Office Action for U.S. Appl. No. 17/444,792 mailed Nov. 17, 2023.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/446,256 mailed Feb. 13, 2024.
Non-Final Office Action for U.S. Appl. No. 17/446,654 mailed Jun. 25, 2024.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/450,864 mailed May 29, 2024.
Non-Final Office Action for U.S. Appl. No. 17/451,345 mailed Jan. 17, 2024.
Non-Final Office Action for U.S. Appl. No. 17/451,345 mailed Jul. 25, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/597,673 mailed Mar. 20, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/645,821 mailed Sep. 6, 2024.
Non-Final Office Action for U.S. Appl. No. 17/646,771 mailed Apr. 24, 2024.
Non-Final Office Action for U.S. Appl. No. 17/653,137 mailed Jan. 18, 2024.
Non-Final Office Action for U.S. Appl. No. 17/653,314 mailed Aug. 29, 2024.
Non-Final Office Action for U.S. Appl. No. 17/653,920 mailed Mar. 15, 2024.
Non-Final Office Action for U.S. Appl. No. 17/653,920 mailed Nov. 27, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/664,914 mailed Jan. 31, 2024.
Non-Final Office Action for U.S. Appl. No. 17/749,340 mailed Aug. 14, 2024.
Non-Final Office Action for U.S. Appl. No. 17/757,311 mailed Oct. 22, 2024.
Non-Final Office Action for U.S. Appl. No. 17/758,316 mailed Aug. 28, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/808,354 mailed Nov. 28, 2023.
Non-Final Office Action for U.S. Appl. No. 17/907,125 mailed Dec. 13, 2024.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/139,523 mailed Aug. 26, 2024.
Non-Final Office Action for U.S. Appl. No. 18/140,751 mailed Jun. 21, 2024.
Non-Final Office Action for U.S. Appl. No. 18/164,800 mailed Mar. 22, 2024.
Non-Final Office Action for U.S. Appl. No. 18/198,464 mailed Dec. 7, 2023.
Non-Final Office Action for U.S. Appl. No. 18/389,009 mailed May 24, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 16/478,180 mailed Dec. 16, 2024.
Notice of Allowance for U.S. Appl. No. 16/904,868 mailed Jan. 21, 2025.
Notice of Allowance for U.S. Appl. No. 16/904,868 mailed Sep. 29, 2024.
Notice of Allowance for U.S. Appl. No. 17/051,550 mailed Feb. 7, 2024.
Notice of Allowance for U.S. Appl. No. 17/051,585 mailed Dec. 26, 2024.
Notice of Allowance for U.S. Appl. No. 17/179,116 mailed Sep. 13, 2024.
Notice of Allowance for U.S. Appl. No. 17/326,980 mailed Apr. 5, 2024.
Notice of Allowance for U.S. Appl. No. 17/326,980 mailed Jan. 29, 2024.

(56) References Cited

OTHER PUBLICATIONS

Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/450,864 mailed Sep. 18, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/646,771 mailed Dec. 17, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/661,090 mailed Oct. 30, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 17/663,330 mailed Nov. 20, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Apr. 17, 2024.
Notice of Allowance for U.S. Appl. No. 18/198,464 mailed Jul. 30, 2024.
Notice of Allowance for U.S. Appl. No. 18/389,009 mailed Aug. 28, 2024.
Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/584,002 mailed Jan. 8, 2025.
Restriction Requirement for U.S. Appl. No. 17/527,769 mailed Jun. 17, 2024.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/667,097 mailed Mar. 20, 2024.
Restriction Requirement for U.S. Appl. No. 17/754,736 mailed Nov. 20, 2024.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/013,822, filed Sep. 7, 2020.
U.S. Appl. No. 17/444,792, filed Aug. 10, 2021.
U.S. Appl. No. 18/249,577, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/415,080, filed Jan. 17, 2024.
U.S. Appl. No. 18/426,795, filed Jan. 30, 2024.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 63/564,696, filed Mar. 13, 2024.
U.S. Appl. No. 63/561,893, filed Dec. 11, 2023.
U.S. Appl. No. 63/568,615, filed Mar. 22, 2024.
U.S. Appl. No. 63/608,553, filed Dec. 11, 2023.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, ABUT Definition and Meaning", Dictionary.com, https://www.dictionary.com/browse/abut, 2024, 1 page.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, "Chapter 5 Applications of Polyethylene Oxide (Polyox) in Hydrophilic Matrices", Hydrophilic Matrix Tablets for Oral Controlled Release, AAPS Advances in the Pharmaceutical Sciences vol. 16, 2014, pp. 123-141.
Wikipedia article, "Decibel", https://web.archive.org/web/20200415219 17/https://en.wikipedia/org/wiki/Decibel last accessed Mar. 11, 2024, 21 pages.
Wikipedia article, "Fiberglass" https://web.archive.org.web/20200309194847/https://en.wikipedia.org/wiki/Fiberglass last accessed Mar. 11, 2024.

(56) References Cited

OTHER PUBLICATIONS

Wikipedia article, “Zylinder (Geometrie)”, https://de.wikipedia.org/w/index.php?title=Zylinder(Geometrie)&oldid=154862081, version of Jun. 1, 2016, 7 pages.
Advisory Action for U.S. Appl. No. 17/448,811 mailed Nov. 15, 2023.
Final Office Action for U.S. Appl. No. 17/501,591 mailed Nov. 14, 2023.
Non-Final Office Action for U.S. Appl. No. 16/478,180 mailed Nov. 7, 2023.
Non-Final Office Action for U.S. Appl. No. 18/140,163 mailed Nov. 9, 2023.
Notice of Allowance for U.S. Appl. No. 16/369,676 mailed Nov. 14, 2023.
Notice of Allowance for U.S. Appl. No. 17/662,700 mailed Nov. 15, 2023.
Notice of Allowance for U.S. Appl. No. 18/299,788 mailed Nov. 6, 2023.
U.S. Appl. No. 17/451,719, filed Oct. 19, 2021.
U.S. Appl. No. 18/389,009, filed Nov. 13, 2023.
U.S. Appl. No. 63/596,012, filed Nov. 3, 2023.
Advisory Action for U.S. Appl. No. 17/051,585 mailed Oct. 17, 2023.
Advisory Action for U.S. Appl. No. 17/451,345 mailed Oct. 20, 2023.
Final Office Action for U.S. Appl. No. 16/433,773 mailed Oct. 10, 2023.
Final Office Action for U.S. Appl. No. 16/904,868 mailed Nov. 2, 2023.
Final Office Action for U.S. Appl. No. 17/179,116 mailed Oct. 31, 2023.
Final Office Action for U.S. Appl. No. 17/451,354 mailed Oct. 30, 2023.
Final Office Action for U.S. Appl. No. 17/453,260 mailed Oct. 5, 2023.
International Search Report and Written Opinion from International Application No. PCT/US2023/018474 mailed Sep. 11, 2023.
Issue Notification for U.S. Appl. No. 16/245,726 mailed Oct. 18, 2023.
Issue Notification for U.S. Appl. No. 17/461,036 mailed Oct. 11, 2023.
Non-Final Office Action for U.S. Appl. No. 16/452,145 mailed Nov. 2, 2023.
Non-Final Office Action for U.S. Appl. No. 17/051,550 mailed Oct. 24, 2023.
Non-Final Office Action for U.S. Appl. No. 17/453,560 mailed Oct. 16, 2023.
Non-Final Office Action for U.S. Appl. No. 17/645,821 mailed Oct. 25, 2023.
Notice of Allowance for U.S. Appl. No. 17/051,554 mailed Oct. 18, 2023.
Restriction Requirement for U.S. Appl. No. 18/134,857 mailed Oct. 23, 2023.
U.S. Appl. No. 18/376,274, filed Oct. 3, 2023.
U.S. Appl. No. 18/556,945, filed Oct. 24, 2023.
U.S. Appl. No. 18/558,502, filed Nov. 1, 2023.
“”Advisory Action for U.S. Appl. No. 14/952,591 mailed Jun. 1, 2018.
“”Advisory Action for U.S. Appl. No. 15/238,427 mailed Apr. 10, 2019.
“”Advisory Action for U.S. Appl. No. 16/245,726 mailed Apr. 19, 2023.
“”Advisory Action for U.S. Appl. No. 16/369,676 mailed Mar. 24, 2023.
“”Advisory Action for U.S. Appl. No. 16/433,773 mailed Feb. 15, 2023.
“”Advisory Action for U.S. Appl. No. 16/452,258 mailed Oct. 26, 2022.
“”Advisory Action for U.S. Appl. No. 16/478,180 mailed Sep. 21, 2022.
“”Advisory Action for U.S. Appl. No. 16/478,180 mailed Sep. 7, 2023.
“”Advisory Action for U.S. Appl. No. 16/899,956 mailed Jul. 9, 2021.
“”Advisory Action for U.S. Appl. No. 16/904,868 mailed Jul. 2, 2021.
“”Advisory Action for U.S. Appl. No. 16/904,868 mailed Jun. 15, 2022.
“”Advisory Action for U.S. Appl. No. 16/905,400 mailed Feb. 16, 2022.
“”Advisory Action for U.S. Appl. No. 16/905,400 mailed Jun. 9, 2021.
“”Advisory Action for U.S. Appl. No. 17/051,550 mailed Sep. 8, 2023.
“”Advisory Action for U.S. Appl. No. 17/444,792 mailed Aug. 25, 2023.
“”Advisory Action for U.S. Appl. No. 17/662,700 mailed Jan. 30, 2023.
“”Corrected International Search Report and Written Opinion for International Application No. PCT/US2017/043025 mailed Jan. 11, 2018.
“”Corrected Notice of Allowability for U.S. Appl. No. 15/221,106 mailed Jul. 2, 2019.
“”Corrected Notice of Allowability for U.S. Appl. No. 15/612,325 mailed Mar. 17, 2021.
“”Corrected Notice of Allowability for U.S. Appl. No. 17/330,657 mailed Dec. 9, 2021.
“”Final Office Action for U.S. Appl. No. 14/947,759 mailed Apr. 8, 2016.
“”Final Office Action for U.S. Appl. No. 14/952,591 mailed Feb. 23, 2018.
“”Final Office Action for U.S. Appl. No. 14/952,591 mailed Nov. 1, 2019.
“”Final Office Action for U.S. Appl. No. 14/952,591 mailed Nov. 27, 2020.
“”Final Office Action for U.S. Appl. No. 15/171,968 mailed Feb. 14, 2020.
“”Final Office Action for U.S. Appl. No. 15/171,968 mailed Mar. 19, 2019.
“”Final Office Action for U.S. Appl. No. 15/221,106 mailed Jan. 23, 2019.
“”Final Office Action for U.S. Appl. No. 15/238,427 mailed Jan. 2, 2019.
“”Final Office Action for U.S. Appl. No. 15/260,103 mailed Feb. 14, 2019.
“”Final Office Action for U.S. Appl. No. 15/612,325 mailed Sep. 17, 2020.
“”Final Office Action for U.S. Appl. No. 16/245,726 mailed Nov. 25, 2022.
“”Final Office Action for U.S. Appl. No. 16/369,676 mailed Aug. 31, 2023.
“”Final Office Action for U.S. Appl. No. 16/369,676 mailed Dec. 5, 2022.
“”Final Office Action for U.S. Appl. No. 16/433,773 mailed Oct. 25, 2022.
“”Final Office Action for U.S. Appl. No. 16/449,039 mailed Aug. 1, 2022.
“”Final Office Action for U.S. Appl. No. 16/452,145 mailed Mar. 25, 2022.
“”Final Office Action for U.S. Appl. No. 16/452,258 mailed Jun. 14, 2022.
“”Final Office Action for U.S. Appl. No. 16/478,180 mailed Jun. 22, 2022.
“”Final Office Action for U.S. Appl. No. 16/478,180 mailed May 31, 2023.
“”Final Office Action for U.S. Appl. No. 16/899,956 mailed Apr. 19, 2021.
“”Final Office Action for U.S. Appl. No. 16/904,868 mailed Mar. 10, 2022.
“”Final Office Action for U.S. Appl. No. 16/904,868 mailed Mar. 26, 2021.
“”Final Office Action for U.S. Appl. No. 16/905,400 mailed Apr. 6, 2021.

(56) References Cited

OTHER PUBLICATIONS

“”Final Office Action for U.S. Appl. No. 16/905,400 mailed Dec. 9, 2021.
“”Final Office Action for U.S. Appl. No. 17/051,399 mailed Mar. 9, 2023.
“”Final Office Action for U.S. Appl. No. 17/051,550 mailed May 23, 2023.
“”Final Office Action for U.S. Appl. No. 17/051,585 mailed Jul. 27, 2023.
“”Final Office Action for U.S. Appl. No. 17/088,272 mailed May 25, 2021.
“”Final Office Action for U.S. Appl. No. 17/444,792 mailed Jun. 15, 2023.
“”Final Office Action for U.S. Appl. No. 17/446,256 mailed Sep. 19, 2023.
“”Final Office Action for U.S. Appl. No. 17/448,811 mailed Aug. 3, 2023.
“”Final Office Action for U.S. Appl. No. 17/451,345 mailed May 3, 2023.
“”Final Office Action for U.S. Appl. No. 17/653,137 mailed Sep. 21, 2023.
“”Final Office Action for U.S. Appl. No. 17/655,464 mailed Sep. 1, 2023.
“”Final Office Action for U.S. Appl. No. 17/662,700 mailed Sep. 30, 2022.
“”Final Office Action for U.S. Appl. No. 29/624,661 mailed Feb. 18, 2020.
“”International Search Report and Written Opinion from International Application No. PCT/IB2021/057173 mailed Nov. 5, 2021.
“”International Search Report and Written Opinion from International Application No. PCT/US2016/049274 mailed Dec. 1, 2016.
“”International Search Report and Written Opinion from International Application No. PCT/US2017/035625 mailed Aug. 15, 2017.
“”International Search Report and Written Opinion from International Application No. PCT/US2017/043025 mailed Oct. 18, 2017.
“”International Search Report and Written Opinion from International Application No. PCT/US2018/015968 mailed Apr. 6, 2018.
“”International Search Report and Written Opinion from International Application No. PCT/US2019/029608 mailed Sep. 3, 2019.
“”International Search Report and Written Opinion from International Application No. PCT/US2019/029609 mailed Sep. 3, 2019.
“”International Search Report and Written Opinion from International Application No. PCT/US2019/029610 mailed Sep. 3, 2019.
“”International Search Report and Written Opinion from International Application No. PCT/US2019/029611 mailed Jul. 3, 2019.
“”International Search Report and Written Opinion from International Application No. PCT/US2019/029613 mailed Jul. 3, 2019.
“”International Search Report and Written Opinion from International Application No. PCT/US2019/029614 mailed Sep. 26, 2019.
“”International Search Report and Written Opinion from International Application No. PCT/US2019/029616 mailed Aug. 30, 2019.
“”International Search Report and Written Opinion from International Application No. PCT/US2020/023572 mailed Jul. 6, 2020.
“”International Search Report and Written Opinion from International Application No. PCT/US2020/033064 mailed Aug. 31, 2020.
“”International Search Report and Written Opinion from International Application No. PCT/US2020/033122 mailed Aug. 31, 2020.
“”International Search Report and Written Opinion from International Application No. PCT/US2020/040860 mailed Oct. 2, 2020.
“”International Search Report and Written Opinion from International Application No. PCT/US2020/041242 mailed Nov. 17, 2020.
“”International Search Report and Written Opinion from International Application No. PCT/US2020/041249 mailed Oct. 2, 2020.
“”International Search Report and Written Opinion from International Application No. PCT/US2020/042262 mailed Oct. 14, 2020.
“”International Search Report and Written Opinion from International Application No. PCT/US2020/043059 mailed Oct. 6, 2020.
“”International Search Report and Written Opinion from International Application No. PCT/US2020/044024 mailed Nov. 12, 2020.
“”International Search Report and Written Opinion from International Application No. PCT/US2020/046914 mailed Dec. 1, 2020.
“”International Search Report and Written Opinion from International Application No. PCT/US2020/055680 mailed Dec. 15, 2020.
“”International Search Report and Written Opinion from International Application No. PCT/US2020/057562 mailed Jan. 27, 2021.
“”International Search Report and Written Opinion from International Application No. PCT/US2020/061563 mailed Feb. 19, 2021.
“”International Search Report and Written Opinion from International Application No. PCT/US2020/065234 mailed Apr. 12, 2021.
“”International Search Report and Written Opinion from International Application No. PCT/US2020/067451 mailed Mar. 25, 2021.
“”International Search Report and Written Opinion from International Application No. PCT/US2020/067454 mailed Mar. 29, 2021.
“”International Search Report and Written Opinion from International Application No. PCT/US2020/067455 mailed Mar. 26, 2021.
“”International Search Report and Written Opinion from International Application No. PCT/US2021/015024 mailed May 18, 2021.
“”International Search Report and Written Opinion from International Application No. PCT/US2021/015787 mailed May 27, 2021.
“”International Search Report and Written Opinion from International Application No. PCT/US2021/023001 mailed Jun. 21, 2021.
“”International Search Report and Written Opinion from International Application No. PCT/US2021/024162 mailed Jul. 8, 2021.
“”International Search Report and Written Opinion from International Application No. PCT/US2021/026607 mailed Jul. 29, 2021.
“”International Search Report and Written Opinion from International Application No. PCT/US2021/027061 mailed Jul. 19, 2021.
“”International Search Report and Written Opinion from International Application No. PCT/US2021/027104 mailed Jul. 6, 2021.
“”International Search Report and Written Opinion from International Application No. PCT/US2021/027314 mailed Jul. 6, 2021.
“”International Search Report and Written Opinion from International Application No. PCT/US2021/027422 mailed Aug. 12, 2021.
“”International Search Report and Written Opinion from International Application No. PCT/US2021/027425 mailed Aug. 11, 2021.
“”International Search Report and Written Opinion from International Application No. PCT/US2021/027913 mailed Jul. 12, 2021.
“”International Search Report and Written Opinion from International Application No. PCT/US2021/027917 mailed Aug. 19, 2021.
“”International Search Report and Written Opinion from International Application No. PCT/US2021/039866 mailed Oct. 7, 2021.
“”International Search Report and Written Opinion from International Application No. PCT/US2021/043893 mailed Nov. 22, 2021.
“”International Search Report and Written Opinion from International Application No. PCT/US2021/044699 mailed Nov. 22, 2021.
“”International Search Report and Written Opinion from International Application No. PCT/US2021/045188 mailed Jan. 26, 2022.
“”International Search Report and Written Opinion from International Application No. PCT/US2021/047536 mailed Dec. 23, 2021.
“”International Search Report and Written Opinion from International Application No. PCT/US2021/048211 mailed Dec. 22, 2021.
“”International Search Report and Written Opinion from International Application No. PCT/US2021/048661 mailed Feb. 14, 2022.
“”International Search Report and Written Opinion from International Application No. PCT/US2021/049404 mailed Jan. 18, 2022.
“”International Search Report and Written Opinion from International Application No. PCT/US2021/051456 mailed Jan. 19, 2022.
“”International Search Report and Written Opinion from International Application No. PCT/US2021/053593 mailed Apr. 11, 2022.
“”International Search Report and Written Opinion from International Application No. PCT/US2021/055515 mailed Jan. 28, 2022.
“”International Search Report and Written Opinion from International Application No. PCT/US2021/056566 mailed Feb. 11, 2022.
“”International Search Report and Written Opinion from International Application No. PCT/US2021/060993 mailed Mar. 18, 2022.
“”International Search Report and Written Opinion from International Application No. PCT/US2021/062440 mailed Mar. 28, 2022.
“”International Search Report and Written Opinion from International Application No. PCT/US2022/011108 mailed Apr. 22, 2022.
“”International Search Report and Written Opinion from International Application No. PCT/US2022/011281 mailed Apr. 25, 2022.

(56) References Cited

OTHER PUBLICATIONS

""International Search Report and Written Opinion from International Application No. PCT/US2022/011419 mailed Jun. 7, 2022.
""International Search Report and Written Opinion from International Application No. PCT/US2022/011421 mailed Jun. 13, 2022.
""International Search Report and Written Opinion from International Application No. PCT/US2022/012794 mailed May 3, 2022.
""International Search Report and Written Opinion from International Application No. PCT/US2022/014285 mailed Sep. 28, 2022.
""International Search Report and Written Opinion from International Application No. PCT/US2022/014749 mailed Sep. 28, 2022.
""International Search Report and Written Opinion from International Application No. PCT/US2022/015026 mailed Oct. 31, 2022.
""International Search Report and Written Opinion from International Application No. PCT/US2022/015045 mailed Sep. 9, 2022.
""International Search Report and Written Opinion from International Application No. PCT/US2022/015073 mailed Sep. 8, 2022.
""International Search Report and Written Opinion from International Application No. PCT/US2022/015418 mailed Nov. 11, 2022.
""International Search Report and Written Opinion from International Application No. PCT/US2022/015420 mailed Nov. 18, 2022.
""International Search Report and Written Opinion from International Application No. PCT/US2022/015471 mailed May 16, 2022.
""International Search Report and Written Opinion from International Application No. PCT/US2022/015492 mailed Apr. 26, 2022.
""International Search Report and Written Opinion from International Application No. PCT/US2022/015781 mailed May 6, 2022.
""International Search Report and Written Opinion from International Application No. PCT/US2022/016942 mailed Jun. 8, 2022.
""International Search Report and Written Opinion from International Application No. PCT/US2022/018159 mailed Dec. 12, 2022.
""International Search Report and Written Opinion from International Application No. PCT/US2022/018170 mailed May 31, 2022.
""International Search Report and Written Opinion from International Application No. PCT/US2022/019254 mailed Jun. 7, 2022.
""International Search Report and Written Opinion from International Application No. PCT/US2022/019480 mailed Jun. 13, 2022.
""International Search Report and Written Opinion from International Application No. PCT/US2022/021103 mailed Jun. 23, 2022.
""International Search Report and Written Opinion from International Application No. PCT/US2022/022111 mailed Oct. 26, 2022.
""International Search Report and Written Opinion from International Application No. PCT/US2022/023594 mailed Jul. 12, 2022.
""International Search Report and Written Opinion from International Application No. PCT/US2022/026667 mailed Aug. 22, 2022.
""International Search Report and Written Opinion from International Application No. PCT/US2022/030685 mailed Oct. 31, 2022.
""International Search Report and Written Opinion from International Application No. PCT/US2022/031032 mailed Sep. 9, 2022.
""International Search Report and Written Opinion from International Application No. PCT/US2022/032424 mailed Oct. 11, 2022.
""International Search Report and Written Opinion from International Application No. PCT/US2022/034457 mailed Oct. 12, 2022.
""International Search Report and Written Opinion from International Application No. PCT/US2022/034744 mailed Dec. 9, 2022.
""International Search Report and Written Opinion from International Application No. PCT/US2022/039018 mailed Jan. 10, 2023.
""International Search Report and Written Opinion from International Application No. PCT/US2022/039022 mailed Jan. 10, 2023.
""International Search Report and Written Opinion from International Application No. PCT/US2022/039711 mailed Jan. 12, 2023.
""International Search Report and Written Opinion from International Application No. PCT/US2022/039714 mailed Nov. 22, 2022.
""International Search Report and Written Opinion from International Application No. PCT/US2022/041085 mailed Mar. 16, 2023.
""International Search Report and Written Opinion from International Application No. PCT/US2022/041688 mailed Nov. 21, 2022.
""International Search Report and Written Opinion from International Application No. PCT/US2022/042719 mailed Dec. 5, 2022.
""International Search Report and Written Opinion from International Application No. PCT/US2022/042725 mailed Dec. 19, 2022.
""International Search Report and Written Opinion from International Application No. PCT/US2022/043818 mailed Mar. 24, 2023.
""International Search Report and Written Opinion from International Application No. PCT/US2022/044107 mailed Dec. 23, 2022.
""International Search Report and Written Opinion from International Application No. PCT/US2022/044208 mailed May 8, 2023.
""International Search Report and Written Opinion from International Application No. PCT/US2022/044212 mailed Jan. 20, 2023.
""International Search Report and Written Opinion from International Application No. PCT/US2022/044243 mailed Feb. 24, 2023.
""International Search Report and Written Opinion from International Application No. PCT/US2022/049300 mailed Jun. 6, 2023.
""International Search Report and Written Opinion from International Application No. PCT/US2022/050909 mailed Jul. 24, 2023.
""International Search Report and Written Opinion from International Application No. PCT/US2023/012696 mailed Jul. 6, 2023.
""Issue Notification for U.S. Appl. No. 14/952,591 mailed Jul. 28, 2021.
""Issue Notification for U.S. Appl. No. 15/171,968 mailed Mar. 3, 2021.
""Issue Notification for U.S. Appl. No. 15/221,106 mailed Jul. 24, 2019.
""Issue Notification for U.S. Appl. No. 15/238,427 mailed Jul. 24, 2019.
""Issue Notification for U.S. Appl. No. 15/260,103 mailed Aug. 7, 2019.
""Issue Notification for U.S. Appl. No. 15/611,587 mailed Feb. 20, 2019.
""Issue Notification for U.S. Appl. No. 15/612,325 mailed Mar. 24, 2021.
""Issue Notification for U.S. Appl. No. 16/899,956 mailed Mar. 29, 2023.
""Issue Notification for U.S. Appl. No. 16/905,400 mailed Nov. 30, 2022.
""Issue Notification for U.S. Appl. No. 17/088,272 mailed Jun. 15, 2022.
""Issue Notification for U.S. Appl. No. 17/330,657 mailed Jun. 22, 2022.
""Issue Notification for U.S. Appl. No. 29/624,661 mailed Aug. 4, 2021.
""Non-Final Office Action for U.S. Appl. No. 14/947,759 mailed Mar. 17, 2016.
""Non-Final Office Action for U.S. Appl. No. 14/952,591 mailed Aug. 1, 2017.
""Non-Final Office Action for U.S. Appl. No. 14/952,591 mailed Mar. 20, 2020.
""Non-Final Office Action for U.S. Appl. No. 14/952,591 mailed Mar. 21, 2019.
""Non-Final Office Action for U.S. Appl. No. 14/952,591 mailed Sep. 28, 2018.
""Non-Final Office Action for U.S. Appl. No. 15/171,968 mailed May 11, 2020.
""Non-Final Office Action for U.S. Appl. No. 15/171,968 mailed Aug. 20, 2019.
""Non-Final Office Action for U.S. Appl. No. 15/171,968 mailed Jun. 12, 2018.
""Non-Final Office Action for U.S. Appl. No. 15/221,106 mailed Jun. 5, 2018.
""Non-Final Office Action for U.S. Appl. No. 15/238,427 mailed Aug. 8, 2018.
""Non-Final Office Action for U.S. Appl. No. 15/260,103 mailed Sep. 26, 2018.
""Non-Final Office Action for U.S. Appl. No. 15/611,587 mailed Dec. 29, 2017.
""Non-Final Office Action for U.S. Appl. No. 15/611,587 mailed Jul. 13, 2018.
""Non-Final Office Action for U.S. Appl. No. 15/612,325 mailed Mar. 19, 2020.
""Non-Final Office Action for U.S. Appl. No. 16/245,726 mailed Jan. 21, 2022.

(56) References Cited

OTHER PUBLICATIONS

""Non-Final Office Action for U.S. Appl. No. 16/369,676 mailed Mar. 31, 2022.
""Non-Final Office Action for U.S. Appl. No. 16/433,773 mailed Apr. 11, 2023.
""Non-Final Office Action for U.S. Appl. No. 16/433,773 mailed Apr. 21, 2022.
""Non-Final Office Action for U.S. Appl. No. 16/449,039 mailed Apr. 27, 2023.
""Non-Final Office Action for U.S. Appl. No. 16/449,039 mailed Dec. 8, 2021.
""Non-Final Office Action for U.S. Appl. No. 16/452,145 mailed Mar. 28, 2023.
""Non-Final Office Action for U.S. Appl. No. 16/452,145 mailed Sep. 28, 2021.
""Non-Final Office Action for U.S. Appl. No. 16/452,258 mailed Apr. 26, 2023.
""Non-Final Office Action for U.S. Appl. No. 16/452,258 mailed Sep. 28, 2021.
""Non-Final Office Action for U.S. Appl. No. 16/478,180 mailed Dec. 20, 2022.
""Non-Final Office Action for U.S. Appl. No. 16/478,180 mailed Oct. 22, 2021.
""Non-Final Office Action for U.S. Appl. No. 16/899,956 mailed Oct. 16, 2020.
""Non-Final Office Action for U.S. Appl. No. 16/899,956 mailed Sep. 2, 2021.
""Non-Final Office Action for U.S. Appl. No. 16/904,868 mailed Mar. 15, 2023.
""Non-Final Office Action for U.S. Appl. No. 16/904,868 mailed Nov. 25, 2020.
""Non-Final Office Action for U.S. Appl. No. 16/904,868 mailed Oct. 5, 2021.
""Non-Final Office Action for U.S. Appl. No. 16/905,400 mailed Apr. 27, 2022.
""Non-Final Office Action for U.S. Appl. No. 16/905,400 mailed Dec. 2, 2020.
""Non-Final Office Action for U.S. Appl. No. 16/905,400 mailed Jul. 22, 2021.
""Non-Final Office Action for U.S. Appl. No. 17/051,399 mailed Aug. 18, 2023.
""Non-Final Office Action for U.S. Appl. No. 17/051,550 mailed Dec. 15, 2022.
""Non-Final Office Action for U.S. Appl. No. 17/051,585 mailed Mar. 29, 2023.
""Non-Final Office Action for U.S. Appl. No. 17/088,272 mailed Jan. 25, 2021.
""Non-Final Office Action for U.S. Appl. No. 17/179,116 mailed Mar. 24, 2023.
""Non-Final Office Action for U.S. Appl. No. 17/326,980 mailed Jul. 11, 2023.
""Non-Final Office Action for U.S. Appl. No. 17/330,657 mailed Aug. 11, 2021.
""Non-Final Office Action for U.S. Appl. No. 17/444,792 mailed Feb. 10, 2023.
""Non-Final Office Action for U.S. Appl. No. 17/446,256 mailed Apr. 13, 2023.
""Non-Final Office Action for U.S. Appl. No. 17/446,654 mailed Sep. 8, 2023.
""Non-Final Office Action for U.S. Appl. No. 17/448,811 mailed Mar. 1, 2023.
""Non-Final Office Action for U.S. Appl. No. 17/450,864 mailed May 10, 2023.
""Non-Final Office Action for U.S. Appl. No. 17/451,345 mailed Dec. 7, 2022.
""Non-Final Office Action for U.S. Appl. No. 17/451,354 mailed May 3, 2023.
""Non-Final Office Action for U.S. Appl. No. 17/453,260 mailed Mar. 14, 2023.
""Non-Final Office Action for U.S. Appl. No. 17/501,591 mailed Apr. 25, 2023.
""Non-Final Office Action for U.S. Appl. No. 17/646,771 mailed Jul. 5, 2023.
""Non-Final Office Action for U.S. Appl. No. 17/653,137 mailed Apr. 7, 2023.
""Non-Final Office Action for U.S. Appl. No. 17/655,464 mailed Mar. 14, 2023.
""Non-Final Office Action for U.S. Appl. No. 17/657,474 mailed Sep. 12, 2023.
""Non-Final Office Action for U.S. Appl. No. 17/661,090 mailed Jul. 6, 2023.
""Non-Final Office Action for U.S. Appl. No. 17/662,700 mailed Jul. 22, 2022.
""Non-Final Office Action for U.S. Appl. No. 17/663,330 mailed Jun. 29, 2023.
""Non-Final Office Action for U.S. Appl. No. 17/664,487 mailed Jun. 8, 2023.
""Non-Final Office Action for U.S. Appl. No. 18/139,523 mailed Aug. 17, 2023.
""Non-Final Office Action for U.S. Appl. No. 18/140,751 mailed Sep. 14, 2023.
""Non-Final Office Action for U.S. Appl. No. 29/624,661 mailed Jul. 18, 2019.
""Non-Final Office Action for U.S. Appl. No. 29/694,002 mailed Jun. 24, 2020.
""Non-Final Office Action for U.S. Appl. No. 29/741,751 mailed Jan. 18, 2022.
""Notice of Allowance for U.S. Appl. No. 14/952,591 mailed Apr. 5, 2021.
""Notice of Allowance for U.S. Appl. No. 14/952,591 mailed Jul. 8, 2021.
""Notice of Allowance for U.S. Appl. No. 15/171,968 mailed Feb. 16, 2021.
""Notice of Allowance for U.S. Appl. No. 15/171,968 mailed Nov. 6, 2020.
""Notice of Allowance for U.S. Appl. No. 15/221,106 mailed May 1, 2019.
""Notice of Allowance for U.S. Appl. No. 15/238,427 mailed May 23, 2019.
""Notice of Allowance for U.S. Appl. No. 15/260,103 mailed Jun. 7, 2019.
""Notice of Allowance for U.S. Appl. No. 15/611,587 mailed Dec. 21, 2018.
""Notice of Allowance for U.S. Appl. No. 15/612,325 mailed Feb. 19, 2021.
""Notice of Allowance for U.S. Appl. No. 15/612,325 mailed Jan. 21, 2021.
""Notice of Allowance for U.S. Appl. No. 16/245,726 mailed Jul. 6, 2023.
""Notice of Allowance for U.S. Appl. No. 16/449,039 mailed Dec. 15, 2022.
""Notice of Allowance for U.S. Appl. No. 16/899,956 mailed Apr. 19, 2022.
""Notice of Allowance for U.S. Appl. No. 16/899,956 mailed Aug. 10, 2022.
""Notice of Allowance for U.S. Appl. No. 16/899,956 mailed Dec. 1, 2022.
""Notice of Allowance for U.S. Appl. No. 16/899,956 mailed Dec. 29, 2021.
""Notice of Allowance for U.S. Appl. No. 16/905,400 mailed Aug. 17, 2022.
""Notice of Allowance for U.S. Appl. No. 17/051,554 mailed Jul. 6, 2023.
""Notice of Allowance for U.S. Appl. No. 17/088,272 mailed Aug. 5, 2021.
""Notice of Allowance for U.S. Appl. No. 17/088,272 mailed Mar. 4, 2022.
""Notice of Allowance for U.S. Appl. No. 17/088,272 mailed Nov. 24, 2021.
""Notice of Allowance for U.S. Appl. No. 17/330,657 mailed Mar. 16, 2022.

(56) References Cited

OTHER PUBLICATIONS

“”Notice of Allowance for U.S. Appl. No. 17/330,657 mailed Nov. 26, 2021.
“”Notice of Allowance for U.S. Appl. No. 17/461,036 mailed Feb. 22, 2023.
“”Notice of Allowance for U.S. Appl. No. 17/461,036 mailed Jun. 30, 2023.
“”Notice of Allowance for U.S. Appl. No. 17/461,036 mailed Oct. 6, 2022.
“”Notice of Allowance for U.S. Appl. No. 17/662,700 mailed Jul. 28, 2023.
“”Notice of Allowance for U.S. Appl. No. 17/662,700 mailed Mar. 28, 2023.
“”Notice of Allowance for U.S. Appl. No. 17/663,046 mailed Jan. 30, 2023.
“”Notice of Allowance for U.S. Appl. No. 18/299,788 mailed Jul. 24, 2023.
“”Notice of Allowance for U.S. Appl. No. 29/624,661 mailed Apr. 28, 2021.
“”Notice of Allowance for U.S. Appl. No. 29/624,661 mailed Jul. 10, 2020.
“”Notice of Allowance for U.S. Appl. No. 29/624,661 mailed May 14, 2020.
“”Notice of Allowance for U.S. Appl. No. 29/624,661 mailed Sep. 29, 2020.
“”Notice of Allowance for U.S. Appl. No. 29/694,002 mailed Apr. 29, 2021.
“”Notice of Allowance for U.S. Appl. No. 29/694,002 mailed Jan. 29, 2021.
“”Notice of Allowance for U.S. Appl. No. 29/694,002 mailed Oct. 16, 2020.
“”Notice of Allowance for U.S. Appl. No. 29/741,751 mailed Jun. 9, 2022.
“”Notice to File Missing Parts for U.S. Appl. No. 17/179,116 mailed Mar. 3, 2021.
“”Restriction Requirement for U.S. Appl. No. 16/433,773 mailed Dec. 7, 2021.
“”Restriction Requirement for U.S. Appl. No. 16/478,180 mailed May 25, 2021.
“”Restriction Requirement for U.S. Appl. No. 17/051,600 mailed Sep. 21, 2023.
“”Restriction Requirement for U.S. Appl. No. 17/326,980 mailed Mar. 20, 2023.
“”Restriction Requirement for U.S. Appl. No. 17/446,256 mailed Jan. 23, 2023.
“”Restriction Requirement for U.S. Appl. No. 17/645,821 mailed Jul. 12, 2023.
“”Restriction Requirement for U.S. Appl. No. 17/646,771 mailed Apr. 6, 2023.
“”Restriction Requirement for U.S. Appl. No. 17/657,474 mailed Jun. 30, 2023.
“”Text Messages to Lorena Eckert Re Prototype PureWick Holder dated Apr. 16, 2022.
“”U.S. Appl. No. 14/625,469, filed Feb. 28, 2015.
“”U.S. Appl. No. 14/947,759, filed Nov. 20, 2015.
“”U.S. Appl. No. 14/952,591, filed Nov. 25, 2015.
“”U.S. Appl. No. 15/171,968, filed Jun. 2, 2016.
“”U.S. Appl. No. 15/221,106, filed Jul. 27, 2016.
“”U.S. Appl. No. 15/260,103, filed Sep. 8, 2016.
“”U.S. Appl. No. 15/384,196, filed Dec. 19, 2016.
“”U.S. Appl. No. 15/611,587, filed Jun. 1, 2017.
“”U.S. Appl. No. 15/612,325, filed Jun. 2, 2017.
“”U.S. Appl. No. 16/245,726, filed Jan. 11, 2019.
“”U.S. Appl. No. 16/369,676, filed Mar. 29, 2019.
“”U.S. Appl. No. 16/433,773, filed Jun. 6, 2019.
“”U.S. Appl. No. 16/449,039, filed Jun. 21, 2019.
“”U.S. Appl. No. 16/452,145, filed Jun. 25, 2019.
“”U.S. Appl. No. 16/452,258, filed Jun. 25, 2019.
“”U.S. Appl. No. 16/478,180, filed Jul. 16, 2019.
“”U.S. Appl. No. 16/904,868, filed Jun. 18, 2020.
“”U.S. Appl. No. 16/905,400, filed Jun. 18, 2020.
“”U.S. Appl. No. 17/051,550, filed Oct. 29, 2020.
“”U.S. Appl. No. 17/051,554, filed Oct. 29, 2020.
“”U.S. Appl. No. 17/051,585, filed Oct. 29, 2020.
“”U.S. Appl. No. 17/051,600, filed Oct. 29, 2020.
“”U.S. Appl. No. 17/088,272, filed Nov. 3, 2020.
“”U.S. Appl. No. 17/179,116, filed Feb. 18, 2021.
“”U.S. Appl. No. 17/330,657, filed May 26, 2021.
“”U.S. Appl. No. 17/378,015, filed Jul. 16, 2021.
“”U.S. Appl. No. 17/394,055, filed Aug. 4, 2021.
“”U.S. Appl. No. 17/444,825, filed Aug. 10, 2021.
“”U.S. Appl. No. 17/446,256, filed Aug. 27, 2021.
“”U.S. Appl. No. 17/446,654, filed Sep. 1, 2021.
“”U.S. Appl. No. 17/447,123, filed Sep. 8, 2021.
“”U.S. Appl. No. 17/450,864, filed Oct. 14, 2021.
“”U.S. Appl. No. 17/451,345, filed Oct. 19, 2021.
“”U.S. Appl. No. 17/451,354, filed Oct. 19, 2021.
“”U.S. Appl. No. 17/453,260, filed Nov. 2, 2021.
“”U.S. Appl. No. 17/453,560, filed Nov. 4, 2021.
“”U.S. Appl. No. 17/461,036 mailed Aug. 30, 2021.
“”U.S. Appl. No. 17/501,591, filed Oct. 14, 2021.
“”U.S. Appl. No. 17/595,747, filed Nov. 23, 2021.
“”U.S. Appl. No. 17/597,408, filed Jan. 5, 2022.
“”U.S. Appl. No. 17/597,673, filed Jan. 18, 2022.
“”U.S. Appl. No. 17/614,173, filed Nov. 24, 2021.
“”U.S. Appl. No. 17/631,619, filed Jan. 31, 2022.
“”U.S. Appl. No. 17/645,821, filed Dec. 23, 2021.
“”U.S. Appl. No. 17/646,771, filed Jan. 3, 2022.
“”U.S. Appl. No. 17/653,314, filed Mar. 3, 2022.
“”U.S. Appl. No. 17/653,920, filed Mar. 8, 2022.
“”U.S. Appl. No. 17/655,464, filed Mar. 18, 2022.
“”U.S. Appl. No. 17/657,474, filed Mar. 31, 2022.
“”U.S. Appl. No. 17/661,090, filed Apr. 28, 2022.
“”U.S. Appl. No. 17/662,700, filed May 10, 2022.
“”U.S. Appl. No. 17/663,046, filed May 12, 2022.
“”U.S. Appl. No. 17/664,487, filed May 23, 2022.
“”U.S. Appl. No. 17/664,914, filed May 25, 2022.
“”U.S. Appl. No. 17/749,340, filed May 20, 2022.
“”U.S. Appl. No. 17/754,736, filed Apr. 11, 2022.
“”U.S. Appl. No. 17/756,201, filed May 19, 2022.
“”U.S. Appl. No. 17/758,152, filed Jun. 29, 2022.
“”U.S. Appl. No. 17/758,316, filed Jul. 1, 2022.
“”U.S. Appl. No. 17/759,697, filed Jul. 28, 2022.
“”U.S. Appl. No. 17/878,268, filed Aug. 1, 2022.
“”U.S. Appl. No. 17/907,125, filed Sep. 23, 2022.
“”U.S. Appl. No. 17/912,147, filed Sep. 16, 2022.
“”U.S. Appl. No. 17/929,887, filed Sep. 6, 2022.
“”U.S. Appl. No. 17/930,238, filed Sep. 7, 2022.
“”U.S. Appl. No. 17/933,590, filed Sep. 20, 2022.
“”U.S. Appl. No. 17/996,064, filed Oct. 12, 2022.
“”U.S. Appl. No. 17/996,155, filed Oct. 13, 2022.
“”U.S. Appl. No. 17/996,253, filed Oct. 14, 2022.
“”U.S. Appl. No. 17/996,468, filed Oct. 18, 2022.
“”U.S. Appl. No. 17/996,556, filed Oct. 19, 2022.
“”U.S. Appl. No. 18/003,029, filed Dec. 22, 2022.
“”U.S. Appl. No. 18/006,807, filed Jan. 25, 2023.
“”U.S. Appl. No. 18/007,105, filed Jan. 27, 2023.
“”U.S. Appl. No. 18/041,109, filed Feb. 9, 2023.
“”U.S. Appl. No. 18/042,842, filed Feb. 24, 2023.
“”U.S. Appl. No. 18/043,618, filed Mar. 1, 2023.
“”U.S. Appl. No. 18/115,444, filed Feb. 28, 2023.
“”U.S. Appl. No. 18/134,857, filed Apr. 14, 2023.
“”U.S. Appl. No. 18/140,163, filed Apr. 27, 2023.
“”U.S. Appl. No. 18/140,751, filed Apr. 28, 2023.
“”U.S. Appl. No. 18/164,800, filed Feb. 6, 2023.
“”U.S. Appl. No. 18/198,464, filed May 17, 2023.
“”U.S. Appl. No. 18/246,121, filed Mar. 21, 2023.
“”U.S. Appl. No. 18/247,986, filed Apr. 5, 2023.
“”U.S. Appl. No. 18/259,626, filed Jun. 28, 2023.
“”U.S. Appl. No. 18/260,122, filed Jun. 30, 2023.
“”U.S. Appl. No. 18/260,391, filed Jul. 5, 2023.
“”U.S. Appl. No. 18/260,394, filed Jul. 5, 2023.
“”U.S. Appl. No. 18/263,800, filed Aug. 1, 2023.

(56) References Cited

OTHER PUBLICATIONS

""U.S. Appl. No. 18/264,004, filed Aug. 2, 2023.
""U.S. Appl. No. 18/265,736, filed Jun. 7, 2023.
""U.S. Appl. No. 18/299,788, filed Apr. 13, 2023.
""U.S. Appl. No. 18/335,579, filed Jun. 15, 2023.
""U.S. Appl. No. 18/373,424, filed Sep. 27, 2023.
""U.S. Appl. No. 18/548,152, filed Aug. 28, 2023.
""U.S. Appl. No. 18/549,387, filed Sep. 7, 2023.
""U.S. Appl. No. 18/549,658, filed Sep. 8, 2023.
""U.S. Appl. No. 29/741,751, filed Jul. 15, 2020.
""U.S. Appl. No. 61/955,537, filed Mar. 19, 2014.
""U.S. Appl. No. 62/082,279, filed Nov. 20, 2014.
""U.S. Appl. No. 62/084,078, filed Nov. 25, 2014.
""U.S. Appl. No. 62/414,963, filed Oct. 31, 2016.
""U.S. Appl. No. 62/452,437, filed Jan. 31, 2017.
""U.S. Appl. No. 62/485,578, filed Apr. 14, 2017.
""U.S. Appl. No. 62/665,297, filed May 1, 2018.
""U.S. Appl. No. 62/665,302, filed May 1, 2018.
""U.S. Appl. No. 62/665,317, filed May 1, 2018.
""U.S. Appl. No. 62/665,321, filed May 1, 2018.
""U.S. Appl. No. 62/665,331, filed May 1, 2018.
""U.S. Appl. No. 62/665,335, filed May 1, 2018.
""U.S. Appl. No. 62/853,279, filed May 28, 2019.
""U.S. Appl. No. 62/853,889, filed May 29, 2019.
""U.S. Appl. No. 62/864,656, filed Jun. 21, 2019.
""U.S. Appl. No. 62/873,045, filed Jul. 11, 2019.
""U.S. Appl. No. 62/873,048, filed Jul. 11, 2019.
""U.S. Appl. No. 62/876,500, filed Jul. 19, 2019.
""U.S. Appl. No. 62/877,558, filed Jul. 23, 2019.
""U.S. Appl. No. 62/883,172, filed Aug. 6, 2019.
""U.S. Appl. No. 62/889,149, filed Aug. 20, 2019.
""U.S. Appl. No. 62/923,279, filed Oct. 18, 2019.
""U.S. Appl. No. 62/926,767, filed Oct. 28, 2019.
""U.S. Appl. No. 62/935,337, filed Nov. 14, 2019.
""U.S. Appl. No. 62/938,447, filed Nov. 21, 2019.
""U.S. Appl. No. 62/949,187, filed Dec. 17, 2019.
""U.S. Appl. No. 62/956,756, filed Jan. 3, 2020.
""U.S. Appl. No. 62/956,767, filed Jan. 3, 2020.
""U.S. Appl. No. 62/956,770, filed Jan. 3, 2020.
""U.S. Appl. No. 62/967,158, filed Jan. 26, 2020.
""U.S. Appl. No. 62/967,977, filed Jan. 30, 2020.
""U.S. Appl. No. 62/991,754, filed Mar. 19, 2020.
""U.S. Appl. No. 62/994,912, filed Mar. 26, 2020.
""U.S. Appl. No. 63/008,112, filed Apr. 10, 2020.
""U.S. Appl. No. 63/011,445, filed Apr. 17, 2020.
""U.S. Appl. No. 63/011,487, filed Apr. 17, 2020.
""U.S. Appl. No. 63/011,571, filed Apr. 17, 2020.
""U.S. Appl. No. 63/011,657, filed Apr. 17, 2020.
""U.S. Appl. No. 63/011,760, filed Apr. 17, 2020.
""U.S. Appl. No. 63/012,347, filed Apr. 20, 2020.
""U.S. Appl. No. 63/012,384, filed Apr. 20, 2020.
""U.S. Appl. No. 63/030,685, filed May 27, 2020.
""U.S. Appl. No. 63/047,374, filed Jul. 2, 2020.
""U.S. Appl. No. 63/061,241, filed Aug. 5, 2020.
""U.S. Appl. No. 63/061,244, filed Aug. 5, 2020.
""U.S. Appl. No. 63/061,834, filed Aug. 6, 2020.
""U.S. Appl. No. 63/064,017, filed Aug. 11, 2020.
""U.S. Appl. No. 63/064,126, filed Aug. 11, 2020.
""U.S. Appl. No. 63/067,542, filed Aug. 19, 2020.
""U.S. Appl. No. 63/071,438, filed Aug. 28, 2020.
""U.S. Appl. No. 63/073,545, filed Sep. 2, 2020.
""U.S. Appl. No. 63/073,553, filed Sep. 2, 2020.
""U.S. Appl. No. 63/074,051, filed Sep. 3, 2020.
""U.S. Appl. No. 63/074,066, filed Sep. 3, 2020.
""U.S. Appl. No. 63/076,032, filed Sep. 9, 2020.
""U.S. Appl. No. 63/076,474, filed Sep. 10, 2020.
""U.S. Appl. No. 63/076,477, filed Sep. 10, 2020.
""U.S. Appl. No. 63/082,261, filed Sep. 23, 2020.
""U.S. Appl. No. 63/088,506, filed Oct. 7, 2020.
""U.S. Appl. No. 63/088,511, filed Oct. 7, 2020.
""U.S. Appl. No. 63/094,464, filed Oct. 21, 2020.
""U.S. Appl. No. 63/094,498, filed Oct. 21, 2020.
""U.S. Appl. No. 63/094,594, filed Oct. 21, 2020.
""U.S. Appl. No. 63/094,608, filed Oct. 21, 2020.
""U.S. Appl. No. 63/094,626, filed Oct. 21, 2020.
""U.S. Appl. No. 63/094,646, filed Oct. 21, 2020.
""U.S. Appl. No. 63/109,066, filed Nov. 3, 2020.
""U.S. Appl. No. 63/109,084, filed Nov. 3, 2020.
""U.S. Appl. No. 63/112,417, filed Nov. 11, 2020.
""U.S. Appl. No. 63/119,161, filed Nov. 30, 2020.
""U.S. Appl. No. 63/124,271, filed Dec. 11, 2020.
""U.S. Appl. No. 63/133,892, filed Jan. 5, 2021.
""U.S. Appl. No. 63/134,287, filed Jan. 6, 2021.
""U.S. Appl. No. 63/134,450, filed Jan. 6, 2021.
""U.S. Appl. No. 63/134,631, filed Jan. 7, 2021.
""U.S. Appl. No. 63/134,632, filed Jan. 7, 2021.
""U.S. Appl. No. 63/134,754, filed Jan. 7, 2021.
""U.S. Appl. No. 63/138,878, filed Jan. 19, 2021.
""U.S. Appl. No. 63/146,946, filed Feb. 8, 2021.
""U.S. Appl. No. 63/147,013, filed Feb. 8, 2021.
""U.S. Appl. No. 63/147,299, filed Feb. 9, 2021.
""U.S. Appl. No. 63/148,723, filed Feb. 12, 2021.
""U.S. Appl. No. 63/150,640, filed Feb. 18, 2021.
""U.S. Appl. No. 63/154,248, filed Feb. 26, 2021.
""U.S. Appl. No. 63/155,395, filed Mar. 2, 2021.
""U.S. Appl. No. 63/157,007, filed Mar. 5, 2021.
""U.S. Appl. No. 63/157,014, filed Mar. 5, 2021.
""U.S. Appl. No. 63/159,142, filed Mar. 10, 2021.
""U.S. Appl. No. 63/159,186, filed Mar. 10, 2021.
""U.S. Appl. No. 63/159,210, filed Mar. 10, 2021.
""U.S. Appl. No. 63/165,273, filed Mar. 24, 2021.
""U.S. Appl. No. 63/165,384, filed Mar. 24, 2021.
""U.S. Appl. No. 63/171,165, filed Apr. 6, 2021.
""U.S. Appl. No. 63/172,975, filed Apr. 9, 2021.
""U.S. Appl. No. 63/181,695, filed Apr. 29, 2021.
""U.S. Appl. No. 63/191,558, filed May 21, 2021.
""U.S. Appl. No. 63/192,274, filed May 24, 2021.
""U.S. Appl. No. 63/192,289, filed May 24, 2021.
""U.S. Appl. No. 63/193,235, filed May 26, 2021.
""U.S. Appl. No. 63/193,406, filed May 26, 2021.
""U.S. Appl. No. 63/193,891, filed May 27, 2021.
""U.S. Appl. No. 63/208,262, filed Jun. 8, 2021.
""U.S. Appl. No. 63/214,551, filed Jun. 24, 2021.
""U.S. Appl. No. 63/214,570, filed Jun. 24, 2021.
""U.S. Appl. No. 63/215,017, filed Jun. 25, 2021.
""U.S. Appl. No. 63/228,244, filed Aug. 2, 2021.
""U.S. Appl. No. 63/228,252, filed Aug. 2, 2021.
""U.S. Appl. No. 63/228,258, filed Aug. 2, 2021.
""U.S. Appl. No. 63/230,894, filed Aug. 9, 2021.
""U.S. Appl. No. 63/230,897, filed Aug. 9, 2021.
""U.S. Appl. No. 63/238,457, filed Aug. 30, 2021.
""U.S. Appl. No. 63/238,477, filed Aug. 30, 2021.
""U.S. Appl. No. 63/241,328, filed Sep. 7, 2021.
""U.S. Appl. No. 63/241,562, filed Sep. 8, 2021.
""U.S. Appl. No. 63/241,564, filed Sep. 8, 2021.
""U.S. Appl. No. 63/241,575, filed Sep. 8, 2021.
""U.S. Appl. No. 63/246,972, filed Sep. 22, 2021.
""U.S. Appl. No. 63/247,375, filed Sep. 23, 2021.
""U.S. Appl. No. 63/247,478, filed Sep. 23, 2021.
""U.S. Appl. No. 63/247,491, filed Sep. 23, 2021.
""U.S. Appl. No. 63/299,208, filed Jan. 13, 2022.
""U.S. Appl. No. 63/308,190, filed Feb. 9, 2022.
""Defendant and Counterclaim Plaintiff Sage Products, LLC's Answer, Defenses, and Counterclaims to Plaintiff's Amended Complaint , Nov. 1, 2019.
""*PureWick Corporation* v. *Sage Products, LLC* Transcripts vol. 2 , Mar. 29, 2022.
""*PureWick Corporation* v. *Sage Products, LLC* Transcripts vol. 3 , Mar. 30, 2022.
""*PureWick Corporation* v. *Sage Products, LLC* Transcripts vol. 4 , Mar. 31, 2022.
""Memorandum Order , Feb. 2021.

(56) References Cited

OTHER PUBLICATIONS

“”Sage’s Initial Invalidity Contentions Regarding U.S. Pat. Nos. 8,287,508; 10,226,375; and 10,390,989 , May 29, 2020.
“”Sage’s Supplemental and Initial Invalidity Contentions Regarding U.S. Pat. No’s 8,287,508; 10,226,375; 10,390,989 and Initial Invalidity Contentions Regarding U.S. Pat. No. 10,376,407 , Aug. 21, 2020.
“”Sage’s Second Supplemental Invalidity Contentions Regarding U.S. Pat. Nos. 8,287,508, 10,226,375, 10,390,989, and 10,376,407.
“”Boehringer CareDry System—Second Generation for Non-Invasive Urinary Management for Females , Mar. 2021.
“”*PureWick Corporation* v. *Sage Products, LLC* Transcripts vol. 5 , Apr. 1, 2022.
“”Excerpts from the 508 (U.S. Pat. No. 8,278,508) Patent’s Prosecution History , 2020.
“”*PureWick Corporation* v. *Sage Products, LLC* Transcripts vol. 1 , Mar. 28, 2022.
“”Plaintiff’s Opening Claim Construction Brief , Oct. 16, 2020.
“”Plaintiff’s Identification of Claim Terms and Proposed Constructions.
“”PureWick’s Response to Interrogatory No. 9 in *PureWick, LLC* v. *Sage Products, LLC* , Mar. 23, 2020.
“”Sage’s Preliminary Identification of Claim Elements and Proposed Constructions for U.S. Pat. Nos. 8,287,508, 10,226,376, 10,390,989 and 10,376,407.
“”Decision Granting Institution of Inter Partes Review for U.S. Pat. No. 8,287,508 , Feb. 17, 2021.
“”Corrected Certificate of Service , 2020.
“”Declaration of Diane K. Newman Curriculum Vitae , 2020.
“3 Devices Take Top Honors in Dare-To-Dream Medtech Design Contest”, R+D Digest, Nov. 2013, 1 page.
“Advanced Mission Extender Device (AMDX) Products”, Omni Medical Systems, Inc., 15 pages.
“AMXD Control Starter Kit” , Omni Medical Systems, Inc. , 1 page.
“AMXD Control Starter Kit Brochure”, https://www.omnimedicalsys.com/index.php?page=products, 8 pages.
“AMXDmax Advanced Mission Extender Device User & Maintenance Guide”, Omni Medical, Jan. 11, 2010, 10 pages.
“AMXDmax Development History 2002-2014”, Omni Medical Systems, Inc. , 2 pages.
“AMXDmax In-Flight Bladder Relief”, Omni Medical; Omni Medical Systems, Inc. , 2015.
“AMXDX—Advanced Mission Extender Device Brochure”, Omni Medical , 2 pages.
“Combat Force Multiplier in Flight Bladder Relief Cockpit Essential Equipment Brochure”, Omni Medical , 20 pages.
“External Urine Management for Female Anatomy”, https://www.stryker.com/us/en/sage/products/sage-primafit.html , Jul. 2020 , 4 pages.
“GSA Price List”, Omni Medical , Apr. 2011 , 2 pages.
“High Absorbancy Cellulose Acetate Electrospun Nanofibers for Feminine Hygiene Application” https://www.sciencedirect.com/science/article/abs/pii/S2352940716300701?via%3Dihub , Jul. 2016, 3 pages.
“How is Polypropylene Fiber Made”, https:www.yarnsandfibers.com/textile-resources/synthetic-fibers/polypropylene-fiber/polypropylene-fiber-production-raw-materials/how-is-polypropylene-fiber-made/ last accessed 2020 , Oct. 7, 2020 , 3 pages.
“How Period Panties Work”, www.shethinx.com/pages/thinx-itworks , 2020 , 10 pages.
“Hydrogel properties of electrospun polyvinylpyrrolidone and polyvinylpyrrolidone/poly(acrylic acid) blend nanofibers”, https://pubs.rsc.org/en/content/articlelanding/2015/ra/c5ra07514a#!divAbstract , 2015 , 5 pages.
“In Flight Bladder Relief” Omni Medical , 14 pages.
“Letter to Mark Harvie of Omni Measurement Systems”, Department of Veterans Affairs , Nov. 1, 2007 , 11 pages.
“Making Women’s Sanitary Products Safer and Cheaper”, https://www.elsevier.com/connect/making-womens-sanitary-products-safer-and-cheaper, Sep. 2016, 10 pages.
“Novel Nanofibers Make Safe and Effective Absorbent for Sanitary Products”, https://www.materialstoday.com/nanomaterials/news/nanofibers-make-safe-and-effective-absorbent/ , Oct. 2016 , 3 pages.
“Research and Development Work Relating to Assistive Technology Jun. 2005”, British Department of Health , Nov. 2006 , 40 pages.
“Revised AMXDmax Advanced Mission Extender Device User & Maintenance Guide”, Omni Medical Systems , Oct. 8, 2019 , 52 pages.
“Rising Warrior Insulated Gallon Jug Cover”, https://www.amazon.com/Rising-Warrior-Insulated-Sleeve , 2021 , 2 pages.
“Step by Step How Ur24 WorksHome”, http://medicalpatentur24.com , Aug. 30, 2017 , 4 pages.
“Underwear that absorbs your period”, Thinx! , 7 pages.
“Urine Bag Cover-Catheter Bag Cover 2000 ml Volume-Medline Style-Multiple Sclerosis-Spine Injury-Suprapublic Catheter-Bladder Incontinence”, https://www.etsy.com/listing/1142934658/urine-bag-cover-caatheter-bag-cover-2000, 2022, 1 page.
“User & Maintenance Guide”, Omni Medical , 2007 , 16 pages.
“Vinyl Dust Cover, Janome #741811000, Janome, Sewing Parts Online”, https://www.sewingpartsonline.com/vinyl-dust-cover-janome-74181000 , 2020 , 2 pages.
“Winners Announced for Dare-to-Dream Medtech Design Challenge”, https://www.mddionline.com/design-engineering/winners-announced-dare-dream-medtech-design-challenge , 2014, 4 pages.
Ali , “Sustainability Assessment: Seventh Generation Diapers versus gDiapers”, The University of Vermont , Dec. 6, 2011 , pp. 1-31.
Autumn , et al. , “Frictional adhesion: a new angle on gecko attachment”, The Journal of Experimental Biology , 2006 , pp. 3569-3579.
Cañas , et al. , “Effect of nano- and micro-roughness on adhesion of bioinspired micropatterned surfaces”, Acta Biomaterialia 8 , 2012 , pp. 282-288.
Chaudhary , et al. , “Bioinspired dry adhesive: Poly(dimethylsiloxane) grafted with poly(2-ethylhexyl acrylate) brushes”, European Polymer Journal , 2015 , pp. 432-440.
Dai , et al. , “Non-sticky and Non-slippery Biomimetic Patterned Surfaces”, Journal of Bionic Engineering , Mar. 2020 , pp. 326-334.
Espinoza-Ramirez, “Nanobiodiversity and Biomimetic Adhesives Development: From Nature to Production and Application”, Journal of Biomaterials and Nanobiotechnology, pp. 78-101, 2019.
Hollister , “Female Urinary and Pouch and Male Urinary Pouch Brochure”, www.hollister.com , 2011 , 1 page.
Hollister , “Male Urinary Pouch External Collection Device”, http://www.hollister.com/en/products/Continence-Care-Products/Urine-Collectors/Urine-Collection-Accessories/Male-Urinary-Pouch-External-Collection-Device.
Hollister , “Retracted Penis Pouch by Hollister”, Vitality Medical.com.
Hwang , et al. , “Multifunctional Smart Skin Adhesive Patches for Advanced Health Care”, Adv. Healthcare Mater , 2018 , pp. 1-20.
Jagota , et al. , “Adhesion, friction, and compliance of bio-mimetic and bio-inspired structured interfaces”, Materials Science and Engineering , 2011 , pp. 253-292.
Jeong , et al. , “A nontransferring dry adhesive with hierarchical polymer nanohairs”, PNAS , Apr. 7, 2009 , pp. 5639-5644.
Jeong , et al. , “Nanohairs and nanotubes: Efficient structural elements for gecko-inspired artificial dry adhesives”, Science Direct , 2009 , pp. 335-346.
Karp , et al. , “Dry solution to a sticky problem”, Nature. , 2011 , pp. 42-43.
Lee , et al. , “Continuous Fabrication of Wide-Tip Microstructures for Bio-Inspired Dry Adhesives via Tip Inking Process”, Journal of Chemistry , Jan. 2, 2019 , pp. 1-5.
Macaulay , et al. , “A Noninvasive Continence Management System: Development and Evaluation of a Novel Toileting Device for Women”, The Wound, Ostomy and Continence Nurses Society , 2007 , pp. 641-648.
Merriam-Webster Dictionary, , “Embed Definition & Meaning”, https://www.merriam-webster.com/dictionary/embed last accessed Aug. 3, 2023 , 2003.
Newman , et al. , “The Urinary Incontinence Sourcebook”, Petition for Interparties Review , 1997 , 23 pages.

(56) References Cited

OTHER PUBLICATIONS

Newton , et al. , "Measuring Safety, Effectiveness and Ease of Use of PureWick in the Management of Urinary Incontinence in Bedbound Women: Case Studies", , 11 pages.
Parmar , "10 Finalists Chosen for Dare-to-Dream Medtech Design Challenge (PureWick)", Design Services , Nov. 10, 2014 , 3 pages.
Parness , et al. , "A microfabricated wedge-shaped adhesive array displaying gecko-like dynamic adhesion, directionality", J.R. Soc. Interface , 2009 , pp. 1223-1232.
Pieper , et al. , "An external urine-collection device for women: A clinical trial", Journal of ER Nursing, vol. 20, No. 2 , Mar./Apr. 1993 , pp. 51-55.
Purewick , "Incontinence Relief for Women", Presentation , Sep. 23, 2015 , 7 pages.
Pytlik , "Super Absorbent Polymers", University of Buffalo.
Sachtman , "New Relief for Pilots? It Depends", Wired , 2008 , 2 pages.
Tsipenyuk , et al. , "Use of biomimetic hexagonal surface texture in friction against lubricated skin", Journal of the Royal Society—Interface , 2014 , pp. 1-6.
Vinas, "A Solution for an Awkward—But Serious—Subject", http://www.aero-574 news.net/index.cfm?do=main.textpost&id=69ae2bb1-838b-4098-a7b5-7flbb2505688 last accessed Feb. 8, 2021.
"Proximate Definition & Meaning" <https://www.merriam-webster.com/dictionary/> 2025.
"Surface Energy Data for Cellulose acetate, CAS # 9004-35-7", Diviersified Enterprises, 2009, 1 page.
"TUBE Definition & Meaning" Merriam Webster Dictionary, 2025, <https://www.merriam-webster.com/dictionary/tube>.
Advisory Action for U.S. Appl. No. 16/452,258 mailed May 5, 2025.
Advisory Action for U.S. Appl. No. 17/378,015 mailed Oct. 28, 2025.
Advisory Action for U.S. Appl. No. 17/394,055 mailed Jan. 9, 2026.
Advisory Action for U.S. Appl. No. 17/446,256 mailed Nov. 6, 2025.
Advisory Action for U.S. Appl. No. 17/446,654 mailed Feb. 28, 2025.
Advisory Action for U.S. Appl. No. 17/451,345 mailed May 13, 2025.
Advisory Action for U.S. Appl. No. 17/595,747 mailed Mar. 17, 2025.
Advisory Action for U.S. Appl. No. 17/653,314 mailed Apr. 8, 2025.
Advisory Action for U.S. Appl. No. 17/655,464 mailed Feb. 25, 2025.
Advisory Action for U.S. Appl. No. 17/664,487 mailed Apr. 24, 2025.
Advisory Action for U.S. Appl. No. 17/757,311 mailed Jul. 2, 2025.
Advisory Action for U.S. Appl. No. 18/247,986 mailed Apr. 1, 2026.
Advisory Action for U.S. Appl. No. 18/265,736 mailed Mar. 4, 2026.
Corrected Notice of Allowability for U.S. Appl. No. 17/444,792 mailed Jun. 24, 2025.
Corrected Notice of Allowability for U.S. Appl. No. 17/653,314 mailed Oct. 29, 2025.
Corrected Notice of Allowability for U.S. Appl. No. 17/754,736 mailed Feb. 12, 2026.
Corrected Notice of Allowability for U.S. Appl. No. 17/808,354 mailed Nov. 25, 2025.
Corrected Notice of Allowability for U.S. Appl. No. 17/996,253 mailed Apr. 28, 2025.
Corrected Notice of Allowability for U.S. Appl. No. 18/134,857 mailed Mar. 14, 2025.
Corrected Notice of Allowability for U.S. Appl. No. 18/260,122 mailed Aug. 11, 2025.
Corrected Notice of Allowability for U.S. Appl. No. 18/264,004 mailed Feb. 10, 2026.
Corrected Notice of Allowability for U.S. Appl. No. 18/264,004 mailed Feb. 3, 2026.
Corrected Notice of Allowability for U.S. Appl. No. 18/294,370 mailed Mar. 31, 2026.
Di Mauro, et al., "Penile length and circumference dimensions: A large study in young Italian men" Reconstructive Urology, Men's Health Working Parties of the European Association of Urology (EAU) Young Academic Urologists (YAU). pp. 1-7, Mar. 8, 2021.
Final Office Action for U.S. Appl. No. 16/452,258 mailed Feb. 11, 2026.
Final Office Action for U.S. Appl. No. 17/051,600 mailed Aug. 6, 2025.
Final Office Action for U.S. Appl. No. 17/378,015 mailed Jun. 18, 2025.
Final Office Action for U.S. Appl. No. 17/394,055 mailed Sep. 24, 2025.
Final Office Action for U.S. Appl. No. 17/446,256 mailed Jun. 11, 2025.
Final Office Action for U.S. Appl. No. 17/446,654 mailed Dec. 22, 2025.
Final Office Action for U.S. Appl. No. 17/451,345 mailed Feb. 6, 2025.
Final Office Action for U.S. Appl. No. 17/595,747 mailed Feb. 19, 2026.
Final Office Action for U.S. Appl. No. 17/597,408 mailed Mar. 24, 2025.
Final Office Action for U.S. Appl. No. 17/614,173 mailed May 20, 2025.
Final Office Action for U.S. Appl. No. 17/625,941 mailed Feb. 18, 2025.
Final Office Action for U.S. Appl. No. 17/628,411 mailed Apr. 30, 2025.
Final Office Action for U.S. Appl. No. 17/631,619 mailed Oct. 1, 2025.
Final Office Action for U.S. Appl. No. 17/653,137 mailed Jun. 25, 2025.
Final Office Action for U.S. Appl. No. 17/653,314 mailed Jan. 30, 2025.
Final Office Action for U.S. Appl. No. 17/653,920 mailed Apr. 24, 2025.
Final Office Action for U.S. Appl. No. 17/655,464 mailed Feb. 17, 2026.
Final Office Action for U.S. Appl. No. 17/664,487 mailed Jan. 5, 2026.
Final Office Action for U.S. Appl. No. 17/756,201 mailed Dec. 30, 2025.
Final Office Action for U.S. Appl. No. 17/757,311 mailed Mar. 31, 2025.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/809,083 mailed Jan. 23, 2026.
Final Office Action for U.S. Appl. No. 17/907,125 mailed Apr. 30, 2025.
Final Office Action for U.S. Appl. No. 17/929,887, filed Jan. 13, 2026.
Final Office Action for U.S. Appl. No. 17/933,590 mailed Feb. 19, 2026.
Final Office Action for U.S. Appl. No. 18/003,029 mailed Nov. 26, 2025.
Final Office Action for U.S. Appl. No. 18/006,807 mailed Dec. 23, 2025.
Final Office Action for U.S. Appl. No. 18/042,842 mailed Jan. 27, 2026.
Final Office Action for U.S. Appl. No. 18/043,618 mailed Nov. 26, 2025.
Final Office Action for U.S. Appl. No. 18/139,523 mailed May 8, 2025.
Final Office Action for U.S. Appl. No. 18/164,800 mailed Dec. 5, 2025.
Final Office Action for U.S. Appl. No. 18/247,986 mailed Jan. 7, 2026.

(56) References Cited

OTHER PUBLICATIONS

Final Office Action for U.S. Appl. No. 18/265,736 mailed Dec. 1, 2025.
Foamtech, "Foam Packaging Isnert: Best Selection Guide", https://web/archive.org/web/20170922162235/http://www.foamtechchina/com:80/foam-packaging-insert/, Sep. 22, 2017, 25 pages.
International Search Report and Written Opinion from International Application No. PCT/US2023/031432 mailed Feb. 29, 2024.
International Search Report and Written Opinion from International Application No. PCT/US2023/036875 mailed May 31, 2024.
International Search Report and Written Opinion from International Application No. PCT/US2023/077205 mailed Jul. 19, 2024.
International Search Report and Written Opinion from International Application No. PCT/US2024/053681 mailed Jan. 27, 2025.
International Search Report and Written Opinion from International Application No. PCT/US2024/058598 mailed Mar. 28, 2025.
International Search Report and Written Opinion from International Application No. PCT/US2025/018907 mailed May 16, 2025.
International Search Report and Written Opinion from International Application No. PCT/US2025/018909 mailed May 20, 2025.
International Search Report and Written Opinion from International Application No. PCT/US2025/018913 mailed Jun. 18, 2025.
Issue Notification for U.S. Appl. No. 16/433,773 mailed Jan. 21, 2026.
Issue Notification for U.S. Appl. No. 16/478,180 mailed Mar. 5, 2025.
Issue Notification for U.S. Appl. No. 16/904,868 mailed Apr. 30, 2025.
Issue Notification for U.S. Appl. No. 17/051,399 mailed Mar. 4, 2026.
Issue Notification for U.S. Appl. No. 17/051,585 mailed Mar. 26, 2025.
Issue Notification for U.S. Appl. No. 17/444,792 mailed Jun. 25, 2025.
Issue Notification for U.S. Appl. No. 17/451,354 mailed Feb. 25, 2026.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/597,673 mailed Jun. 4, 2025.
Issue Notification for U.S. Appl. No. 17/625,941 mailed Feb. 25, 2026.
Issue Notification for U.S. Appl. No. 17/646,771 mailed Mar. 19, 2025.
Issue Notification for U.S. Appl. No. 17/653,137 mailed Feb. 4, 2025.
Issue Notification for U.S. Appl. No. 17/653,314 mailed Feb. 11, 2026.
Issue Notification for U.S. Appl. No. 17/653,920 mailed Oct. 22, 2025.
Issue Notification for U.S. Appl. No. 17/661,090 mailed Feb. 5, 2025.
Issue Notification for U.S. Appl. No. 17/663,330 mailed Feb. 26, 2025.
Issue Notification for U.S. Appl. No. 17/749,340 mailed May 28, 2025.
Issue Notification for U.S. Appl. No. 17/755,236 mailed Oct. 29, 2025.
Issue Notification for U.S. Appl. No. 17/758,316 mailed Jun. 25, 2025.
Issue Notification for U.S. Appl. No. 17/808,354 mailed Mar. 4, 2026.
Issue Notification for U.S. Appl. No. 17/878,268 mailed Feb. 4, 2026.
Issue Notification for U.S. Appl. No. 17/907,125 mailed Dec. 30, 2025.
Issue Notification for U.S. Appl. No. 17/912,147 mailed Mar. 18, 2026.
Issue Notification for U.S. Appl. No. 17/996,064 mailed Nov. 5, 2025.
Issue Notification for U.S. Appl. No. 17/996,155 mailed Oct. 8, 2025.
Issue Notification for U.S. Appl. No. 17/996,253 mailed Oct. 29, 2025.
Issue Notification for U.S. Appl. No. 17/996,468 mailed Nov. 26, 2025.
Issue Notification for U.S. Appl. No. 18/007,105 mailed Oct. 1, 2025.
Issue Notification for U.S. Appl. No. 18/044,413 mailed Dec. 30, 2025.
Issue Notification for U.S. Appl. No. 18/134,857 mailed May 28, 2025.
Issue Notification for U.S. Appl. No. 18/140,751 mailed Feb. 12, 2025.
Issue Notification for U.S. Appl. No. 18/260,122 mailed Nov. 12, 2025.
Issue Notification for U.S. Appl. No. 18/415,080 mailed Apr. 9, 2025.
Issue Notification for U.S. Appl. No. 18/426,795 mailed Feb. 19, 2025.
Issue Notification for U.S. Appl. No. 18/584,002 mailed Apr. 16, 2025.
Non-Final Office Action for U.S. Appl. No. 16/433,773 mailed Feb. 28, 2025.
Non-Final Office Action for U.S. Appl. No. 16/452,258 mailed Sep. 24, 2025.
Non-Final Office Action for U.S. Appl. No. 17/051,600 mailed Feb. 28, 2025.
Non-Final Office Action for U.S. Appl. No. 17/378,015 mailed Dec. 12, 2025.
Non-Final Office Action for U.S. Appl. No. 17/394,055 mailed Mar. 13, 2025.
Non-Final Office Action for U.S. Appl. No. 17/394,055 mailed Mar. 19, 2025.
Non-Final Office Action for U.S. Appl. No. 17/446,256 mailed Dec. 2, 2025.
Non-Final Office Action for U.S. Appl. No. 17/446,654 mailed May 1, 2025.
Non-Final Office Action for U.S. Appl. No. 17/451,354 mailed Mar. 19, 2025.
Non-Final Office Action for U.S. Appl. No. 17/595,747 mailed Jun. 12, 2025.
Non-Final Office Action for U.S. Appl. No. 17/614,173 mailed Dec. 29, 2025.
Non-Final Office Action for U.S. Appl. No. 17/628,411 mailed Dec. 22, 2025.
Non-Final Office Action for U.S. Appl. No. 17/631,619 mailed Mar. 19, 2025.
Non-Final Office Action for U.S. Appl. No. 17/635,866 mailed Jul. 29, 2025.
Non-Final Office Action for U.S. Appl. No. 17/645,821 mailed Mar. 31, 2025.
Non-Final Office Action for U.S. Appl. No. 17/653,137 mailed Jan. 28, 2025.
Non-Final Office Action for U.S. Appl. No. 17/653,314 mailed May 8, 2025.
Non-Final Office Action for U.S. Appl. No. 17/655,464 mailed Mar. 20, 2025.
Non-Final Office Action for U.S. Appl. No. 17/664,487 mailed May 19, 2025.
Non-Final Office Action for U.S. Appl. No. 17/754,736 mailed Mar. 31, 2025.
Non-Final Office Action for U.S. Appl. No. 17/756,201 mailed Apr. 24, 2025.
Non-Final Office Action for U.S. Appl. No. 17/757,311 mailed Sep. 2, 2025.
Non-Final Office Action for U.S. Appl. No. 17/758,152 mailed Apr. 8, 2025.
Non-Final Office Action for U.S. Appl. No. 17/759,587 mailed Jan. 26, 2026.

(56) References Cited

OTHER PUBLICATIONS

Non-Final Office Action for U.S. Appl. No. 17/759,697 mailed Sep. 17, 2025.
Non-Final Office Action for U.S. Appl. No. 17/809,083 mailed Apr. 2, 2025.
Non-Final Office Action for U.S. Appl. No. 17/809,083 mailed Mar. 7, 2025.
Non-Final Office Action for U.S. Appl. No. 17/878,268 mailed Mar. 17, 2025.
Non-Final Office Action for U.S. Appl. No. 17/912,147 mailed May 29, 2025.
Non-Final Office Action for U.S. Appl. No. 17/929,887 mailed Jun. 25, 2025.
Non-Final Office Action for U.S. Appl. No. 17/930,238 mailed Jun. 30, 2025.
Non-Final Office Action for U.S. Appl. No. 17/933,590 mailed Jul. 29, 2025.
Non-Final Office Action for U.S. Appl. No. 17/996,064 mailed Mar. 6, 2025.
Non-Final Office Action for U.S. Appl. No. 17/996,556 mailed Dec. 22, 2025.
Non-Final Office Action for U.S. Appl. No. 18/003,029 mailed Apr. 18, 2025.
Non-Final Office Action for U.S. Appl. No. 18/006,807 mailed May 29, 2025.
Non-Final Office Action for U.S. Appl. No. 18/034,902 mailed Mar. 20, 2026.
Non-Final Office Action for U.S. Appl. No. 18/042,842 mailed May 22, 2025.
Non-Final Office Action for U.S. Appl. No. 18/043,618 mailed May 19, 2025.
Non-Final Office Action for U.S. Appl. No. 18/043,807 mailed Feb. 10, 2026.
Non-Final Office Action for U.S. Appl. No. 18/115,444 mailed Oct. 22, 2025.
Non-Final Office Action for U.S. Appl. No. 18/139,523 mailed Nov. 19, 2025.
Non-Final Office Action for U.S. Appl. No. 18/150,360 mailed Nov. 5, 2025.
Non-Final Office Action for U.S. Appl. No. 18/164,800 mailed Apr. 25, 2025.
Non-Final Office Action for U.S. Appl. No. 18/246,121 mailed Jan. 22, 2026.
Non-Final Office Action for U.S. Appl. No. 18/247,986 mailed Jun. 4, 2025.
Non-Final Office Action for U.S. Appl. No. 18/249,577 mailed Nov. 17, 2025.
Non-Final Office Action for U.S. Appl. No. 18/254,638 mailed Nov. 17, 2025.
Non-Final Office Action for U.S. Appl. No. 18/259,626 mailed Jan. 30, 2026.
Non-Final Office Action for U.S. Appl. No. 18/259,626 mailed Jul. 11, 2025.
Non-Final Office Action for U.S. Appl. No. 18/260,394, filed Jan. 13, 2026.
Non-Final Office Action for U.S. Appl. No. 18/263,800 mailed Feb. 5, 2026.
Non-Final Office Action for U.S. Appl. No. 18/264,004 mailed May 15, 2025.
Non-Final Office Action for U.S. Appl. No. 18/264,278 mailed Nov. 10, 2025.
Non-Final Office Action for U.S. Appl. No. 18/265,736 mailed Jul. 1, 2025.
Non-Final Office Action for U.S. Appl. No. 18/376,274 mailed Mar. 9, 2026.
Non-Final Office Action for U.S. Appl. No. 18/546,465 mailed Apr. 1, 2026.
Non-Final Office Action for U.S. Appl. No. 18/548,152 mailed Sep. 16, 2025.
Non-Final Office Action for U.S. Appl. No. 18/549,387 mailed Mar. 4, 2026.
Non-Final Office Action for U.S. Appl. No. 18/551,492 mailed Mar. 19, 2026.
Non-Final Office Action for U.S. Appl. No. 18/556,945 mailed Dec. 19, 2025.
Non-Final Office Action for U.S. Appl. No. 18/562,626 mailed Feb. 11, 2026.
Non-Final Office Action for U.S. Appl. No. 18/563,672 mailed Feb. 12, 2026.
Non-Final Office Action for U.S. Appl. No. 18/569,711 mailed Mar. 30, 2026.
Non-Final Office Action for U.S. Appl. No. 18/662,216 mailed Mar. 9, 2026.
Non-Final Office Action for U.S. Appl. No. 18/681,987 mailed Mar. 30, 2026.
Non-Final Office Action for U.S. Appl. No. 18/682,006 mailed Mar. 4, 2026.
Non-Final Office Action for U.S. Appl. No. 18/689,532 mailed Mar. 19, 2026.
Non-Final Office Action for U.S. Appl. No. 18/690,392 mailed Feb. 9, 2026.
Non-Final Office Action for U.S. Appl. No. 18/694,090 mailed Mar. 17, 2026.
Non-Final Office Action for U.S. Appl. No. 18/757,964 mailed Aug. 20, 2025.
Non-Final Office Action for U.S. Appl. No. 18/757,964 mailed Mar. 27, 2026.
Non-Final Office Action for U.S. Appl. No. 29/892,478 mailed Mar. 12, 2026.
Notice of Allowance for U.S. Appl. No. 16/433,773 mailed Oct. 10, 2025.
Notice of Allowance for U.S. Appl. No. 17/051,399 mailed Nov. 17, 2025.
Notice of Allowance for U.S. Appl. No. 17/051,600 mailed Jan. 5, 2026.
Notice of Allowance for U.S. Appl. No. 17/394,055 mailed Mar. 20, 2026.
Notice of Allowance for U.S. Appl. No. 17/444,792 mailed Mar. 28, 2025.
Notice of Allowance for U.S. Appl. No. 17/451,345 mailed Jun. 24, 2025.
Notice of Allowance for U.S. Appl. No. 17/451,354 mailed Nov. 18, 2025.
Notice of Allowance for U.S. Appl. No. 17/596,629 mailed Jan. 29, 2025.
Notice of Allowance for U.S. Appl. No. 17/596,629 mailed May 27, 2025.
Notice of Allowance for U.S. Appl. No. 17/597,673 mailed Feb. 26, 2025.
Notice of Allowance for U.S. Appl. No. 17/625,887 mailed Mar. 3, 2026.
Notice of Allowance for U.S. Appl. No. 17/625,941 mailed Nov. 13, 2025.
Notice of Allowance for U.S. Appl. No. 17/635,866 mailed Mar. 2, 2026.
Notice of Allowance for U.S. Appl. No. 17/645,821 mailed Nov. 24, 2025.
Notice of Allowance for U.S. Appl. No. 17/653,137 mailed Oct. 22, 2025.
Notice of Allowance for U.S. Appl. No. 17/653,314 mailed Oct. 20, 2025.
Notice of Allowance for U.S. Appl. No. 17/653,920 mailed Jul. 9, 2025.
Notice of Allowance for U.S. Appl. No. 17/749,340 mailed Feb. 14, 2025.
Notice of Allowance for U.S. Appl. No. 17/754,736 mailed Jan. 28, 2026.
Notice of Allowance for U.S. Appl. No. 17/755,236 mailed Jul. 17, 2025.
Notice of Allowance for U.S. Appl. No. 17/758,316 mailed Mar. 24, 2025.

(56) References Cited

OTHER PUBLICATIONS

Notice of Allowance for U.S. Appl. No. 17/759,697 mailed Jan. 30, 2026.
Notice of Allowance for U.S. Appl. No. 17/808,354 mailed Nov. 12, 2025.
Notice of Allowance for U.S. Appl. No. 17/878,268 mailed Oct. 15, 2025.
Notice of Allowance for U.S. Appl. No. 17/907,125 mailed Sep. 26, 2025.
Notice of Allowance for U.S. Appl. No. 17/912,147 mailed Dec. 3, 2025.
Notice of Allowance for U.S. Appl. No. 17/930,238 mailed Dec. 16, 2025.
Notice of Allowance for U.S. Appl. No. 17/996,064 mailed Jul. 29, 2025.
Notice of Allowance for U.S. Appl. No. 17/996,155 mailed Jun. 24, 2025.
Notice of Allowance for U.S. Appl. No. 17/996,155 mailed Mar. 11, 2025.
Notice of Allowance for U.S. Appl. No. 17/996,253 mailed Apr. 11, 2025.
Notice of Allowance for U.S. Appl. No. 17/996,253 mailed Jul. 11, 2025.
Notice of Allowance for U.S. Appl. No. 17/996,468 mailed Apr. 14, 2025.
Notice of Allowance for U.S. Appl. No. 17/996,468 mailed Jul. 15, 2025.
Notice of Allowance for U.S. Appl. No. 18/007,105 mailed Jun. 17, 2025.
Notice of Allowance for U.S. Appl. No. 18/041,109 mailed Mar. 25, 2026.
Notice of Allowance for U.S. Appl. No. 18/044,413 mailed Sep. 16, 2025.
Notice of Allowance for U.S. Appl. No. 18/134,857 mailed Feb. 20, 2025.
Notice of Allowance for U.S. Appl. No. 18/249,577 mailed Mar. 31, 2026.
Notice of Allowance for U.S. Appl. No. 18/260,122 mailed Jul. 30, 2025.
Notice of Allowance for U.S. Appl. No. 18/264,004 mailed Jan. 30, 2026.
Notice of Allowance for U.S. Appl. No. 18/294,370 mailed Mar. 17, 2026.
Notice of Allowance for U.S. Appl. No. 18/610,523 mailed Mar. 4, 2026.
Restriction Requirement for U.S. Appl. No. 17/625,887 mailed Sep. 2, 2025.
Restriction Requirement for U.S. Appl. No. 17/755,236 mailed Apr. 24, 2025.
Restriction Requirement for U.S. Appl. No. 17/929,887 mailed Mar. 10, 2025.
Restriction Requirement for U.S. Appl. No. 17/930,238 mailed Apr. 17, 2025.
Restriction Requirement for U.S. Appl. No. 17/996,556 mailed Aug. 11, 2025.
Restriction Requirement for U.S. Appl. No. 18/034,902 mailed Nov. 6, 2025.
Restriction Requirement for U.S. Appl. No. 18/041,109 mailed Jun. 4, 2025.
Restriction Requirement for U.S. Appl. No. 18/041,109 mailed Oct. 23, 2025.
Restriction Requirement for U.S. Appl. No. 18/150,360 mailed May 19, 2025.
Restriction Requirement for U.S. Appl. No. 18/246,121 mailed Jul. 25, 2025.
Restriction Requirement for U.S. Appl. No. 18/249,577 mailed Aug. 25, 2025.
Restriction Requirement for U.S. Appl. No. 18/254,638 mailed Jul. 21, 2025.
Restriction Requirement for U.S. Appl. No. 18/260,394 mailed Jul. 25, 2025.
Restriction Requirement for U.S. Appl. No. 18/294,370 mailed Nov. 26, 2025.
Restriction Requirement for U.S. Appl. No. 18/294,403 mailed Jan. 27, 2026.
Restriction Requirement for U.S. Appl. No. 18/335,579 mailed Nov. 26, 2025.
Restriction Requirement for U.S. Appl. No. 18/373,424 mailed Nov. 14, 2025.
Restriction Requirement for U.S. Appl. No. 18/376,274 mailed Dec. 10, 2025.
Restriction Requirement for U.S. Appl. No. 18/549,387 mailed Dec. 9, 2025.
Restriction Requirement for U.S. Appl. No. 18/551,492 mailed Nov. 10, 2025.
Restriction Requirement for U.S. Appl. No. 18/558,502 mailed Jan. 29, 2026.
Restriction Requirement for U.S. Appl. No. 18/569,711 mailed Jan. 6, 2026.
Restriction Requirement for U.S. Appl. No. 18/569,778 mailed Jan. 15, 2026.
Restriction Requirement for U.S. Appl. No. 18/662,216 mailed Nov. 26, 2025.
Restriction Requirement for U.S. Appl. No. 18/687,117 mailed Mar. 26, 2026.
Restriction Requirement for U.S. Appl. No. 19/237,638 mailed Dec. 18, 2025.
Supplemental Notice of Allowance for U.S. Appl. No. 17/597,673 mailed Apr. 10, 2025.
U.S. Appl. No. 17/051,399, filed Oct. 28, 2020.
U.S. Appl. No. 17/596,629, filed Dec. 15, 2021.
U.S. Appl. No. 17/625,941, filed Jan. 10, 2022.
U.S. Appl. No. 18/034,902, filed May 2, 2023.
U.S. Appl. No. 18/546,465, filed Aug. 15, 2023.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/069,480, filed Mar. 4, 2025.
U.S. Appl. No. 19/078,602, filed Mar. 13, 2025.
U.S. Appl. No. 19/092,262, filed Mar. 27, 2025.
U.S. Appl. No. 19/103,165, filed Feb. 11, 2025.
U.S. Appl. No. 19/110,938, filed Mar. 12, 2025.
U.S. Appl. No. 19/111,921, filed Mar. 14, 2025.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 19/329,723, filed Sep. 16, 2025.
U.S. Appl. No. 19/337,217, filed Sep. 23, 2025.
U.S. Appl. No. 19/353,151, filed Oct. 8, 2025.
U.S. Appl. No. 19/356,506, filed Oct. 13, 2025.
U.S. Appl. No. 19/358,647, filed Oct. 15, 2025.
U.S. Appl. No. 19/370,361, filed Oct. 27, 2025.
U.S. Appl. No. 19/418,150, filed Dec. 12, 2025.
U.S. Appl. No. 19/443,729, filed Jan. 8, 2026.
U.S. Appl. No. 19/447,347, filed Jan. 13, 2026.
U.S. Appl. No. 19/451,614, filed Jan. 16, 2026.
U.S. Appl. No. 19/491,481, filed Dec. 9, 2025.
U.S. Appl. No. 19/494,631, filed Dec. 18, 2025.
U.S. Appl. No. 19/510,850, filed Feb. 12, 2026.
U.S. Appl. No. 19/513,755, filed Feb. 24, 2026.
U.S. Appl. No. 19/513,838, filed Feb. 24, 2026.
U.S. Appl. No. 19/514,100, filed Feb. 25, 2026.

(56) References Cited

OTHER PUBLICATIONS

U.S. Appl. No. 19/534,156, filed Feb. 9, 2026.
U.S. Appl. No. 19/535,649, filed Feb. 10, 2026.
U.S. Appl. No. 19/539,961, filed Feb. 13, 2026.
U.S. Appl. No. 19/541,655, filed Feb. 17, 2026.
U.S. Appl. No. 19/544,501, filed Feb. 19, 2026.
U.S. Appl. No. 19/554,125, filed Mar. 2, 2026.
U.S. Appl. No. 63/181,709, filed Apr. 29, 2021.

* cited by examiner

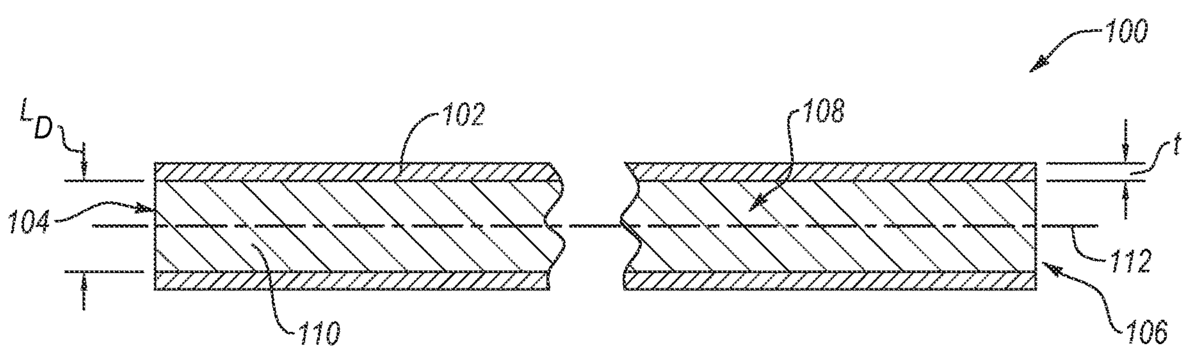
FIG. 1
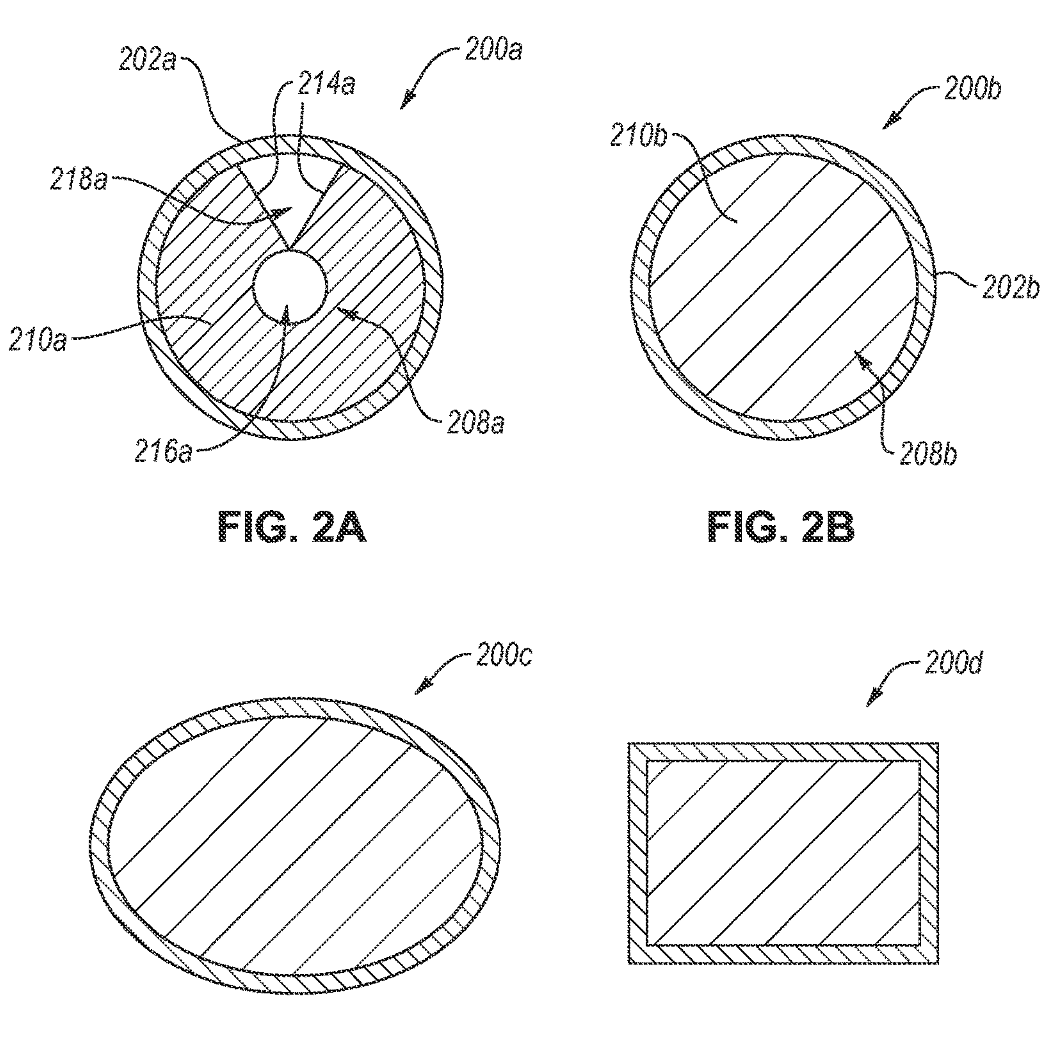
FIG. 2A
FIG. 2B
FIG. 2C
FIG. 2D 1122
1110
1134
1135
1100
1144
1142
1140
1150
1108
1146
1104
1150
1102
1136

1222
1200
1250
1234
1235
1210
1240
1246
1208
1242
1204
1202
1236

1322
1300
1346
1334
1335
1310
1340
1346
1308
1342
1304
1302
1350

1422
1450
1446
1442
1460
1440
1434
1435
1410
1400
1408
1402
1441
1439
1404
1402

CONDUITS INCLUDING AT LEAST ONE CONDUIT POROUS MATERIAL

CROSS-REFERENCE TO RELATED APPLICATION(S)

This application is a U.S. Nationalization of PCT International Application No. PCT/US2022/023594 filed on Apr. 6, 2022, which claims priority to U.S. Patent Provisional Application No. 63/172,975 filed on Apr. 9, 2021, the disclosure of each of which is incorporated herein, in its entirety, by this reference.

BACKGROUND

A patient may have limited or impaired mobility such that typical urination processes are challenging or impossible. For example, the patient may have surgery or a disability that impairs mobility. In another example, the patient may have restricted travel conditions such as those experience by pilots, drivers, and workers in hazardous areas. Additionally, fluid collection from the patient may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections. Further, conduits used in association with urinary catheters may be prone to kinking and collapsing.

Thus, users and manufacturers of fluid collection assemblies continue to seek new and improved devices, systems, and methods to collect urine.

SUMMARY

Embodiments disclosed herein include conduits including at least one conduit porous material, fluid collection assemblies and systems including the same, and methods of using and forming the same. In an embodiment, a conduit for use in a fluid collection system for collecting one or more bodily fluids is disclosed. The conduit includes at least one wall at least partially defining at least an inlet, an outlet, and a passageway extending from the inlet to the outlet. The conduit also includes at least one conduit porous material disposed in at least a portion of the passageway.

In an embodiment, a fluid collection system is disclosed. The fluid collection system includes a fluid collection assembly. The fluid collection assembly includes a fluid impermeable barrier defining at least a chamber, at least one opening, and a fluid outlet. The fluid collection assembly also includes at least one assembly porous material disposed in the chamber. The fluid collection system also includes the conduit in fluid communication with the chamber. The conduit includes at least one wall at least partially defining at least an inlet, an outlet, and a passageway extending from the inlet to the outlet. The conduit also includes at least one conduit porous material disposed in at least a portion of the passageway.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

FIG. 1 is a cross-sectional schematic of a conduit, according to an embodiment.

FIGS. 2A to 2D are cross-sectional schematics of different conduits taken along a plane that is perpendicular to a longitudinal axis of the conduits, according to different embodiments.

DETAILED DESCRIPTION

Figure 3:
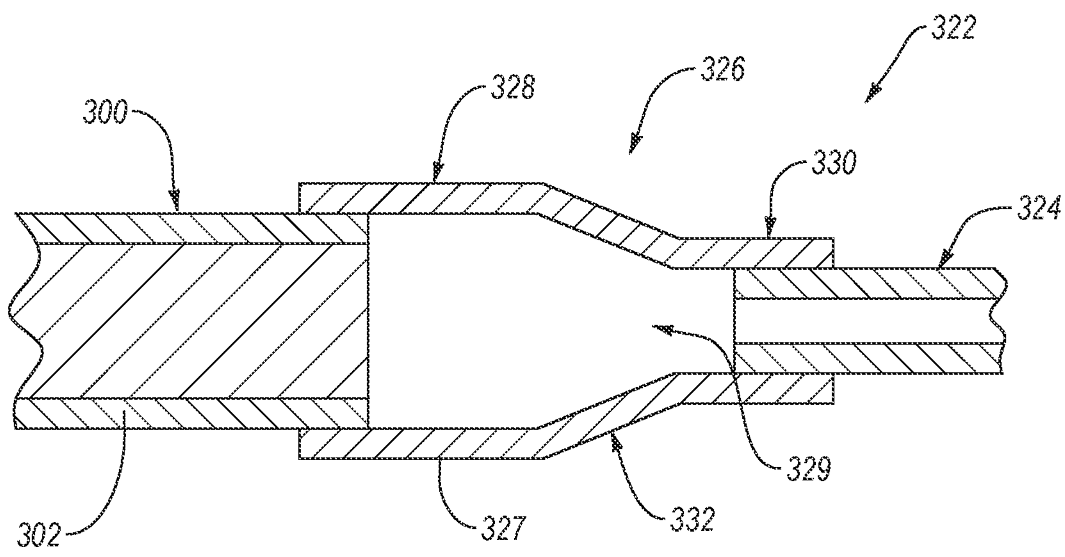
FIG. 3 is a schematic cross-sectional view of a portion of a conduit, according to an embodiment.

Embodiments disclosed herein include conduits having at least one conduit porous material, fluid collection assemblies and systems including the same, and methods of using and forming the same. An example conduit includes at least one wall at least partially defining at least an inlet, and outlet downstream from the inlet, and a passageway extending from the inlet to the outlet. The conduit also includes at least one conduit porous material disposed in the passageway. The conduit porous material may at least partially occupy the passageway and may extend along at least a portion of a length of the conduit measured from the inlet to the outlet. The conduit may be configured for use in a fluid collection system for collecting one or more bodily fluids (e.g., urine, amniotic fluid, blood, etc.).

The conduits including the conduit porous material may be an improvement over a hollow conduit that does not include the conduit porous material. The hollow conduits may be used in a fluid collection system, such as a fluid collection system that includes a vacuum source. The fluid collection system may include a fluid collection assembly that is configured to receive one or more bodily fluids from a patient. The hollow conduit may be in fluid communication with both the fluid collection assembly and the vacuum source such that a vacuum pressure applied to the hollow conduit by the vacuum source may remove the bodily fluids from the fluid collection assembly. The hollow conduit is configured to prevent collapse thereof when the vacuum pressure is applied thereto since the collapse of the hollow conduit may inhibit the removal of the bodily fluids from the fluid collection assembly. The hollow conduit is configured to prevent collapse thereof by forming the hollow conduit from at least one material exhibiting a Young's modulus (e.g., modulus of elasticity) and/or a thickness that prevent the collapse of the hollow conduit when the vacuum pressure is applied thereto. For example, the hollow conduit may be formed from transparent polyvinyl chloride and the wall thereof may exhibit a thickness (e.g., measured parallel to the diameter thereof) that is greater than about 1.5 mm. It is noted that the hollow conduit may be formed from the same material and/or exhibit the same thickness discussed above even when the hollow conduit is used in a fluid collection system that does not include a vacuum source to prevent a collapse thereof when a mass is disposed thereon.

The hollow conduit may exhibit a limited flexibility when the hollow conduit is configured to prevent the collapse thereof. The limited flexibility of the hollow conduits may create several issues. In an example, the hollow conduits may exhibit a limited amount of bending without kinking due the limited flexibility thereof. Similar to the collapsing of the hollow conduit, kinking the hollow conduit inhibits the bodily fluids from being removed from the fluid collection assembly to which the hollow conduit is attached. The limited amount of bending of the hollow conduit may limit the locations where the conduit may be placed and may require longer lengths. In an example, the limited flexibility of the hollow conduit may make conforming the fluid collection assembly to the region about the urethral opening of the patient (e.g., an individual using the fluid collection assembly) difficult. For instance, the hollow conduit may be at least partially disposed within the fluid collection assembly. The fluid collection assembly may be bent to conform to the shape of the urethral opening which may minimize bodily fluids from leaking from the fluid collection assembly. However, the limited flexibility of the hollow conduit may at least one of resist bending of the fluid collection assembly, may kink when the fluid collection assembly is bent, or cause the fluid collection assembly to straighten or otherwise unbend.

As previously discussed, the conduits that include at least one conduit porous material disposed in passageway thereof resolve at least some of the issues of the hollow conduit discussed above. In an example, the conduit porous material provides support to the wall of the conduit, thereby decreasing the likelihood that the conduit collapses when the vacuum pressure is applied thereto. As such, the conduits disclosed herein may be formed from a material exhibiting a Young's modulus that is less than and/or a thickness that is less than the hollow conduit. The lower Young's modulus and/or thickness of the conduits disclosed herein allows such conduits to exhibit a flexibility that is greater than the hollow conduit. Further, even if the conduits disclosed herein exhibit a flexibility that is comparable to the hollow conduits, the conduit porous material provides support to the wall of the conduit such that the conduit is less likely to kink when bent compared to the hollow conduit. The increased flexibility and/or kinking resistance of the conduits that include at least one conduit porous material may also allow such conduits to be more comfortable for a patient compared to the hollow conduits.

FIG. 1 is a cross-sectional schematic of a conduit 100, according to an embodiment. The conduit 100 includes at least one wall 102. The wall 102 defines at least an inlet 104, and outlet 106 downstream from the inlet 104, and a passageway 108 extending from the inlet 104 to the outlet 106. The inlet 104 may be configured to be connected to, disposed in a chamber of, or otherwise in fluid communication with (e.g., via another conduit) a fluid collection assembly (not shown). The outlet 106 is configured to be connected to or otherwise in fluid communication with (e.g., via another conduit or a fluid storage container) a vacuum source (not shown). The passageway 108 forms a fluid flow path that may remove bodily fluids from a fluid collection assembly (not shown) and deposit the removed bodily fluids in a fluid storage container. The conduit 100 also includes at least one conduit porous material 110 disposed in and at least partially occupying the passageway 108. The conduit porous material 110 provides a matrix through which the bodily fluids may flow (e.g., via capillary action) and provides support to the wall 102 thereby inhibiting collapse or kinking of the conduit 100.

The wall 102 may be formed from any suitable fluid impermeable material. In an embodiment, the wall 102 may be formed from a material that is conventionally used to form hollow conduits. In such an embodiment, the fluid impermeable wall 102 may be formed from polyvinyl chloride. In an embodiment, the wall 102 may be formed from one or more materials exhibiting a Young's modulus that is less than polyvinyl chloride. The wall 102 may be formed from a material exhibiting a Young's modulus that is less than polyvinyl chloride since the conduit porous material 110 provides support to the wall 102. Examples of such materials include polyethylene (e.g., low density polyethylene, high density polyethylene, ultrahigh molecular weight polyethylene), polypropylene, polytetrafluoroethylene, nitrile, nylon, ethylene vinyl acetate, a thermoplastic elastomer, or combinations thereof. In an embodiment, the wall 102 may be formed from a material exhibiting a Young's modulus that is greater the polyvinyl chloride. In such an embodiment, the wall 102 may exhibit a thickness that is less than a hollow conduit which allows the conduit 100 to exhibit a flexibility that is less than or equal to a hollow conduit that is formed from polyvinyl chloride. In an embodiment, the wall 102 may be at least partially formed from a fluid impermeable tape. In such an embodiment, the tape may be adhesively attached to the conduit porous material 110.

The wall 102 may exhibit a thickness t measured perpendicular to the longitudinal axis 112 of the conduit 100. The thickness of the wall 102 may be selected based on the desired flexibility of the conduit 100, the strength of the conduit porous material 110, and the Young's modulus of the material(s) that form the wall 102.

In an embodiment, the wall 102 may exhibit a thickness t that is comparable to or greater than a thickness of a hollow conduit conventionally used in fluid collection systems, such as a thickness t that is about 1.5 mm or more, about 1.6 mm or more, about 1.7 mm or more, about 1.8 mm or more, about 1.9 mm or more, about 2 mm or more, about 2.25 mm or more, about 2.5 mm or more, about 3 mm or more, or in ranges of about 1.5 mm to about 1.7 mm, about 1.6 mm to about 1.8 mm, about 1.7 mm to about 1.9 mm, about 1.8 mm to about 2 mm, about 1.9 mm to about 2.25 mm, about 2 mm to about 2.5 mm, or about 2.25 mm to about 3 mm. The wall 102 may exhibit a thickness that is comparable to or greater than a hollow conduit because at least one of the conduit porous material 110 inhibits kinking of the conduit 100 compared to the hollow conduit or the wall 102 may be formed from a material exhibiting a Young's modulus that is less than polyvinyl chloride. Selecting the wall 102 to exhibit a thickness t that is comparable to or greater than the hollow conduit allows at least one of the conduit 100 to have larger vacuum pressures applied thereto without collapsing, the wall 102 to be formed from materials exhibiting a Young's modulus that is significantly less than polyvinyl chloride (i.e., the wall 102 may be formed from a greater variety of materials), the conduit porous material 110 to be formed from relatively flimsy material(s) (e.g., a material exhibiting a relatively low yield strength, relatively low Young's modulus, and/or a relatively high porosity) such that the conduit porous material 110 does not provide much support to the wall 102, the wall 102 may be formed from a hollow conduit that is commonly used and readily available, or the conduit 100 to be used with inlets and outlets that are configured to be used with the hollow conduits.

In an embodiment, the wall 102 may exhibit a thickness t that is less than the hollow conduit. For example, the wall 102 may exhibit a thickness that is about 0.05 mm or less, about 0.1 mm or less, about 0.15 mm or less, about 0.2 mm or less, about 0.25 mm or less, about 0.3 mm or less, about 0.35 mm or less, about 0.4 mm or less, about 0.45 mm or less, about 0.5 mm or less, about 0.6 mm or less, about 0.7 mm or less, about 0.8 mm or less, about 0.9 mm or less, about 1 mm or less, about 1.1 mm or less, about 1.2 mm or less, about 1.3 mm or less, about 1.4 mm or less, about 1.5 mm or less, or in ranges of about 0.05 mm to about 0.15 mm, about 0.1 mm to about 0.2 mm, about 0.15 mm to about 0.25 mm, about 0.2 mm to about 0.3 mm, about 0.25 mm to about 0.35 mm, about 0.3 mm to about 0.4 mm, about 0.35 mm to about 0.45 mm, about 0.4 mm to about 0.5 mm, about 0.45 mm to about 0.6 mm, about 0.5 mm to about 0.7 mm, about 0.6 mm to about 0.8 mm, about 0.7 mm to about 0.9 mm, about 0.8 mm to about 1 mm, about 0.9 mm to about 1.1 mm, about 1 mm to about 1.2 mm, about 1.1 mm to about 1.3 mm, about 1.2 mm to about 1.4 mm, or about 1.3 mm to about 1.5. The wall 102 disclosed herein may be able to exhibit such small thicknesses because of the support provided from the conduit porous material 110 to the wall 102, even when the wall 102 may be formed from material(s) that exhibit a Young's modulus that is less than polyvinyl chloride.

In an embodiment, the wall 102 may be formed from a film. As used herein, the wall 102 is a "film" when the thickness t of the wall 102 is less than 0.75 mm, more particularly less than about 0.5 mm, or more particularly less than about 0.3 mm. The flexibility of the conduit 100 significantly increases, compared to a hollow conduit, when the wall 102 is a film. For example, the wall 102 substantially prevents kinky and presents little to no resistance to bending of the fluid collection assembly when the wall 102 is a film.

As previously discussed, the wall 102 defines a passageway 108 and at least a portion of the passageway 108 is occupied by the at least one conduit porous material 110. The conduit porous material 110 may provide support to the wall 102 to inhibit collapse and kinking of the conduit 100 when a vacuum pressure is applied to the conduit 100 and when the conduit 100 is bent, respectively. The conduit porous material 110 may also direct the bodily fluids that are pulled into the conduit 100 (e.g., via the vacuum pressure or capillary action) towards the outlet 106. The conduit porous material 110 may define a plurality of interconnected pores through which the bodily fluids may flow.

The conduit porous material 110 may include any suitable conduit porous material. In an example, the conduit porous material 110 may be formed from a fabric, such as a silk, linen, or cotton gauze. In an example, the conduit porous material 110 may be formed from a porous polymer (e.g., nylon, polyester, polyurethane, polyethylene, polypropylene, etc.) structure or an open cell foam, spun nylon fiber, a natural material (e.g., cotton, wool, silk, or combinations thereof), compression gauze, paper, terry cloth, pumice, any other suitable material, or combinations thereof. In an example, the conduit porous material 110 may be formed from spun nylon fibers. In an example, the conduit porous material 110 may be formed from a non-woven material, such as at least one of carded webs, needle punched webs, air laid webs, spunlaced webs, vertical lapped nonwoven fabrics, horizontal lapped nonwoven fabrics, or crossed lapped nonwoven fabrics. The nonwoven fabric may be formed from fibers that include at least one of polyester, polypropylene, polyurethane, polyolefin, polycarbonate, polyvinyl chloride, polyacrylic, nylon, other synthetic fibers, one or more natural fibers (e.g., low grade cotton waste), hollow fibers, or combinations thereof. Such nonwoven fabrics may exhibit a high porosity which allows the bodily fluids to flow therein while also providing sufficient support to the wall 102 to prevent collapse and kinking of the conduit 100. Examples of non-woven materials are disclosed in U.S. Provisional Patent Application No. 63/134,754 filed on Jan. 7, 2021, the disclosure of which is incorporated herein, in its entirety, by this reference.

The conduit porous material 110 may exhibit a percent porosity that is about 20% or greater, about 30% or greater, about 40% or greater, about 50% or greater, about 60% or greater, about 65% or greater, about 70% or greater, about 75% or greater, about 80% or greater, about 85% or greater, about 90% or greater, about 95% or greater, or in ranges of about 20% to about 40%, about 30% to about 50%, about 40% to about 60%, about 50% to about 65%, about 60% to about 70%, about 65% to about 75%, about 70% to about 80%, about 75% to about 85%, about 80% to about 90%, about 85% to about 95%, or about 90% to about 99%. Generally, decreasing the percent porosity of the conduit porous material 110 may increase the amount of support that the conduit porous material 110 provides to the wall 102. In other words, decreasing the percent porosity of the conduit porous material 110 may decrease the likelihood that the conduit 100 collapses when the vacuum pressure is applied thereto or kinks. However, decreasing the percent porosity of the conduit porous material 110 also decreases the flow rate of bodily fluids flowing through the conduit 100. As such, the percent porosity of the conduit porous material 110 may be selected by balancing the ability of the conduit porous material 110 to provide support to the wall 102 while also allowing the bodily fluids to flow therein.

The conduit porous material 110 at least partially occupies the cross-sectional area of the passageway 108, wherein the cross-sectional area of the passageway 108 is taken along a plane that is perpendicular to the longitudinal axis 112 of the conduit 100. The quantity of the cross-sectional area of the passageway 108 that is occupied by the conduit porous material 110 may depend on the method that is used to form the conduit 100. In an embodiment, the conduit porous material 110 substantially completely occupies the cross-sectional area of the passageway 108. In such an embodiment, the conduit 100 may be formed, for example, by co-extruding the wall 102 and the conduit porous material 110 or disposing the wall 102 directly on the conduit porous material 110. The wall 102 may be directly disposed on the conduit porous material 110, for example, when the wall 102 is tape that is adhesively disposed on the conduit porous material 110 or the wall 102 coats an exterior surface of the conduit porous material 110. It is noted that the wall 102 may extend partially into the conduit porous material 110 when the wall 102 is formed as a coating on the conduit porous material 110. In an embodiment, the conduit porous material 110 only partially occupies the cross-sectional area of the passageway 108 (e.g., the conduit porous material 110 exhibits a cross-sectional area that is less than the cross-sectional area of the passageway 108). In such an embodiment, the conduit 100 may be formed, for example, by inserting the conduit porous material 110 into a hollow conduit. The conduit porous material 110 that is inserted into the hollow conduit may exhibit a cross-sectional area that is less than the cross-sectional area of the hollow conduit to minimize friction caused by the conduit porous material 110 contacting the surfaces of the hollow conduit during insertion. It is noted that the conduit porous material 110 may substantially occupy the cross-sectional area of the passageway 108 when the wall 102 is formed (e.g., wrapped) around the conduit porous material 110 or the conduit porous material 110 is inserted into the passageway 108 of a hollow conduit (such an insertion may be more difficult than if the conduit porous material 110 exhibited a cross-sectional area that is less than the passageway 108). It is noted that the conduit 100 may be formed using methods other than those disclosed above, such as disposing the conduit porous material 110 in a hollow conduit and then heat shrinking the hollow conduit or coating the conduit porous material 110 with a fluid impermeable material that forms the wall 102.

In an embodiment, the conduit 100 may be configured such that the conduit 100 is unlikely to collapse when exposed to an expected vacuum pressure. As used herein, the vacuum pressure refers to the gauge pressure, that is, the pressure differential between a location external to and spaced from the passageway 108 and the fluid collection assembly to which the conduit 100 is attached and a location within the passageway. During use, the vacuum pressure applied to the passageway 108 may be about 1 kPa to about 40 kPa depending on the vacuum source that is fluidly coupled to the fluid collection assembly 1040. As such, the wall 102 and the porous material 110 may be selected to be able to withstand such vacuum pressures of about 1 kPa to about 5 kPa, about 2.5 kPa to about 7.5 kPa, about 5 kPa to about 10 kPa, about 7.5 kPa to about 12.5 kPa, about 10 kPa to about 15 kPa, about 12.5 kPa to about 17.5 kPa, about 15 kPa to about 20 kPa, about 17.5 kPa to about 22.5 kPa, about 20 kPa to about 25 kPa, about 22.5 kPa to about 27.5 kPa, about 25 kPa to about 30 kPa, about 27.5 kPa to about 32.5 kPa, about 30 kPa to about 35 kPa, about 32.5 kPa to about 37.5 kPa, or about 35 kPa to about 40 kPa. In some embodiments, the vacuum pressure may be greater than about 40 kPa.

The ability of the conduit 100 to resist collapse when the vacuum pressure is applied to the passageway 108 depends on several factors. Generally, increasing the Young's modulus of the material that forms the wall 102, increasing the Young's modulus of the material that forms the conduit porous material 110, increasing the thickness of the wall 102, increasing the density of the conduit porous material 110, and decreasing the percent porosity of the conduit porous material 110 allows a greater vacuum pressure to be applied to the passageway 108 without significantly increasing the likelihood that the conduit 100 collapses. However, increasing the Young's modulus of the material that forms the wall 102, increasing the Young's modulus of the material that forms the conduit porous material 110, increasing the thickness of the wall 102, increasing the density of the conduit porous material 110, and decreasing the void space in the passageway 108 decreases the flexibility of the conduit 100. As such, selecting the composition of the wall 102, the composition of the conduit porous material 110, the thickness of the wall 102, the density of the conduit porous material 110, and the quantity of void space may be selected by balancing the need to prevent the vacuum pressure from collapsing the conduit 100 while increasing the flexibility of the conduit 100.

The conduit porous material 110 may be selected to exhibit a density of about 5 $kg/m^3$ to about 10 $kg/m^3$, about 7.5 $kg/m^3$ to about 12.5 $kg/m^3$, about 10 $kg/m^3$ to about 15 $kg/m^3$, about 12.5 $kg/m^3$ to about 17.5 $kg/m^3$, about 15 $kg/m^3$ to about 20 $kg/m^3$, about 17.5 $kg/m^3$ to about 22.5 $kg/m^3$, about 20 $kg/m^3$ to about 25 $kg/m^3$, about 22.5 $kg/m^3$ to about 27.5 $kg/m^3$, about 25 $kg/m^3$ to about 30 $kg/m^3$, about 27.5 $kg/m^3$ to about 32.5 $kg/m^3$, about 30 $kg/m^3$ to about 35 $kg/m^3$, about 32.5 $kg/m^3$ to about 37.5 $kg/m^3$, about 35 $kg/m^3$ to about 37.5 $kg/m^3$, about 35 $kg/m^3$ to about 40 $kg/m^3$, about 37.5 $kg/m^3$ to about 42.5 $kg/m^3$, about 40 $kg/m^3$ to about 45 $kg/m^3$, about 42.5 $kg/m^3$ to about 47.5 $kg/m^3$, or about 45 $kg/m^3$ to about 50 $kg/m^3$. Generally, increasing the density of the conduit porous material 110 decreases the likelihood that the conduit 100 collapses when the vacuum pressure is applied thereto. However, increasing the density of the conduit porous material 110 also decreases the flow rate of the bodily fluids flowing therein and decreases the flexibility of the conduit 100. As such, the density of the conduit porous material 110 may be selected by balancing the need to prevent the vacuum pressure from collapsing the conduit 100 while increasing the flexibility of the conduit 100. The density of the conduit porous material 110 may also be selected based on the Young's modulus and the thickness of the wall 102, wherein increasing the Young's modulus and/or thickness of the wall 102 allows the conduit porous material 110 to exhibiting a lower density, and vice versa. It is noted that the void space in the passageway 108 depends, at least in part, on the density of the conduit porous material 110 and whether the porous material 110 occupies substantially all of the cross-sectional area of the passageway 108.

Generally, the average person discharges urine at a rate of about 6 ml/s to about 50 ml/s, such as at a rate of about 10 ml/s to about 25 ml/s. The rate at which the person urinate may vary, such as based on the size of the person and the age of the person. The conduit porous material 110 may be selected to exhibit a flow rate that is comparable to the rate at which the average person discharges urine to prevent oversaturation of the fluid collection assembly to which the conduit 100 is attached with bodily fluids which may cause leaks. For example, the conduit porous material 110 may be selected to exhibit a flow rate that is greater than about 6 ml/s, greater than about 10 ml/s, greater than about 20 ml/s, greater than about 30 ml/s, greater than about 40 ml/s, greater than about 50 ml/s, or in ranges of about 6 ml/s to about 10 ml/s, about 8 ml/s to about 12 ml/s, about 10 ml/s to about 15 ml/s, about 12.5 ml/s to about 17.5 ml/s, about 15 ml/s to about 20 ml/s, about 17.5 ml/s to about 22.5 ml/s, about 20 ml/s to about 25 ml/s, about 22.5 ml/s to about 27.5 ml/s, about 25 ml/s to about 30 ml/s, about 27.5 ml/s to about 35 ml/s, about 30 ml/s to about 40 ml/s, about 35 ml/s to about 45 ml/s, or about 40 ml/s to about 50 ml/s. As used herein, the flow rate may refer to the flow rate of the bodily fluids in the conduit porous material 110 when the conduit porous material 110 is at least one of saturated with the bodily fluids, not saturated with the bodily fluids, any of the vacuum pressures disclosed herein are applied to the passageway 108, or when no vacuum pressure is applied to the passageway 108 (e.g., the bodily fluids flow only due to wicking and/or gravity).

The conduit 100 is illustrated with a break between the inlet 104 and the outlet 106. The break indicates that the conduit 100 may exhibit any length. In an example, the conduit 100 may exhibit a length that is about 1 cm or greater, about 15 cm or greater, about 30 cm or greater, about 45 cm or greater, about 60 cm or greater, about 75 cm or greater, about 90 cm or greater, about 105 cm or greater, about 120 cm or greater, about 150 cm or greater, about 180 cm or greater, 210 cm or greater, about 240 cm or greater, about 265 cm or greater, about 300 cm or greater, or in ranges of about 1 cm to about 30 cm, about 15 cm to about 45 cm, about 30 cm to about 60 cm, about 45 cm to about 75 cm, about 60 cm to about 90 cm, about 75 cm to about 105 cm, about 90 cm to about 120 cm, about 105 cm to about 150 cm, about 120 cm to about 180 cm, about 150 cm to about 210 cm, about 180 cm to about 240 cm, about 210 cm to about 265 cm, or about 240 cm to about 300 cm. For example, the conduit 100 may exhibit a length of about 1 cm to about 15 cm when the conduit 100 forms a bendable elbow connector between a hollow conduit and another hollow conduit or a fluid collection assembly, a length of about 10 cm to about 40 cm when the conduit 100 is predominately disposed only in a fluid collection assembly, or a length greater than about 35 cm when the conduit 100 extends a significantly distance from the fluid collection assembly.

The passageway 108 may exhibit a maximum lateral dimension LD measured perpendicularly to the longitudinal axis 112. The maximum lateral dimension LD may be the diameter of the passageway 108 when the passageway 108 exhibits a generally cylindrical shape. The maximum lateral dimension LD may be selected to be about 4 mm or greater, about 5 mm or greater, about 6 mm or greater, about 7 mm or greater, about 8 mm or greater, about 9 mm or greater, about 10 mm or greater, about 12 mm or greater, about 14 mm or greater, about 16 mm or greater, about 18 mm or greater, about 20 mm or greater, about 25 mm or greater, or in ranges of about 4 mm to about 6 mm, about 5 mm to about 7 mm, about 6 mm to about 8 mm, about 7 mm to about 9 mm, about 8 mm to about 10 mm, about 9 mm to about 12 mm, about 10 mm to about 14 mm, about 12 mm to about 16 mm, about 14 mm to about 18 mm, about 16 mm to about 20 mm, or about 18 mm to about 25 mm. The maximum lateral dimension LD may be selected based on a number of factors. In an example, the maximum lateral dimension LD may be selected based on the desired flow rate of bodily fluids in the passageway 108, wherein increasing the maximum lateral dimension $L_D$ increases the flow rate (e.g., $Q=A*v$ where Q is the flow rate, A is the cross-sectional area, and v is the velocity of the bodily fluids in the passageway 108). In an example, the maximum lateral dimension LD is selected based on the device. As used herein, the device(s) refers to the device(s) to which the conduits disclosed herein are, can be, or are configured to be attached to and may include the inlet and/or outlet of at least one of a fluid collection assembly, a fluid storage container, a vacuum source, or a hollow conduit. For instance, the maximum lateral dimension LD may be selected to be slightly smaller (e.g., the conduit 100 expands), equal to, or slightly larger than the dimension of the device if the conduit 100 forms a female attachment with the device. Also, the maximum lateral dimension LD may be selected to be smaller than the dimension of the device when the conduit 100 forms a male attachment with the device. However, it is noted that the conduit 100 may be configured to be attached to an adapter (e.g., the adaptor 326 illustrated in FIG. 3) that allows the conduit 100 to be attached to a device even if the dimensions of the conduit 100 are significantly different than the dimensions of the device.

Figures 8, 9, 10:
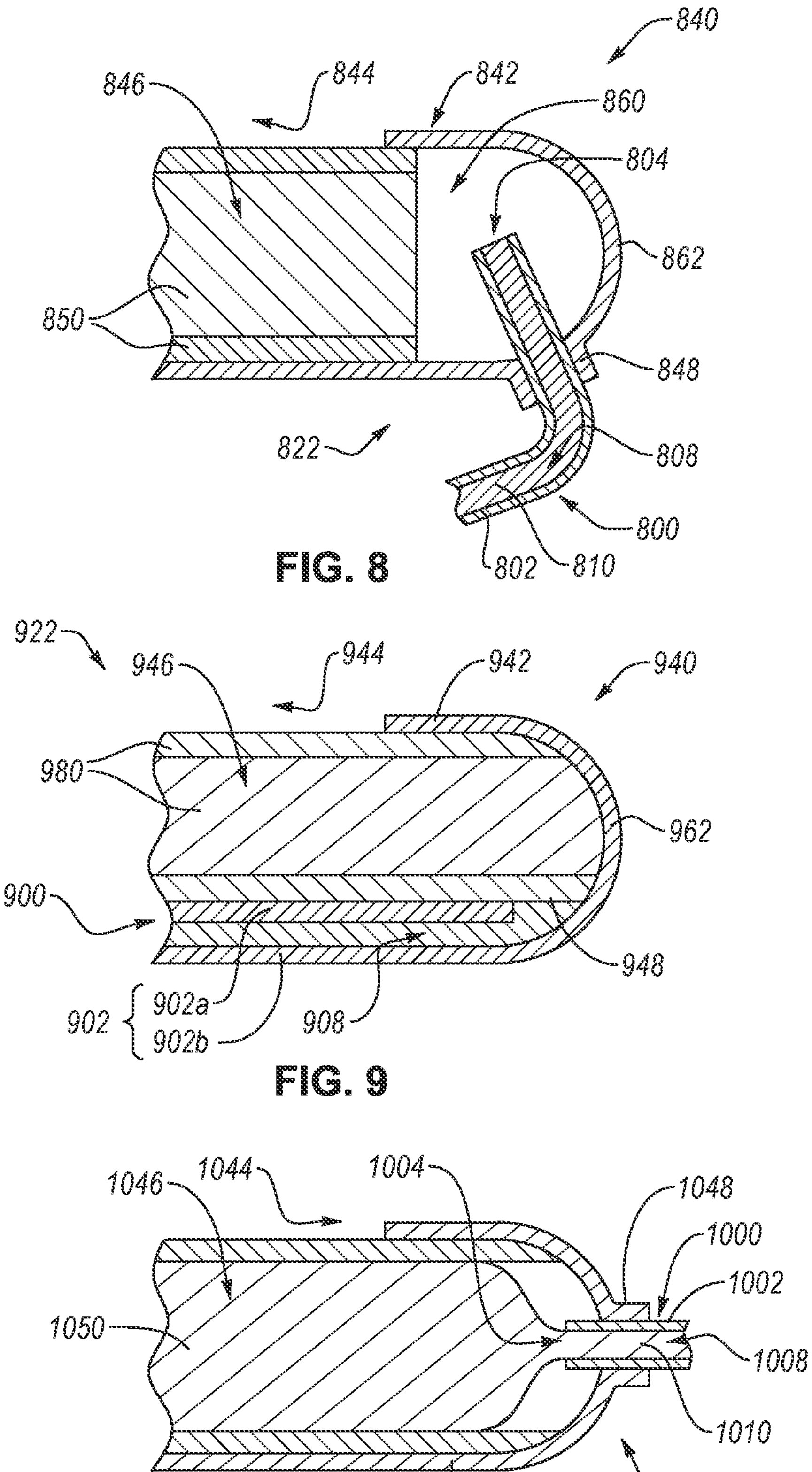
FIG. 8 is a cross-sectional schematic of a portion of a fluid collection system that includes a conduit in fluid communication with a fluid collection assembly, according to an embodiment.
FIG. 9 is a cross-sectional schematic of a portion of a fluid collection system, according to an embodiment.
FIG. 10 is a cross-sectional schematic of a portion of a fluid collection system, according to an embodiment.

In an embodiment, the conduit porous material 110 is formed from the same porous material that is used in the fluid collection assembly (hereafter referred to as "assembly porous material") to which the conduit 100 is configured to be attached. Forming the conduit porous material 110 form the same material as the assembly porous material may facilitate manufacture of the conduit 100. For example, the assembly porous material is readily available and, thus, a manufacture of a fluid collection system that includes the fluid collection assembly and the conduit 100 does not need to use limited storage space to store two different porous materials. In an example, forming the conduit porous material 110 and the assembly porous material from the same material may allow the conduit porous material 110 to be at least partially formed from scraps of the assembly porous material generated during the manufacture of the fluid collection assembly, or vice versa. In an example, forming the conduit porous material 110 and the assembly porous material from the same material may allow the conduit porous material 110 and the assembly porous material to be integrally formed together, as shown in FIG. 9.

In an embodiment, as illustrated, the conduit porous material 110 extends at least substantially the entire length of the conduit 100. In other words, the conduit porous material 110 extends from or near the inlet 104 to or near the outlet 106. As such, the conduit porous material 110 provides support to substantially all of the wall 102. In an embodiment, the conduit porous material 110 only extends along a portion of the entire length of the conduit 100 which minimizes the quantity of conduit porous material 110 necessary to form the conduit 100. In such an embodiment, the conduit porous material 110 may be positioned in portions of the conduit 100 that are expected to exhibit sharp bends during use. In such example, the conduit porous material 110 may be disposed from or near the inlet 104 and extend a distance of about 15 cm to about 60 cm (e.g., 30 cm to about 45 cm) from the inlet 104 since only such portions of the conduit 100 are likely to have sharp bends formed therein. In an example, a portion of the conduit 100 is disposed in a chamber of a fluid collection assembly and the conduit porous material 110 may be omitted from at least some of the portions of the conduit 100 that are disposed in the chamber of the fluid collection assembly since the fluid collection assembly may limit bending of such portions of the conduit 100.

In an embodiment, the conduit porous material 110 does not extend outwardly from the inlet 104 and/or the outlet 106. For instance, any portions of the conduit porous material 110 that extend outwardly from the inlet 104 and/or the outlet 106 are unable to provide support to the wall 102. Further, any portions of the conduit porous material 110 that extend outwardly from the inlet 104 and/or the outlet 106 may make connecting the conduit 100 to a device difficult since such portions of the conduit porous material 110 may interfere with making connections between the inlet 104 and/or outlet 16 and a device (e.g., fluid collection assembly, another conduit, the fluid storage container, etc.) and would be required to be positioned in the device.

The wall 102 may be configured such that the conduit 100 may exhibit an average radius of curvature without kinking. The average radius of curvature that the wall 102 may exhibit without kinking may be about 0.25 cm or less, about 0.5 cm or less, about 0.75 cm or less, about 1 cm or less, about 1.25 cm or less, about 1.5 cm or less, about 1.75 cm or less, about 2 cm or less, about 2.5 cm or less, about 3 cm or less, or in ranges of about 0.25 cm to about 0.75 cm, about 0.5 cm to about 1 cm, about 0.75 cm to about 1.25 cm, about 1 cm to about 1.5 cm, about 1.25 cm to about 1.75 cm, about 1.5 cm to about 2 cm, about 1.75 cm to about 2.5 cm, or about 2 cm to about 3 cm. The average radius of curvature that the wall 102 may exhibit without kinking may depend on the thickness of the walls 102, the material that forms the wall 102, and the strength of the porous material 110.

In an embodiment, the conduit 100 may include a shape memory material (e.g., a steel, copper, or aluminum wire) disposed therein or attached thereto. The shape memory material is configured to maintain the shape of the conduit 100. For example, the shape memory material may maintain a bent shape of the conduit 100. Examples of shape memory material that may be attached to or disposed in the conduit 100 are disclosed in International Application No. PCT/US2020/042262 filed on Jul. 16, 2020 and U.S. Provisional Patent Application No. 63/094,646 filed on Oct. 21, 2020, the disclosures of each of which are incorporated herein, in its entirety, by this reference.

The conduits disclosed herein may exhibit any suitable cross-sectional shape taken along a plane that is perpendicular to the longitudinal axis of the conduits. FIGS. 2A to 2D are cross-sectional schematics of different conduits taken along a plane that is perpendicular to a longitudinal axis of the conduits, according to different embodiments. Except as otherwise disclosed herein, the conduits illustrated in FIGS. 2A to 2D are the same or substantially similar to any of the conduits disclosed herein. For example, the conduits illustrated in FIGS. 2A to 2D include at least one wall defining an inlet, an outlet downstream from the inlet, a passageway extending from the inlet to the outlet, and at least one conduit porous material disposed in at least a portion of the passageway.

Referring to FIG. 2A, the conduit 200*a* includes at least one wall 202*a* defining a passageway 208*a* and at least one conduit porous material 210*a*. The conduit porous material 210*a* is formed from a sheet. For example, the conduit porous materials disclosed herein are often provided in the form of a sheet.

The sheet of the conduit porous material 210*a* may be rolled up such that the conduit porous material 210*a* exhibits a generally circular cross-sectional shape. In an embodiment, as illustrated, the sheet of the conduit porous material 210*a* is rolled up such that opposing edges 214*a* of the conduit porous material 210*a* are positioned adjacent or proximate to each other. In such an embodiment, the conduit porous material 210*a* may form a central gap 216*a* in the center thereof. Optionally, the conduit porous material 210*a* may also exhibit an outer gap 218*a* between the opposing edges 214*a* of the conduit porous material 210*a*. When the edges 214*a* of the conduit porous material 210*a* are adjacent (e.g., contact) each other, the central gap 216*a* and the outer gap 218*a* may not be directly connected. When the edges 214 of the conduit porous material 210*a* are proximate (e.g., slightly spaced from) each other, the central gap 216*a* and the outer gap 218*a* may be directly connected. The central gap 216*a* and the outer gaps 218*a* increase the void space in the passageway 208*a* through which the bodily fluids may flow thereby increasing the flow rate of the bodily fluids through the passageway 208*a*. In some examples, the conduit 200*a* may include an additional porous material that is configured to be disposed in at least one of the central gap 216*a* or the outer gap 218*a*. The additional porous material may provide additional support to the conduit porous material 210*a* thereby increasing the ability of the conduit 100 to resist collapse and kinks. In an embodiment, not shown, the sheet of the conduit porous material 210*a* may be helically wrapped around itself thereby eliminating or minimizing the size of at least one of the central gap 216*a* or the outer gap 218*a* compared to the bending the conduit porous material 210*a* as shown in FIG. 2A. As such, helically wrapping the conduit porous material 210*a* may strengthen the conduit porous material 210*a* but may decrease the flow rate of the bodily fluids through the passageway 208*a* compared to bending the conduit porous material 210*a* as shown in FIG. 2A.

In some embodiments, regardless if the conduit porous material 210*a* is merely bent or helically wrapped, the conduit porous material 210*a* initially may exhibit a cross-sectional area that is smaller than the cross-sectional area of the passageway 208*a*, as measured along a plane that is perpendicular to a longitudinal axis of the conduit 200*a*. In such embodiments, the conduit porous material 210*a* may be disposed in a hollow conduit to form the conduit 200*a*. After disposing the conduit porous material 210*a* in the hollow conduit, the conduit porous material 210*a* may unbend or unwrap slightly such that the conduit porous material 210*a* presses against the wall 202*a*. In some embodiments, the conduit porous material 210*a* may be bend or wrapped as previously discussed herein. After bending or wrapping the conduit porous material 210*a*, the wall 202*a* may be formed around the conduit porous material 210*a*, for instance, by applying a fluid impermeable tape or coating to the conduit porous material 210*a* to form the conduit 200*a*.

Referring to FIG. 2B, the conduit 200*b* includes at least one wall 202*b* that defines a passageway 208*b*. The wall 202*b* and the passageway 208*b* may exhibit a generally circular cross-sectional shape measured along a plane that is generally perpendicular to the longitudinal axis (not shown) of the conduit 200*b*. The conduit 200*b* also includes at least one conduit porous material 210*b* disposed in the passageway 208*b*. In an example, the at least one conduit porous material 210*b* may exhibit a generally circular cross-sectional shape that corresponds to or is smaller than the generally circular cross-sectional shape of the passageway 208*b*.

Generally, devices are configured to be attached to hollow conduits exhibit a generally circular cross-sectional shape measured perpendicular to the longitudinal axis of the hollow conduits. The generally circular cross-sectional shapes of the conduit 200*a* illustrated in FIG. 2A and the conduit 200*b* illustrated in FIG. 2B may allow the conduits 200*a*, 200*b* to be directly attached (i.e., without an adaptor) to such devices, depending on the dimensions of the conduits 200*a*, 200*b* (e.g., maximum lateral dimension of the passageways thereof). However, the conduits disclosed herein may exhibit any generally non-circular cross-sectional shapes because such conduits may be attached to the devices using adaptors or because the devices are configured to be directly attached to conduits exhibiting a generally non-circular cross-sectional shape. For example, FIG. 2C illustrates a conduit 200*c* that exhibits a generally elongated (e.g., oblong or oval) cross-sectional shape and FIG. 2D illustrates a conduit 200*d* that exhibits a generally rectangular (e.g., square) cross-sectional shape. The conduits disclosed herein may also exhibit any other suitable non-circular cross-sectional shape, such as a generally hexagonal cross-sectional shape or a generally triangular cross-sectional shape.

FIG. 3 is a cross-sectional schematic of a fluid collection system 322, according to an embodiment. The fluid collection system 322 includes a conduit 300. Except as otherwise disclosed herein, the conduit 300 may include any of the conduits disclosed herein. The fluid collection system 322 also includes a device 324. As previously discussed, the device 324 may include an outlet of a fluid collection assembly, an inlet or outlet of a fluid storage container, the inlet or outlet of a vacuum source, or an inlet or outlet of a hollow conduit. The fluid collection system 322 also includes an adaptor 326. The adaptor 326 is configured to extend between and be attached to the device 324 and the conduit 300. In an embodiment, the adaptor 326 includes a conduit portion 328 that is configured to be attached to the conduit 300. The adaptor 326 may be configured to be attached to the conduit 300 using any suitable technique. In an example, the conduit portion 328 is configured to be press fitted to the conduit 300 when the conduit 300 exhibits sufficient rigidity to maintain the connection. When the conduit portion 328 is configured to be press-fitted to the conduit 300, one or more of the conduit portion 328 or the end of the conduit 300 may be tapered which may facilitate the press-fitting therebetween. Further, when the conduit portion 328 is configured to be press-fitted to the conduit 300, the conduit portion 328 may be reversibly attached to the conduit which allows the conduit 300 and the adaptor 326 to be provided separately. Providing the conduit 300 separately allows the conduit 300 to be used with a variety of devices (e.g., a device that may be directly attached to the conduit 300 or indirectly via the adaptor 326). In an example, the conduit portion 328 is permanently attached (e.g., adhesively attached or welded) to the conduit 300. The conduit portion 328 may be permanently attached to the conduit 300, for instance, when the conduit 300 does not exhibit sufficient rigidity to maintain a press-fit attachment between the conduit portion 328 and the conduit 300. Permanently attaching the conduit 300 to the conduit portion 328 only allows the conduit 300 to be indirectly attached to the device 324 and precludes the conduit 300 from being attached to a device to which the conduit 300 may be directly attached. The conduit portion 328 may be configured to form a male attachment with the conduit 300 (e.g., the conduit 300 is disposed in the conduit portion 328) or a female attachment with the conduit 300 (e.g., the conduit portion 328 is disposed in the conduit 300).

In an embodiment, the adaptor 326 is integrally formed with the wall 302 of the conduit 300 and does not include a conduit portion 328. Instead, the adaptor 326 is a portion of the wall 302 that exhibits one or more properties that are different than the rest of the wall 302. The different properties of the adaptor 326 facilitate attachment of the adaptor 326 to the device 324. For example, the different properties may include at least one of an increased rigidity (e.g., an increased thickness), a different cross-sectional shape, or different dimension(s) than the rest of the wall 302. The increased rigidity may facilitate directly press-fitting the conduit 300 to the device 324. The different cross-sectional shape and/or different dimension(s) may corresponds to (e.g., is equal to, slightly larger, or slightly smaller) the cross-sectional shape and/or dimension(s) of the device 324.

The adaptor 326 includes a device portion 330 that is configured to be attached to the device 324. Generally, the device portion 330 is configured to be reversibly attached (e.g., press-fitted) to the device 324. However, the device portion 330 may be configured to be permanently attached to the device 324. The device portion 330 may be configured to form a male attachment with the device (e.g., the device 324 is disposed in the device portion 330) or a female attachment with the device 324 (e.g., the device portion 330 is disposed in the device 324).

In some embodiments, the cross-sectional shape and/or dimension(s) of the conduit 300 are different than the cross-sectional-shape and/or dimension(s) of the device 324, respectively. In such embodiments, the adaptor 326 includes an intermediate portion 332. The intermediate portion 332 changes the cross-sectional shape and/or dimension(s) of the adaptor 326 from the conduit portion 328 to the device portion 330. For example, as illustrated, the dimension(s) of the conduit 300 may be greater than the device 324 and the intermediate portion 332 may be tapered thereby decreasing the dimension(s) of the adaptor 326 from the conduit portion 328 to the device portion 330.

The adaptor 326 includes one or more adaptor walls 327 that form the conduit portion 328, the device portion 330, and the intermediate portion 332. The adaptor walls 327 also define at least one adaptor passageway 329 that is configured to allow the bodily fluids to flow through the adaptor 326 and between the conduit 300 and the device 324. The adaptor walls 327 are formed from a fluid impermeable material to prevent the bodily fluids from leaking through the adaptor walls 327. In an example, the adaptor walls 327 may be formed from any of the fluid impermeable materials disclosed herein. In an example, the adaptor walls 327 may be formed from a rigid material to allow the adaptor 326 to be press-fitted to the conduit 300 and/or the device 324. Examples of such rigid materials include polyvinyl chloride formed without plasticizers, a metal, or another other suitable material.

It is noted that the conduit 300 may be connected to the device 324 without the adaptor 326. In an example, the conduit 300 may exhibit a size and shape that is able to connect directly to the device 324. In an example, the conduit 300 may exhibit a rigidity that allow the conduit 300 to be press-fitted to the device 324. In an example, the conduit 300 may be taped to the device 324.

The conduits illustrated in FIGS. 1-3 are illustrated as including the conduit porous material only disposed in the passageways thereof. In other words, the conduits illustrated in FIGS. 1-3 do not include a conduit porous material extending therefrom. However, in some embodiments (as illustrated in FIGS. 4A-6B), the conduit porous material may extend outwardly from the passageways of the conduits.

Figure 4A:
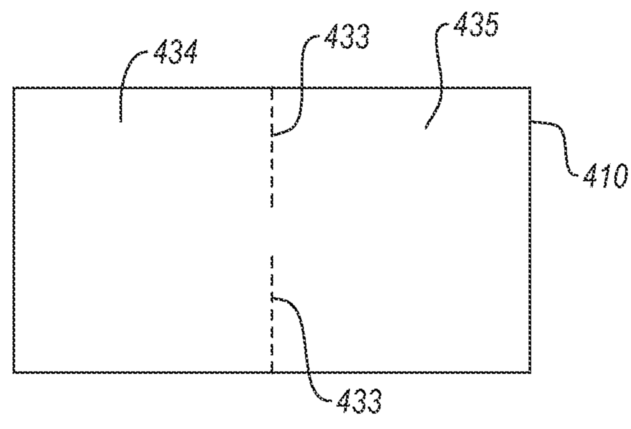
FIGS. 4A and 4B illustrate a method of forming a conduit that includes a conduit porous material extending outwardly from the passageway (illustrated in FIG. 4C), according to an embodiment.
Figure 4B:
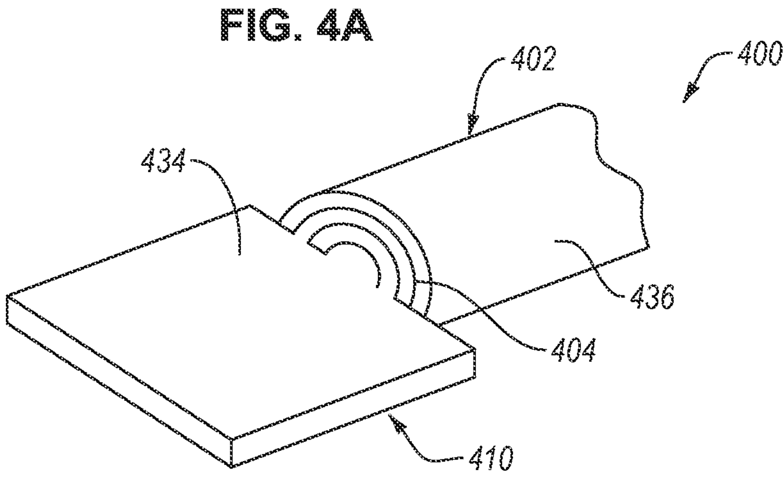

FIGS. 4A and 4B illustrate a method of forming a conduit 400 that includes a conduit porous material 410 extending outwardly from the passageway 408 (illustrated in FIG. 4C), according to an embodiment. In particular, FIG. 4A is a top elevational view of the conduit porous material 410 before forming the conduit 400 and FIG. 4B is an isometric view of the conduit 400 formed using the conduit porous material 410. Except as otherwise disclosed herein, the conduit 400 may be the same or substantially similar to any of the conduits disclosed herein.

Referring to FIG. 4A, the conduit porous material 410 may be provided as a sheet, such as a generally rectangular sheet. Optionally, the conduit porous material 410 may have one or more cuts 433 formed therein. The cuts 434 are schematically illustrated using dashed lines. The cuts 433 divide the conduit porous material 410 into a first portion 434 and a second portion 435. The first portion 434 may form at least a portion of the conduit porous material 410 that extends outwardly from the passageway 408 of the conduit 400 (shown in FIG. 4C) and the second portion 435 may form at least a portion of the conduit porous material 410 that is disposed in the passageway 408 of the conduit 400.

Referring to FIG. 4B, the conduit 400 may be formed by rolling, bunching up, or otherwise collecting the second portion 435 of the conduit porous material 410. The cuts 433 allow the second portion 435 to be rolled, bunched up, or otherwise collected while the first portion 434 remains substantially undisturbed. The walls 402 may be formed around the second portion 435 or the second portion 435 may be positioned within the passageway 408 defined by one or more preformed walls 402. As such, at least a portion of the first portion 434 may extend from the walls 402 of the conduit 400. As will be discussed in more detail below, the first portion 434 may be positioned in the chamber of a fluid collection assembly which may facilitate removal of the bodily fluids from the chamber.

Figure 4C:
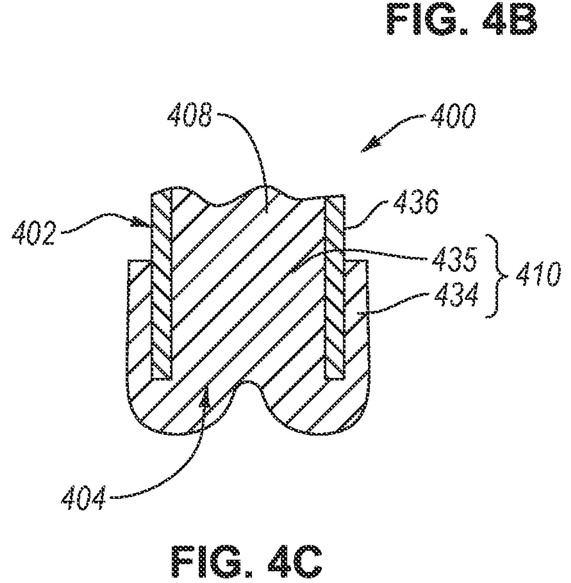
FIG. 4C is a cross-sectional schematic of the conduit when the first portion of the conduit porous material is folded back onto the walls, according to an embodiment.

In an embodiment, the first portion 434 may remain in a generally sheet like configuration (e.g., the first portion 434 is not folded, rolled, bunched up, or otherwise collected). In an embodiment, the first portion 434 may be folded back onto the walls 402 of the conduit 400. For example, FIG. 4C is a cross-sectional schematic of the conduit 400 when the first portion 434 of the conduit porous material 410 is folded back onto the walls 402, according to an embodiment. The first portion 434 may be folded back such that at least a portion of the first portion 434 contacts at least a portion of the outer surface 436 of the walls 402. It has been found that the walls 402 of the conduit 400 are most likely to collapse at or near the inlet 404 of the conduit 400. However, unexpectedly, it has been found that folding the first portion 434 of the conduit porous material 410 back onto the walls 402 of the conduit 400 inhibits collapse of the walls 402 at or near the inlet 404. Further, folding the conduit porous material 410 back onto the walls 402 may decrease the quantity of assembly porous material included in the fluid collection assembly to which the conduit 400 is attached.

It is noted that FIGS. 4A-4C merely illustrate one or more methods of forming a conduit that includes a portion of a conduit porous material extending from the passageway. In an example, the conduit porous material 410 may not be cut. In an example, the conduit porous material 410 may exhibit a non-rectangular sheet-like shape, such as a shape that includes a sheet-like portion attached to a cylindrical portion.

Figure 5:
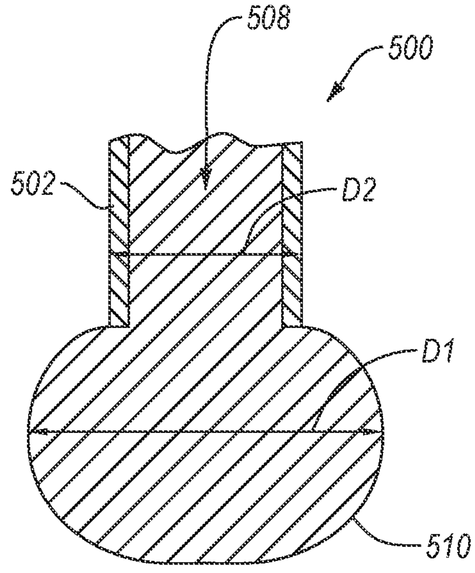
FIG. 5 is an cross-sectional schematic of a conduit that includes a first portion of the conduit porous material extending from the passageway of the conduit, according to an embodiment.

The portion of the conduit porous material extending from the walls and passageway of the conduit may exhibit a shape other than the shape illustrated in FIGS. 4A-4C. For example, FIG. 5 is an cross-sectional schematic of a conduit 500 that includes a first portion 534 of the conduit porous material 500 extending from the passageway 508 of the conduit 500, according to an embodiment. Except as otherwise disclosed herein, the conduit 500 may be the same or substantially similar to any of the conduits disclosed herein. The first portion 534 may be configured to at least partially or substantially occupy a portion of a chamber that is not occupied by the assembly porous material. As such, the first portion 534 may exhibit a generally semi-spherical shape, a bulb-like shape, or another shape that corresponds to the portion of the chamber that is not occupied by the assembly porous material. In an example, the first portion 534 may exhibit a maximum lateral dimension D1 (e.g., diameter) that is greater than a maximum lateral dimension D2 of the walls 502 of the conduit 500 which may help the conduit portion material 510 better occupy the portions of the chamber that are not occupied by the assembly porous material. As will be discussed in more detail below, the shape of the first portion 534 may facilitate flow of the bodily fluids from the assembly porous material to the conduit porous material 510.

The conduit 500 may be formed using any suitable method. In an example, the conduit 500 may be formed using the same method as the conduit 400 illustrated in FIGS. 4A-4C except that the first portion 534 is bunched up, molded, or otherwise collected to form a shape that at least partially or substantially occupies the portion of the chamber that is not occupied by the assembly porous material. In an example, the conduit porous material 510 may be provided while exhibiting the generally semi-spherical shape, a bulb-like shape, or any other suitable shape.

Figure 6A:
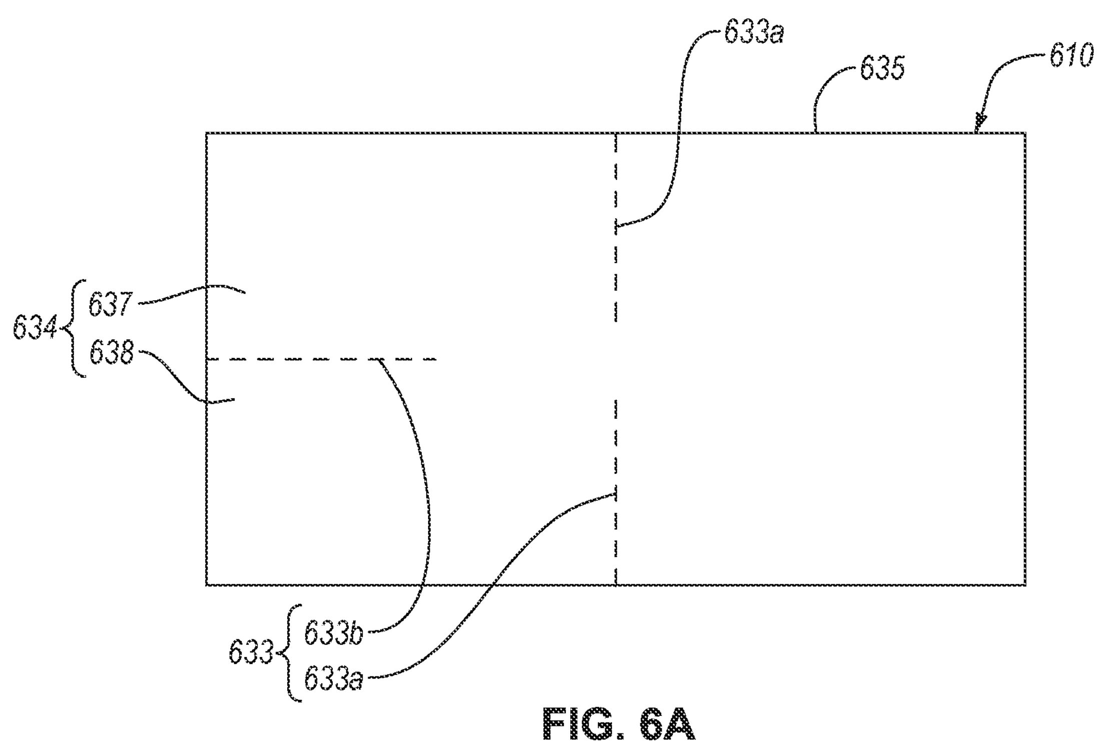
FIGS. 6A and 6B illustrate a method of forming a conduit that includes a conduit porous material extending outwardly from the passageway (not shown, obscured), according to an embodiment.
Figure 6B:
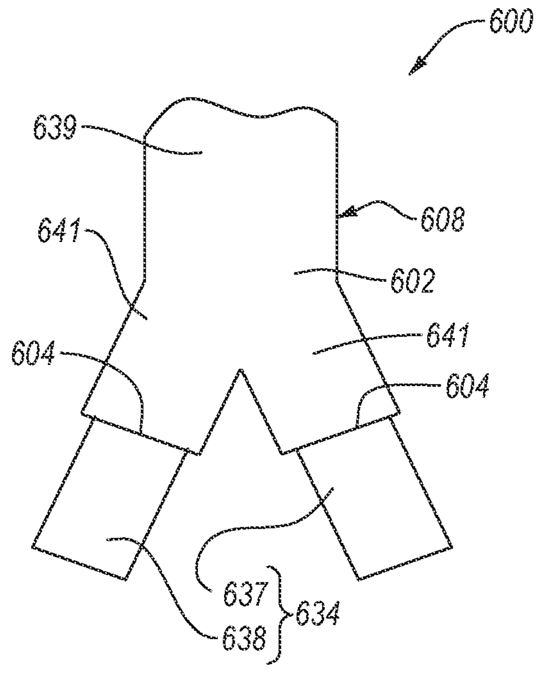

FIGS. 6A and 6B illustrate a method of forming a conduit 600 that includes a conduit porous material 610 extending outwardly from the passageway (not shown, obscured), according to an embodiment. In particular, FIG. 6A is a top elevational view of the conduit porous material 610 before forming the conduit 600 and FIG. 6B is an isometric view of the conduit 600 formed using the conduit porous material 610. Except as otherwise disclosed herein, the conduit 600 may be the same or substantially similar to any of the conduits disclosed herein.

Referring to FIG. 6A, the conduit porous material 610 may be provided as a sheet, such as a generally rectangular sheet. The conduit porous material 610 may have one or more cuts 633 formed therein. The cuts 633 are schematically illustrated using dashed lines. The conduit porous material 610 may have one or more first cuts 633 formed therein that form a first portion 634 and a second portion 635. At least a portion of the first portion 634 is configured to extend from the walls 602 of the conduit 600 and at least a portion of the second portion 635 is configured to be disposed within the passageway of the conduit 600. The conduit porous material 610 may also include one or more second cuts 633 formed therein that separate the first portion 634 into a plurality of regions (e.g., a first region 637 and a second region 638). The plurality of regions may form different and distinct flow paths through which the bodily fluids may flow through the conduit porous material 610. The plurality of regions may also allow the conduit portion material 610 to receive bodily fluids from different locations of the chamber of the fluid collection assembly. In an embodiment, the first and second cuts 633*a*, 633*b* are not parallel (e.g., perpendicular) to each other.

Referring to FIG. 6B, at least a portion of the second portion 635 may be rolled, bunched up, or otherwise collected. The rolled, bunched up, or otherwise collected portions of the second portion 635 may be disposed in a passageway defined by already formed walls 602 or the walls 602 may be formed around the such portions of the second portion 635. In an embodiment, the walls 602 may form a primary branch 639 that includes the first portion 635 disposed in the passageway defined thereby. The walls 602 may also include one or more secondary branches 641 extending from the primary branch 639. For example, the walls 602 may include secondary branches 641 for each of the regions of the first portion 634. The secondary branches 641 may define passageways that include a portion of the first portion 634 disposed therein. Each of the secondary branches 641 may define an inlet 604 and a remainder of the first portion 634 not disposed in the passageways defined by the secondary branches 641 may extend from the inlet 604. The secondary branches 641 may minimize diffusion of a vacuum pressure through all of the first portion 634 thereby concentrating the vacuum pressure at the uncovered portions of the conduit porous material 610. In an embodiment, each of the secondary branches 641 may extend the same distance from the primary branch 639. In an embodiment, at least one of the secondary branches 641 may extend a distance from the primary branch 639 that is different than at least one other secondary branch 641.

Figure 7A:
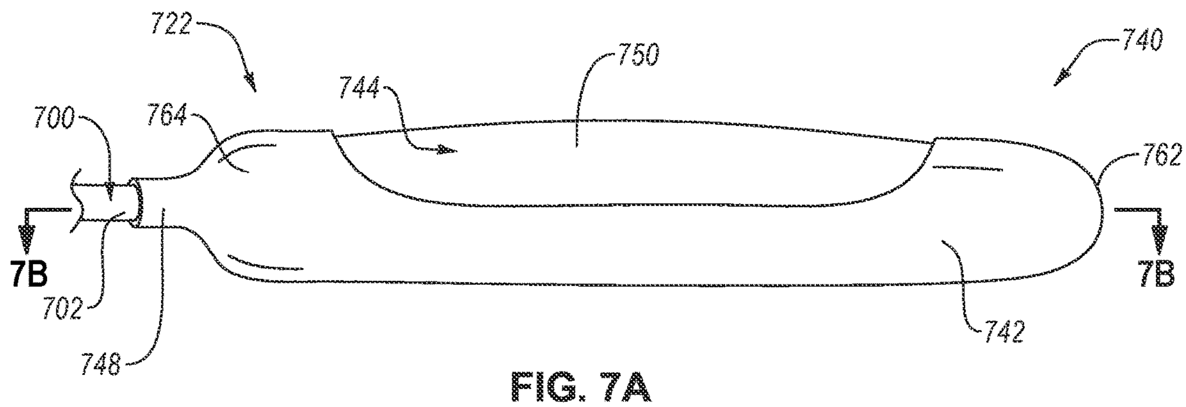
FIG. 7A is an isometric view of a portion of a fluid collection system that includes a fluid collection assembly that is in fluid communication with a conduit, according to an embodiment.
Figure 7B:
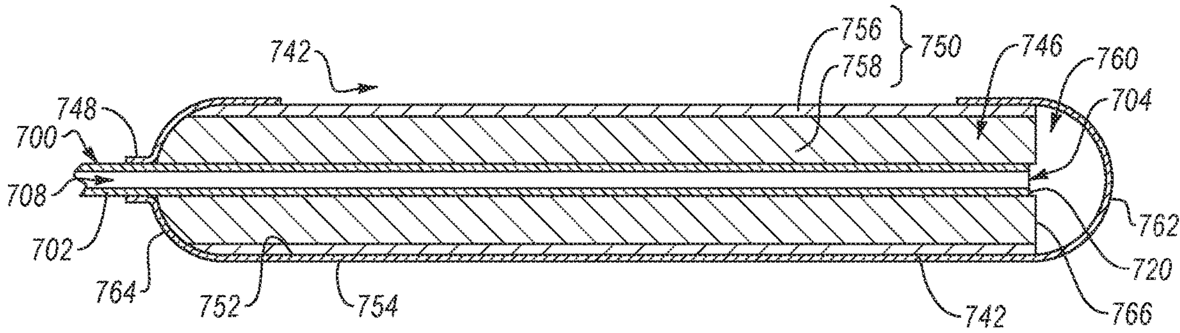
FIG. 7B is a cross-sectional schematic of the fluid collection system taken along plane 7B-7B shown in FIG. 7A, according to an embodiment.

As previously discussed, the conduits disclosed herein may be used with fluid collection assemblies. FIG. 7A is an isometric view of a portion of a fluid collection system 722 that includes a fluid collection assembly 740 that is in fluid communication with a conduit 700, according to an embodiment. FIG. 7B is a cross-sectional schematic of the fluid collection system 722 taken along plane 7B-7B shown in FIG. 7A, according to an embodiment. The fluid collection assembly 740 is an example of a female fluid collection assembly for receiving and collecting bodily fluids from a female. The fluid collection assembly 740 includes a fluid impermeable barrier 742 defining at least an opening 744, a chamber 746, and a fluid outlet 748. The fluid collection assembly 740 also includes at least one assembly porous material 750 disposed in a chamber 746. The conduit 700 is disposed through the fluid outlet 748 such that an inlet 704 of the conduit 700 is disposed in the chamber 746. Except as otherwise disclosed herein, the conduit 700 may be the same or substantially similar to any of the conduits disclosed herein.

The fluid impermeable barrier 742 at least partially defines a chamber 746 (e.g., interior region) and an opening 744. For example, the interior surface(s) 752 of the fluid impermeable barrier 742 at least partially defines the chamber 746 within the fluid collection assembly 740. The fluid impermeable barrier 742 temporarily stores the bodily fluids in the chamber 746. The fluid impermeable barrier 742 may be formed of any suitable fluid impermeable material(s), such as a fluid impermeable polymer (e.g., silicone, polypropylene, polyethylene, polyethylene terephthalate, neoprene, a polycarbonate, etc.), a metal film, natural rubber, another suitable material, any other fluid impermeable material disclosed herein, or combinations thereof. As such, the fluid impermeable barrier 742 substantially prevents the bodily fluids from passing through the fluid impermeable barrier 742. In an example, the fluid impermeable barrier 742 may be air permeable and fluid impermeable. In such an example, the fluid impermeable barrier 742 may be formed of a hydrophobic material that defines a plurality of pores. At least one or more portions of at least an outer surface 754 of the fluid impermeable barrier 742 may be formed from a soft and/or smooth material, thereby reducing chaffing.

In some examples, the fluid impermeable barrier 742 may be tubular (ignoring the opening), such as substantially cylindrical (as shown), oblong, prismatic, or flattened tubes. During use, the outer surface 754 of the fluid impermeable barrier 742 may contact the patient. The fluid impermeable barrier 742 may be sized and shaped to fit between the labia and/or the gluteal cleft between the legs of a female user.

The opening 744 provides an ingress route for fluids to enter the chamber 746. The opening 744 may be defined by the fluid impermeable barrier 742 such as by an inner edge of the fluid impermeable barrier 742. For example, the opening 744 is formed in and extends through the fluid impermeable barrier 742, from the outer surface 754 to the inner surface 752, thereby enabling bodily fluids to enter the chamber 746 from outside of the fluid collection assembly 740. The opening 744 may be an elongated hole in the fluid impermeable barrier 742. For example, the opening 744 may be defined as a cut-out in the fluid impermeable barrier 742. The opening 744 may be located and shaped to be positioned adjacent to a female urethra.

The fluid collection assembly 740 may be positioned proximate to the female urethral opening and the bodily fluids may enter the chamber 746 of the fluid collection assembly 740 via the opening 744. The fluid collection assembly 740 is configured to receive the bodily fluids into the chamber 746 via the opening 744. When in use, the opening 744 may have an elongated shape that extends from a first location below the urethral opening (e.g., at or near the anus or the vaginal opening) to a second location above the urethral opening (e.g., at or near the top of the vaginal opening or the pubic hair).

The opening 744 may have an elongated shape because the space between the legs of a female is relatively small when the legs of the female are closed, thereby only permitting the flow of the bodily fluids along a path that corresponds to the elongated shape of the opening 744 (e.g., longitudinally extending opening). The opening 744 in the fluid impermeable barrier 742 may exhibit a length that is measured along the longitudinal axis of the fluid collection assembly 740 that may be at least about 10% of the length of the fluid collection assembly 740, such as about 10% to about 30%, about 25% to about 40%, about 30% to about 60%, about 50% to about 75%, about 65% to about 85%, or about 75% to about 95% of the length of the fluid collection assembly 740.

The opening 744 in the fluid impermeable barrier 742 may exhibit a width that is measured transverse to the longitudinal axis of the fluid collection assembly 740 that may be at least about 10% of the circumference of the fluid collection assembly 740, such as about 10% to about 30%, about 25% to about 40%, about 30% to about 60%, about 50% to about 75%, about 65% to about 85%, or about 75% to about 100% of the circumference of the fluid collection assembly 740. The opening 744 may exhibit a width that is greater than 70% of the circumference of the fluid collection assembly 740 since the vacuum (e.g., suction) through the conduit 700 pulls the fluid through the assembly porous material 750 and into the conduit 700. In some examples, the opening 744 may be vertically oriented (e.g., having a major axis parallel to the longitudinal axis of the fluid collection assembly 740). In some examples (not shown), the opening 744 may be horizontally oriented (e.g., having a major axis perpendicular to the longitudinal axis of the fluid collection assembly 740). In an example, the fluid impermeable barrier 742 may be configured to be attached to the patient, such as adhesively attached (e.g., with a hydrogel adhesive) to the patient. According to an example, a suitable adhesive is a hydrogel layer.

In some examples, the fluid impermeable barrier 742 may define a fluid outlet 748 sized to receive the conduit 700. The at least one conduit 700 may be disposed in the chamber 746 via the fluid outlet 748. The fluid outlet 748 may be sized and shaped to form an at least substantially fluid tight seal against the conduit 700 or the at least one tube thereby substantially preventing the bodily fluids from escaping the chamber 746. It is noted that the fluid outlet 748 may be sized and shape to form an at least substantially fluid tight seal against an adaptor (e.g., adaptor 326 of FIG. 3).

The fluid impermeable barrier 742 may include markings thereon, such as one or more markings to aid a user in aligning the fluid collection assembly 740 on the patient. For example, a line on the fluid impermeable barrier 742 (e.g., opposite the opening 744) may allow a healthcare professional to align the opening 744 over the urethra of the patient. In examples, the markings may include one or more of alignment guide or an orientation indicator, such as a stripe or hashes. Such markings may be positioned to align the fluid collection assembly 740 to one or more anatomical features such as a pubic bone, etc.

The fluid collection assembly 740 includes assembly porous material 750 disposed in the chamber 746. The assembly porous material 750 may cover at least a portion (e.g., all) of the opening 744. The assembly porous material 750 may include a fluid permeable membrane 756 and a fluid permeable support 758. The assembly porous material 750 is exposed to the environment outside of the chamber 746 through the opening 744. In an embodiment, the assembly porous material 750 may be configured to wick any bodily fluids away from the opening 744, thereby preventing the bodily fluids from escaping the chamber 746. The permeable properties referred to herein may be wicking, capillary action, diffusion, or other similar properties or processes, and are referred to herein as "permeable" and/or "wicking." Such "wicking" and/or "permeable" properties may not include absorption of the bodily fluids into at least a portion of the wicking material, such as not include adsorption of the bodily fluids into the fluid permeable support 758. Put another way, substantially no absorption or solubility of the bodily fluids into the material may take place after the material is exposed to the bodily fluids and removed from the bodily fluids for a time. While no absorption or solubility is desired, the term "substantially no absorption" may allow for nominal amounts of absorption and/or solubility of the bodily fluids into the wicking material (e.g., absorbency), such as less than about 30 wt % of the dry weight of the wicking material, less than about 20 wt %, less than about 10 wt %, less than about 7 wt %, less than about 5 wt %, less than about 3 wt %, less than about 2 wt %, less than about 1 wt %, or less than about 0.5 wt % of the dry weight of the wicking material. The wicking material may also wick the bodily fluids generally towards an interior of the chamber 746, as discussed in more detail below. In an embodiment, the assembly porous material 750 may include at least one absorbent or adsorbent material.

In an embodiment, the assembly porous material 750 may include the fluid permeable membrane 756 disposed in the chamber 746. The fluid permeable membrane 756 may cover at least a portion (e.g., all) of the opening 744. The fluid permeable membrane 756 may be composed to wick the bodily fluids away from the opening 744, thereby preventing the bodily fluids from escaping the chamber 746.

In an embodiment, the fluid permeable membrane 756 may include any material that may wick the bodily fluids. For example, the fluid permeable membrane 756 may include fabric, such as a gauze (e.g., a silk, linen, or cotton gauze), another soft fabric, another smooth fabric, or any of the other porous materials disclosed herein. Forming the fluid permeable membrane 756 from gauze, soft fabric, and/or smooth fabric may reduce chaffing caused by the fluid collection assembly 740.

The fluid collection assembly 740 may include the fluid permeable support 758 disposed in the chamber 746. The fluid permeable support 758 is configured to support the fluid permeable membrane 756 since the fluid permeable membrane 756 may be formed from a relatively foldable, flimsy, or otherwise easily deformable material. For example, the fluid permeable support 758 may be positioned such that the fluid permeable membrane 756 is disposed between the fluid permeable support 758 and the fluid impermeable barrier 742. As such, the fluid permeable support 758 may support and maintain the position of the fluid permeable membrane 756. The fluid permeable support 758 may include any material that may wick, absorb, adsorb, or otherwise allow fluid transport of the bodily fluids, such as any of the fluid permeable membrane materials disclosed herein above. For example, the fluid permeable membrane material(s) may be utilized in a more dense or rigid form than in the fluid permeable membrane 756 when used as the fluid permeable support 758. The fluid permeable support 758 may be formed from any fluid permeable material that is less deformable than the fluid permeable membrane 756. For example, the fluid permeable support 758 may include a porous polymer (e.g., nylon, polyester, polyurethane, polyethylene, polypropylene, etc.) structure or an open cell foam, such as spun nylon fiber. In some examples, the fluid permeable support 758 may be formed from a natural material, such as cotton, wool, silk, or combinations thereof. In such examples, the material may have a coating to prevent or limit absorption of fluid into the material, such as a water repellent coating. In some examples, the fluid permeable support 758 may be formed from fabric, felt, gauze, or combinations thereof.

In some examples, the fluid permeable membrane 756 may be optional. For example, the assembly porous material 750 may include only the fluid permeable support 758. In some examples, the fluid permeable support 758 may be optionally omitted from the fluid collection assembly 740. For example, the assembly porous material 750 may only include the fluid permeable membrane 756.

In an embodiment, the fluid permeable support 758 may be hydrophobic. The fluid permeable support 758 may be hydrophobic when the fluid permeable support 758 exhibits a contact angle with water (a major constituent of bodily fluids) that is greater than about 90°, such as in ranges of about 90° to about 120°, about 105° to about 135°, about 120° to about 150°, about 135° to about 175°, or about 150° to about 180°. The hydrophobicity of the fluid permeable support 758 may limit absorption, adsorption, and solubility of the bodily fluids in the fluid permeable support 758 thereby decreasing the amount of bodily fluids held in the assembly porous material 750. In an embodiment, the fluid permeable membrane 756 is hydrophobic or hydrophilic. In an embodiment, the fluid permeable support 758 is more hydrophobic (e.g., exhibits a larger contact angle with water) than the fluid permeable membrane 756. The lower hydrophobicity of the fluid permeable membrane 756 may help the assembly porous material 750 receive the bodily fluids from the urethral opening while the hydrophobicity of the fluid permeable support 758 limits the bodily fluids that are retained in the assembly porous material 750.

In an embodiment, the assembly porous material 750 includes a nonwoven material instead of or in addition to at least one of the fluid permeable membrane 756 or the fluid permeable support. Examples of nonwoven materials that may be included in the assembly porous material 750 are disclosed in U.S. Provisional Patent Application No. 63/134,754 filed on Jan. 7, 2021, the disclosure of which was previously incorporated herein.

The assembly porous material 750 may at least substantially completely fill the portions of the chamber 746 that are not occupied by the conduit 700. In some examples, the assembly porous material 750 may not substantially completely fill the portions of the chamber 746 that are not occupied by the conduit 700. In such an example, the fluid collection assembly 740 includes the reservoir 760 (FIG. 1B) disposed in the chamber 746.

The reservoir 760 is a substantially unoccupied portion of the chamber 746. The reservoir 760 may be defined between the fluid impermeable barrier 742 and one or both of the fluid permeable membrane 756 and fluid permeable support 758. The bodily fluids that are in the chamber 746 may flow through the fluid permeable membrane 756 and/or fluid permeable support 758 to the reservoir 760. The reservoir 760 may retain of the bodily fluids therein.

The bodily fluids that are in the chamber 746 may flow through the fluid permeable membrane 756 and/or fluid permeable support 758 to the reservoir 760. The fluid impermeable barrier 742 may retain the bodily fluids in the reservoir 760. While depicted in the distal end region 762, the reservoir 760 may be located in any portion of the chamber 746 such as the proximal end region 764. The reservoir 760 may be located in a portion of the chamber 746 that is designed to be located in a gravimetrically low point of the fluid collection assembly when the fluid collection assembly is worn.

In some examples (not shown), the fluid collection assembly 740 may include multiple reservoirs, such as a first reservoir that is located at the portion of the chamber 746 closest to the inlet of the conduit 700 (e.g., distal end region 762) and a second reservoir that is located at the portion of the of the chamber 746 that is at or near proximal end region 764). In another example, the fluid permeable support 758 is spaced from at least a portion of the conduit 700, and the reservoir 760 may be the space between the fluid permeable support 758 and the conduit 700.

The conduit 700 may be at least partially disposed in the chamber 746. The conduit 700 may be used to remove the bodily fluids from the chamber 746. The conduit 700 at least one wall 702 defining an inlet 704, an outlet (not shown) downstream from the inlet 704, and a passageway 708. The passageway 708 may be at least partially occupied by at least one conduit porous material 710. The outlet of the conduit 700 may be operably coupled to a vacuum source, such as a vacuum pump for withdrawing fluid from the chamber 746 through the conduit 700. For example, the conduit 700 may extend into the fluid impermeable barrier 742 from the proximal end region 764 and may extend to the distal end region 762 to a point proximate to the reservoir 760 therein such that the inlet 704 is in fluid communication with the reservoir 760. The conduit 700 fluidly couples the chamber 746 with the fluid storage container (not shown) or the vacuum source (not shown).

The conduit 700 may extend through a bore in the assembly porous material 750. In an embodiment, the conduit 700 extends from the fluid outlet 748, through the bore, to a location that is proximate to the reservoir 760. In such an embodiment, the inlet 704 may not extend into the reservoir 760 and, instead, the inlet 704 may be disposed within the assembly porous material 750 (fluid permeable membrane 756 and/or fluid permeable support 758) or at a terminal end 766 thereof. For example, an end of the conduit 700 may be coextensive with or recessed within the fluid permeable membrane 756 and/or fluid permeable support 758. In an embodiment, the conduit 700 is at least partially disposed in the reservoir 760 and the inlet 704 may be extended into or be positioned in the reservoir 760. The bodily fluids collected in the fluid collection assembly 740 may be removed from the chamber 746 via the conduit 700.

Locating the inlet 704 at or near a location expected to be the gravimetrically low point of the chamber 746 when worn by a patient enables the conduit 700 to receive more of the bodily fluids than if inlet 704 was located elsewhere and reduce the likelihood of pooling (e.g., pooling of the bodily fluids may cause microbe growth and foul odors). For instance, the bodily fluids in the fluid permeable membrane 756 and the fluid permeable support 758 may flow in any direction due to capillary forces. However, the bodily fluids may exhibit a preference to flow in the direction of gravity, especially when at least a portion of the fluid permeable membrane 756 and/or the fluid permeable support 758 is saturated with the bodily fluids. Accordingly, one or more of the inlet 704 or the reservoir 760 may be located in the fluid collection assembly 740 in a position expected to be the gravimetrically low point in the fluid collection assembly 740 when worn by a patient, such as the distal end region 762.

As described in more detail below, the conduit 700 is configured to be coupled to, and at least partially extend between, one or more of the fluid storage container (not shown) and the vacuum source (not shown). In an example, the conduit 700 is configured to be directly connected to the vacuum source (not shown). In such an example, the conduit 700 may extend from the fluid impermeable barrier 742 by at least one foot, at least two feet, at least three feet, or at least six feet. In another example, the conduit 700 is configured to be indirectly connected to at least one of the fluid storage container (not shown) and the vacuum source (not shown). In some examples, the conduit is secured to a patient's skin with a catheter securement apparatus, such as a STATLOCK® catheter securement apparatus available from C. R. Bard, Inc., including but not limited to those disclosed in U.S. Pat. Nos. 6,117,163; 6,123,398; and 8,211, 063, the disclosures of which are all incorporated herein by reference in their entirety.

The inlet 704 and the outlet of the conduit 700 are configured to fluidly couple (e.g., directly or indirectly) the vacuum source (not shown) to the chamber 746 (e.g., the reservoir 760). As the vacuum source (FIG. 21) applies a vacuum/suction in the conduit 700, the bodily fluids in the chamber 746 (e.g., at the distal end region 762 such as in the reservoir 760) may be drawn into the inlet 704 and out of the fluid collection assembly 740 via the conduit 700. In some examples, the conduit may be frosted or opaque (e.g., black) to obscure visibility of the bodily fluids therein.

As previously discussed, the conduit 700 may be configured to be at least insertable into the chamber 746. In an example, the conduit 700 may be positioned in the chamber 746 such that a terminal end 720 of the conduit 700 is spaced from the fluid impermeable barrier 702 or other components of the fluid collection assembly 740 that may at least partially obstruct or block the inlet 704. Further, the inlet 704 of the conduit 700 may be offset relative to a terminal end 766 of the assembly porous material 750 such that the inlet 704 is closer to the proximal end region 764 of the fluid collection assembly 700 than the terminal end 766 of the assembly porous material 750. Offsetting the inlet 704 in such a manner relative to the terminal end 766 of the assembly porous material 750 allows the inlet 704 to receive bodily fluids directly from the assembly porous material 750 and, due to hydrogen bonding, pulls more bodily fluids from the assembly porous material 750.

The conduit 700 may include one or more markers (not shown) on an exterior thereof that are located to facilitate insertion of the conduit 700 into the chamber 746 and correct placement of the inlet 704 in the chamber 746. For example, the conduit 700 may include one or more markings thereon that are configured to prevent over or under insertion of the conduit 700, such as to prevent the fluid impermeable barrier 742 from obstructing or blocking the inlet 704. In another example, the conduit 700 may include one or more markings thereon that are configured to facilitate correct rotation of the conduit 700 relative to the chamber 746. The one or more markings may include a line, a dot, a sticker, or any other suitable marking.

Other embodiments of fluid impermeable barriers, fluid permeable membranes, fluid permeable supports, chambers, and their shapes and configurations are disclosed in U.S. patent application Ser. No. 15/612,325 filed on Jun. 2, 2017; U.S. patent application Ser. No. 15/260,103 filed on Sep. 8, 2016; and U.S. Pat. No. 10,390,989 filed on Sep. 8, 2016, the disclosure of each of which is incorporated herein, in its entirety, by this reference.

FIG. 8 is a cross-sectional schematic of a portion of a fluid collection system 822, according to an embodiment. The fluid collection system 822 includes a fluid collection assembly 840 and a conduit 800 in fluid communication with the fluid collection assembly 840. Except as otherwise disclosed herein, the conduit 800 is the same or substantially similar to any of the conduits disclosed herein. For example, the conduit 800 includes at least one wall 802 that defines an inlet 804, an outlet (not shown), and a passageway 808. The conduit 800 includes at least one conduit porous material 810 disposed in the passageway 808. Except as otherwise disclosed herein, the fluid collection assembly 840 is the same or substantially the same any the fluid collection assemblies disclosed herein. For example, the fluid collection assembly 840 includes a fluid impermeable barrier 842 that defines at least one opening 844, a chamber 846, and a fluid outlet 848. The fluid collection assembly 840 also include at least one assembly porous material 850 disposed in the chamber 846.

The fluid outlet 848 is formed at or near the distal end region 862 of the fluid collection assembly 840 instead or at or near the proximal end region (not shown). For example, the fluid outlet 848 may be formed at or near the reservoir (not shown) when the chamber 846 includes a reservoir 860 and/or at or near the expected gravimetrical low point of the fluid collection assembly 840. As such, the distance that the conduit 800 needs to extend within the chamber 846 for the inlet 804 to be at or near the reservoir 860 and/or the gravimetric low point of the chamber 846 is significantly decreased than if the fluid outlet 848 was formed at or near the proximal end region. In some examples, the assembly porous material 850 may be formed without a bore formed therein or the distance that the bore extends through the assembly porous material 850 may be decreased compared to the bore formed in the assembly porous material 850 illustrated in FIG. 7B which may increase the volume of bodily fluids that may be held within the assembly porous material 850. The conduit 800 may be disposed through the fluid outlet 848 such that the inlet 804 of the conduit 800 is adjacent to or within the assembly porous material 850.

The flexibility of the conduit 800 may allow the fluid outlet 848 to be located at or near the distal end region 862 of the fluid collection assembly 840. For example, the conduit 800 extending outwardly from the fluid outlet 848 may need to be bent at or near the fluid outlet 848 when the patient is wearing clothing or the patient is lying down. Similar bends formed in conventional hollow conduits are likely to kinky when similarly required to bend or may press into the clothing or bed.

FIG. 9 is a cross-sectional schematic of a portion of a fluid collection system 922, according to an embodiment. The fluid collection system 922 includes a fluid collection assembly 940 and a conduit 900 in fluid communication with the fluid collection assembly 940. Except as otherwise disclosed herein, the conduit 900 is the same or substantially similar to any of the conduits disclosed herein. Except as otherwise disclosed herein, the fluid collection assembly 940 is the same or substantially the same any the fluid collection assemblies disclosed herein. For example, the fluid collection assembly 940 includes a fluid impermeable barrier 942 that defines at least one opening 944, a chamber 946, and a fluid inlet 948. The fluid inlet 948 may be formed at or near the distal end region 962 (as shown) or on another portion of the fluid collection assembly 940. The fluid collection assembly 940 also include at least one assembly porous material 950 disposed in the chamber 946.

In an embodiment, at least a portion of the walls 902 of the conduit 900 are integrally formed with the fluid impermeable barrier 942 of the fluid collection assembly 940. Integrally forming the walls 902 with the fluid impermeable barrier 942 may decrease the complexity of forming the fluid collection system 922 since the fluid collection assembly 922 includes fewer parts to assembly. Integrally forming the walls 902 with the fluid impermeable barrier 942 may also make aligning and correctly positioning the conduit 900 relative to the fluid collection assembly 940 easier. In an embodiment, not shown, the conduit 900 is distinct from the fluid impermeable barrier 942 and is attached to the fluid impermeable barrier 942.

In an embodiment, the conduit 900 extends along at least a portion of the fluid impermeable barrier 942 which precludes the need to form a bore within the assembly porous material 950. In an embodiment, the fluid impermeable barrier 942 forms at least a portion (e.g., all) of the wall 902 of the conduit 900 and defines at least a portion of the passageway 908. In such an embodiment, the conduit 900 may be defined by at least one inner wall 902*a* and at least one outer wall 902*b*. At least one of the inner wall 902*a* or the outer wall 902*b* are formed by the fluid impermeable barrier 942. In an example, one of the inner or outer wall 902*a*, 902*b* are distinct from the fluid impermeable barrier 942. In such an example, the inner or outer wall 902*a*, 902*b* are is distinct from the fluid impermeable barrier 942 may be formed from at least one fluid impermeable layer that is attached to the fluid impermeable barrier 942. In an embodiment, the conduit 900 extend away from the rest of the fluid impermeable barrier 942.

In an embodiment, the porous material 950 occupies substantially all of the chamber 946 such that that chamber 946 does not define a reservoir.

FIG. 10 is a cross-sectional schematic of a portion of a fluid collection system 1022 that includes a conduit 1000 in fluid communication with a fluid collection assembly 1040, according to an embodiment. Except as otherwise disclosed herein, the conduit 1000 is the same or substantially similar to any of the conduits disclosed herein. For example, the conduit 1000 may include at least one wall 1002 that define at least an inlet 1004, an outlet (not shown), and a passageway 1008. The conduit 1000 also includes a conduit porous material 1010 disposed in the passageway 1008. Except as otherwise disclosed herein, the fluid collection assembly 1040 is the same or substantially similar to any of the fluid collection assemblies disclosed herein. For example, the fluid collection assembly 1040 may include a fluid impermeable barrier 1042 defining an opening 1044, a chamber 1046, and a fluid outlet 1048. The fluid collection assembly 1040 may also include at least one assembly porous material 1050 disposed in the chamber 1046.

The conduit porous material 1010 and at least a portion of the assembly porous material 1050 are integrally formed together (e.g., exhibit single piece construction). Integrally forming the conduit porous material 1010 and the assembly porous material 1050 together may prevent gaps from forming between the conduit porous material 1010 and the assembly porous material 1050 which may inhibit flow of the bodily fluids from the assembly porous material 1050 to the conduit porous material 1010.

Figures 11, 12, 13, 14:
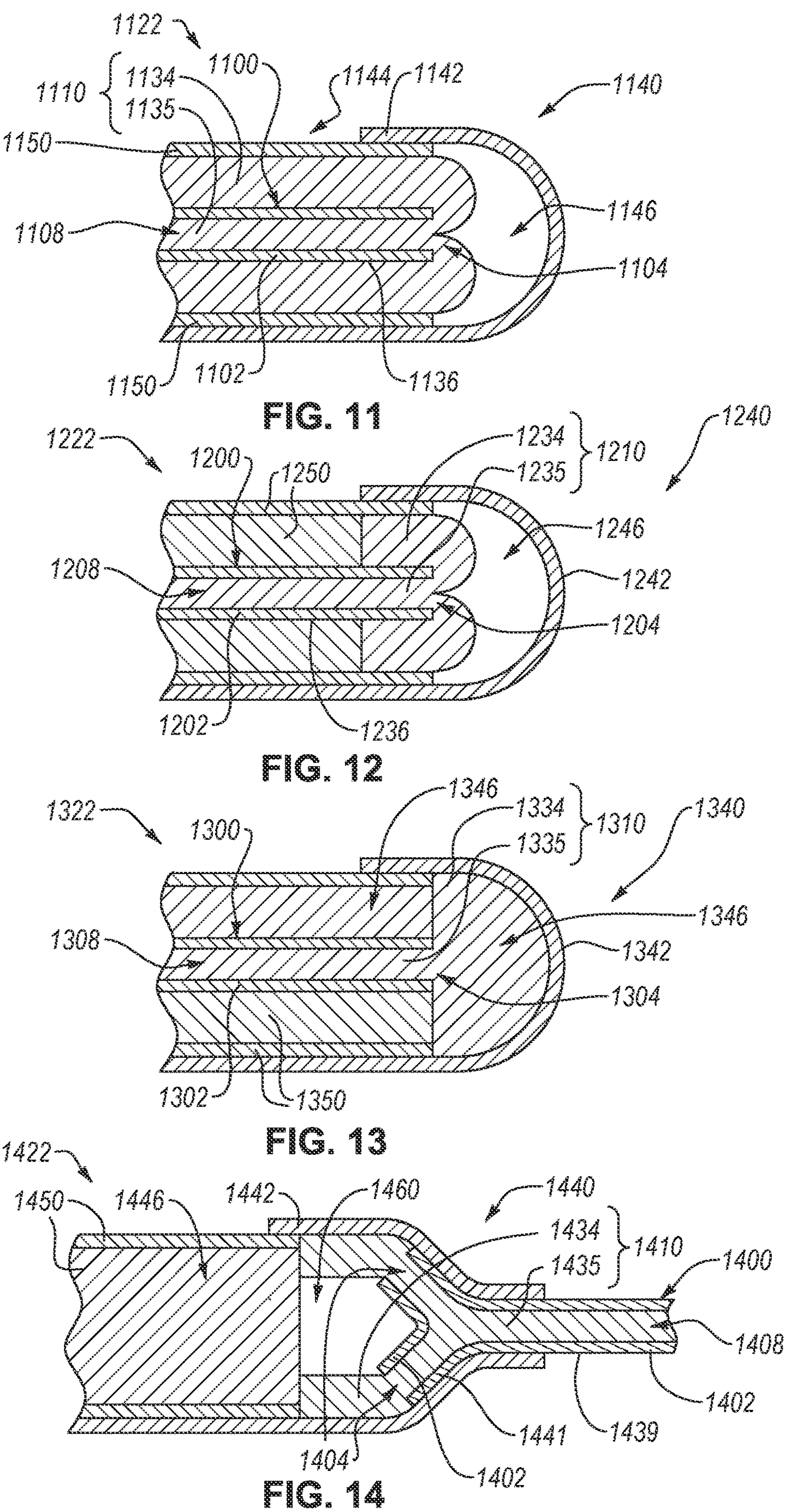
FIG. 11 is a cross-sectional schematic of a portion of a fluid collection system that includes a conduit in fluid communication with a fluid collection assembly, according to an embodiment.
FIG. 12 is a cross-sectional schematic of a portion of a fluid collection system that includes a conduit in fluid communication with a fluid collection assembly, according to an embodiment.
FIG. 13 is a cross-sectional schematic of a portion of a fluid collection system that includes a conduit in fluid communication with a fluid collection assembly, according to an embodiment.
FIG. 14 is a cross-sectional schematic of a portion of a fluid collection system that includes a conduit in fluid communication with a fluid collection assembly, according to an embodiment.

The fluid collection assemblies disclosed herein may include conduits having the conduit porous material thereof extending outwardly from the walls thereof. For example, FIG. 11 is a cross-sectional schematic of a portion of a fluid collection system 1122 that includes a conduit 1100 in fluid communication with a fluid collection assembly 1140, according to an embodiment. Except as otherwise disclosed herein, the conduit 1100 is the same or substantially similar to any of the conduits disclosed herein. For example, the conduit 1100 may include at least one wall 1102 that defines at least an inlet 1104, an outlet (not shown), and a passageway 1108. The conduit 1100 also includes a conduit porous material 1110 partially disposed in the passageway 1108. Except as otherwise disclosed herein, the fluid collection assembly 1140 is the same or substantially similar to any of the fluid collection assemblies disclosed herein. For example, the fluid collection assembly 1140 may include a fluid impermeable barrier 1142 defining a chamber 1146 and at least one assembly porous material disposed in the chamber 1146.

The conduit porous material 1110 may include a first portion 1134 extending outwardly from the passageway 1108 (e.g., from the inlet 1104) and a second portion 1135 disposed in the passageway 1108. The first portion 1134 may be folded back onto the walls 1102 of the conduit 1100. For example, the first portion 1134 may be folded back to cover all or substantially all of the outer surface 1136 of the walls 1104. When the fluid collection assembly 1140 includes the assembly porous material 1150, the first portion 1134 may support the assembly porous material 1150. The assembly porous material 1150 and the first portion 1134 of the conduit porous material 1110 may contact each other to minimize the formation of gaps therebetween.

During operation, the fluid collection assembly 1150 may receive bodily fluids into the chamber 1146 through the opening 1144. The bodily fluids may be received into the assembly porous material 1150 and flow into the first portion 1134 of the conduit porous material 1110. The bodily fluids may then flow into the second portion 1135 from the first portion 1134 where the vacuum pressure applied to the conduit 1100 suctions the bodily fluids through the conduit 1100. The hydrogen bonding between the water molecules of the bodily fluids causes the bodily fluids that are being suctioned through the second portion 1135 of the conduit porous material 1110 to pull additional bodily fluids from the first portion 1134 into the second portion 1135. Further, the hydrogen bonding causes the bodily fluids that are being pulled into the second portion 1135 to pull the bodily fluids into the first portion 1134 of the conduit porous material 1110 from the assembly porous material 1150. It is noted that any gaps between the assembly porous material 1150 and the first portion 1134 may break the hydrogen bonding between the water molecules in the assembly porous material 1150 and the first portion 1134. The lack of hydrogen bonding may prevent the pulling of the bodily fluids from the assembly porous material 1150 into the conduit porous material 1110. Instead, the bodily fluids flowing from the assembly porous material 1150 to the conduit porous material 1110 may, rely on wicking and gravity which may be slower. The hydrogen bonding between the water molecules and the direct contact between the conduit porous material 1110 and the assembly porous material 1150 decreases the need to position the inlet 1104 of the conduit 1100 at or near the expected gravimetric low point of the chamber 1146. The first portion 1134 may also facilitate alignment of the conduit 1100 in the chamber 1146.

FIG. 12 is a cross-sectional schematic of a portion of a fluid collection system 1222 that includes a conduit 1200 in fluid communication with a fluid collection assembly 1240, according to an embodiment. Except as otherwise disclosed herein, the conduit 1200 is the same or substantially similar to any of the conduits disclosed herein. For example, the conduit 1200 may include at least one wall 1202 that defines at least an inlet 1204, an outlet (not shown), and a passageway 1208. The conduit 1200 also includes a conduit porous material 1210 partially disposed in the passageway 1208. Except as otherwise disclosed herein, the fluid collection assembly 1240 is the same or substantially similar to any of the fluid collection assemblies disclosed herein. For example, the fluid collection assembly 1240 may include a fluid impermeable barrier 1242 and at least one assembly porous material 1250.

The conduit porous material 1210 may include a first portion 1234 extending outwardly from the passageway 1208 and a second portion 1235 disposed in the passageway 1208. The first portion 1234 may be folded back onto the walls 1202 of the conduit 1200. For example, the first portion 1234 may be folded back to cover only a portion of the outer surface 1236 of the walls 1202. The assembly porous material 1250 may define a cutout or be otherwise configured to accommodate and abut the first portion of 1234 to allow bodily fluids to be pulled from the assembly porous material 1250 to the first portion 1234 responsive to the bodily fluids being pulled from the first portion 1234 into the second portion 1235. The hydrogen bonding between the water molecules and the direct contact between the conduit porous material 1210 and the assembly porous material 1250 decreases the need to position the inlet 1204 of the conduit 1200 at or near the expected gravimetric low point of the chamber 1246. The first portion 1234 may also facilitate alignment of the conduit 1200 in the chamber 1246.

FIG. 13 is a cross-sectional schematic of a portion of a fluid collection system 1322 that includes a conduit 1300 in fluid communication with a fluid collection assembly 1340, according to an embodiment. Except as otherwise disclosed herein, the conduit 1300 is the same or substantially similar to any of the conduits disclosed herein. For example, the conduit 1300 may include at least one wall 1302 that defines at least an inlet 1304, an outlet (not shown), and a passageway 1308. The conduit 1300 also includes a conduit porous material 1310 partially disposed in the passageway 1308. Except as otherwise disclosed herein, the fluid collection assembly 1340 is the same or substantially similar to any of the fluid collection assemblies disclosed herein. For example, the fluid collection assembly 1340 may include a fluid impermeable barrier 1342 defining a chamber 1346 and at least one assembly porous material 1350 disposed in the chamber 1346.

The conduit porous material 1310 includes a first portion 1334 extending from the inlet 1304 and a second portion 1335 disposed in the passageway 1308. The first portion 1334 exhibits a shape that is configured to at least partially or substantially completely occupy a portion of the chamber 1346 that is not occupied by the assembly porous material 1350 and the rest of the conduit 1300. In other words, the first portion 1334 may prevent the chamber 1346 from forming a reservoir or may inhibit the volume of the reservoir.

The first portion 1334 may facilitate the flow of the bodily fluids from the assembly porous material 1350 and into the passageway 1308 of the conduit 1300. For example, as previously discussed, the hydrogen bonding between water molecules may pull the bodily fluids from the assembly porous material 1350, into the first portion 1334 of the conduit porous material 1350, and into the second portion 1335 of the conduit porous material 1350. When the chamber 1346 defines a reservoir, at least some of the bodily fluids may enter the reservoir. The bodily fluids may not be removed from the reservoir until the quantity of bodily fluids in the reservoir is sufficient for the bodily fluids to reach the inlet 1304 of the conduit 1300. As such, the presence of the reservoir may inhibit removal of substantially all of the bodily fluids from the chamber 1346 in a quick manner though, it is noted, the reservoir may increase the quantity of bodily fluids stored in the chamber 1346. Further, at least substantially occupying the portions of the chamber 1346 that do not include the assembly porous material 1350 with the conduit 1300 inhibits twisting and/or collapse of such portions of the chamber 1346 during use of the fluid collection assembly 1340. The hydrogen bonding between the water molecules, the direct contact between the conduit porous material 1310 and the assembly porous material 1350, and the decreased volume of any unoccupied portions of the chamber 1346 decreases the need to position the inlet 1304 of the conduit 1300 at or near the expected gravimetric low point of the chamber 1346. The first portion 1334 may also facilitate alignment of the conduit 1300 in the chamber 1346.

FIG. 14 is a cross-sectional schematic of a portion of a fluid collection system 1422 that includes a conduit 1400 in fluid communication with a fluid collection assembly 1440, according to an embodiment. Except as otherwise disclosed herein, the conduit 1400 is the same or substantially similar to any of the conduits disclosed herein. For example, the conduit 1400 may include at least one wall 1402 that defines at least an inlet 1404, an outlet (not shown), and a passageway 1408. The conduit 1400 also includes a conduit porous material 1410 partially disposed in the passageway 1408. Except as otherwise disclosed herein, the fluid collection assembly 1440 is the same or substantially similar to any of the fluid collection assemblies disclosed herein. For example, the fluid collection assembly 1440 may include a fluid impermeable barrier 1442 defining a chamber 1446 and at least one assembly porous material 1450 disposed in the chamber 1446.

The conduit 1400 is substantially similar to the conduit 600 illustrated in FIG. 6B. For example, the first portion 1434 of the conduit porous material 1410 may include a plurality of distinct regions that form different paths through which the bodily fluids may flow. The walls 1402 may also include a primary branch 1439 and one or more secondary branches 1441 extending therefrom. The plurality of regions of the first portion 1434 allows the conduit 1400 to remove bodily fluids from a plurality of different regions of the chamber 1446. It also may inhibit pooling of the bodily fluids in unoccupied portions of the chamber 1446. The hydrogen bonding between the water molecules and the direct contact between the conduit porous material 1410 and the assembly porous material 1450 decreases the need to position the inlet 1404 of the conduit 1400 at or near the expected gravimetric low point of the chamber 1446. The plurality of regions may also facilitate alignment of the conduit 1400 in the chamber 1446.

In an embodiment, as illustrated, the chamber 1446 includes a reservoir 1460. The reservoir 1460 may include the substantially unoccupied between the plurality of regions of the first portion 1434 of the conduit porous material 1410. However, the plurality of regions facilitates the removal of the bodily fluids from the reservoir 1460 since the plurality of regions of the first portion 1434 inhibits pooling. In an embodiment, the assembly porous material 1450 at least partially occupies the space between the plurality of regions of the first portion 1434 to further inhibit pooling of the bodily fluids in such unoccupied space.

Figure 15A:
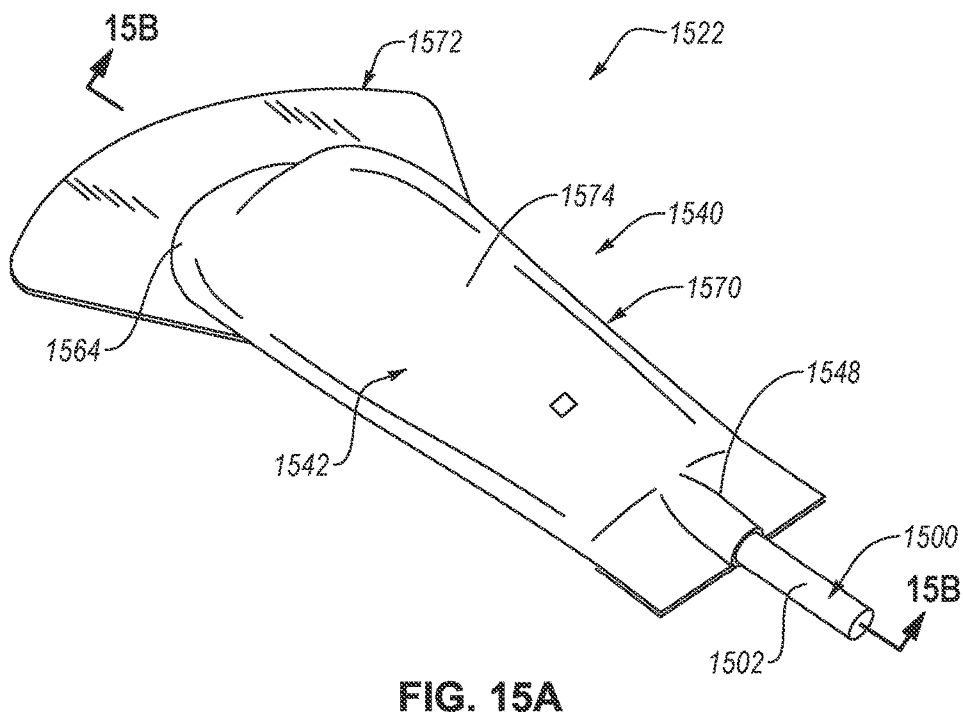
FIG. 15A is an isometric view of a portion of a fluid collection system that includes a conduit in fluid communication with a fluid collection assembly, according to an embodiment.
Figure 15B:
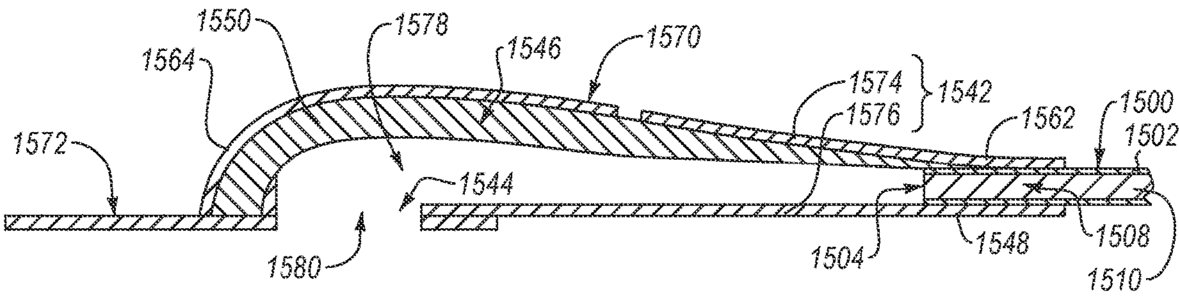
FIG. 15B is a cross-sectional schematic of the fluid collection assembly taken along plane 15B-15B shown in FIG. 15A, according to an embodiment.

The conduits disclosed herein may be included in fluid collection systems that include a male fluid collection assembly that is configured to receive bodily fluids from a male (e.g., from a penis). For example, FIG. 15A is an isometric view of a portion of a fluid collection system 1522 that includes a conduit 1500 in fluid communication with a fluid collection assembly 1540, according to an embodiment. FIG. 15B is a cross-sectional schematic of the fluid collection assembly 1540 taken along plane 15B-15B shown in FIG. 15A, according to an embodiment. The fluid collection assembly 1540 is an example of a male fluid collection assembly though, in some embodiments, the fluid collection assembly 1540 may be used to receive bodily fluids from a female urethral opening. Except as otherwise disclosed herein, the conduit 1500 is the same or substantially similar to any of the conduits disclosed herein. For example, the conduit 1500 may include at least one wall 1502 that define at least an inlet 1504, an outlet (not shown), and a passageway 1508. The conduit 1500 also includes a conduit porous material 1510 disposed in the passageway 1508. Except as otherwise disclosed herein, the fluid collection assembly 1540 is the same or substantially similar to any of the fluid collection assemblies disclosed herein. For example, the fluid collection assembly 1540 may include a fluid impermeable barrier 1542 defining an opening 1544, a chamber 1546, and a fluid outlet 1548. The fluid collection assembly 1540 may also include at least one assembly porous material 1550 disposed in the chamber 1546.

The fluid collection assembly 1540 includes a sheath 1570 and a base 1572. The base 1572 is configured to be attached (e.g., permanently attached to or configured to be permanently attached) to the sheath 1570. The base 1572 is also configured to be attached to the region about the urethral opening (e.g., penis) of the patient.

The sheath 1570 includes the fluid impermeable barrier 1542 that is at least partially formed from a first panel 1574 and a second panel 1576. The first panel 1574 and the second panel 1576 may be attached or integrally formed together (e.g., exhibits single piece construction). In an embodiment, as illustrated, the first panel 1574 and the second panel 1576 are distinct sheets. The fluid impermeable barrier 1542 also defines a chamber 1546 between the first panel 1574 and the second panel 1576, an opening 1544 at a proximal end region 1564 of the sheath 1570, and an fluid outlet 1548 at a distal end region 1562 of the sheath 1570. The sheath 1570 also includes at least one assembly porous material 1550 disposed in the chamber 1546.

The inner surface(s) of the fluid impermeable barrier 1542 (e.g., inner surfaces of the first and second panels 1574, 1576 at least partially defines the chamber 1546 within the fluid collection assembly 1540. The fluid impermeable barrier 1542 temporarily stores the bodily fluids in the chamber 1546. The fluid impermeable barrier 1542 may be formed from any of the fluid impermeable materials disclosed herein. As such, the fluid impermeable barrier 1542 substantially prevents the bodily fluids from passing through the fluid impermeable barrier 1542.

In an embodiment, at least one of the first panel 1574 or the second panel 1576 is formed from an at least partially transparent fluid impermeable material, such as polyethylene, polypropylene, polycarbonate, or polyvinyl chloride. Forming at least one of the first panel 1574 or the second panel 1576 from an at least partially transparent fluid impermeable material allows a person (e.g., medical practitioner) to examiner the penis. In some embodiments, both the first panel 1574 and the second panel 1576 are formed from at least partially transparent fluid impermeable material. Selecting at least one of the first panel 1574 or the second panel 1576 to be formed from an at least partially transparent impermeable material allows the penis to be examined without detaching the entire fluid collection assembly 1540 from the region about the penis. For example, the chamber 1546 may include a penis receiving area 1578 that is configured to receive the penis of the individual when the penis extends into the chamber 1546. The penis receiving area 1578 may be defined by at least the assembly porous material 1550 and at least a portion of the at least partially transparent material of the first panel 1574 and/or the second panel 1576. In other words, the assembly porous material 1550 is positioned in the chamber 1546 such that the assembly porous material 1550 is not positioned between the penis and at least a portion of the transparent portion of the first panel 1574 and/or second panel 1576 when the penis is inserted into the chamber 1546 through the opening 1544. The assembly porous material 1550 is generally not transparent and, thus, the portion of the at least partially transparent material of the first panel 1574 and/or the second panel 1576 that defines the penis receiving area 1578 forms a window which allows the person to view into the penis receiving area 1578 and examine the penis.

The opening 1544 defined by the fluid impermeable barrier 1542 provides an ingress route for fluids to enter the chamber 1546 when the penis is a buried penis and allow the penis to enter the chamber 1546 (e.g., the penis receiving area 1578) when the penis is not buried. The opening 1544 may be defined by the fluid impermeable barrier 1542 (e.g., an inner edge of the fluid impermeable barrier 1542). For example, the opening 1544 is formed in and extends through the fluid impermeable barrier 1542 thereby enabling bodily fluids to enter the chamber 1546 from outside of the fluid collection assembly 1540.

The fluid impermeable barrier 1542 defines the fluid outlet 1548 sized to receive the conduit 1500. The conduit 1500 may be at least partially disposed in the chamber 1546 or otherwise in fluid communication with the chamber 1546 through the fluid outlet 1548. The fluid outlet 1548 may be sized and shaped to form an at least substantially fluid tight seal against the conduit 1500 thereby substantially preventing the bodily fluids from escaping the chamber 1546. In an embodiment, the fluid outlet 1548 may be formed from a portion of the first panel 1574 and the second panel 1576 that are not attached or integrally formed together. In such an embodiment, the fluid impermeable barrier 1542 may not include a cap exhibiting a rigidity that is greater than the portions of the fluid impermeable barrier 1542 thereabout which may facilitate manufacturing of the fluid collection assembly 1540 may decreasing the number of parts that are used to form the fluid collection assembly 1540 and may decrease the time required to manufacture the fluid collection assembly 1540. The lack of the cap may make securing the conduit 1500 to the fluid outlet 1548 using interference fit to be difficult though, it is noted, attaching the conduit 1500 to the fluid outlet 1548 may still be possible. As such, the conduit 1500 may be attached to the fluid outlet 1548 (e.g., to the first and second panels 1574, 1576) using an adhesive, a weld, or otherwise bonding the fluid outlet 1548 to the fluid outlet 1548. Attaching the conduit 1500 to the fluid outlet 1548 may prevent leaks and may prevent the conduit 1500 from inadvertently becoming detached from the fluid outlet 1548. In an example, the conduit 1500 may be attached to the fluid outlet 1548 in the same manufacturing step that attaches the first and second panels 1574, 1576 together.

As previously discussed, the sheath 1570 includes at least one assembly porous material 1550 disclosed in the chamber 1546. The assembly porous material 1550 may direct the bodily fluids to one or more selected regions of the chamber 1546, such as away from the penis and towards the fluid outlet 1548. The assembly porous material 1550 may be formed from any of the porous materials disclosed herein. In an example, the assembly porous material 1550 may be formed from a single layer, two layers (e.g., a fluid permeable membrane extending across the opening 1544 and a fluid permeable support since the fluid permeable membrane may be formed from a relatively foldable, flimsy, or otherwise easily deformable material), or three or more layers. In an example, the assembly porous material 1550 may be formed from a nonwoven material or a woven material (e.g., spun nylon fibers). In an example, the assembly porous material 1550 may include at least one material exhibiting substantially no absorption or at least one absorbent or adsorbent material.

In an embodiment, the assembly porous material 1550 may be a sheet. Forming the assembly porous material 1550 as a sheet may facilitate the manufacturing of the fluid collection assembly 1540. For example, forming the assembly porous material 1550 as a sheet allows the first panel 1574, the second panel 1576, and the assembly porous material 1550 to each be sheets. During the manufacturing of the fluid collection assembly 1540, the first panel 1574, the second panel 1576, and the assembly porous material 1550 may be stacked and then attached to each other in the same manufacturing step. For instance, the assembly porous material 1550 may exhibit a shape that is the same size or, more preferably, slightly smaller than the size of the first panel 1574 and the second panel 1576. As such, attaching the first panel 1574 and the second panel 1576 together along the outer edges thereof may also attach the assembly porous material 1550 to the first panel 1574 and the second panel 1576. The assembly porous material 1550 may be slightly smaller than the first panel 1574 and the second panel 1576 such that the first panel 1574 and/or the second panel 1576 extend around the assembly porous material 1550 such that the assembly porous material 1550 does not form a passageway through the fluid impermeable barrier 1542 through which the bodily fluids may leak. Also, attaching the assembly porous material 1550 to the first panel 1574 and/or the second panel 1576 may prevent the assembly porous material 1550 from significantly moving in the chamber 1546, such as preventing the assembly porous material 1550 from bunching together near the fluid outlet 1548. In an example, the assembly porous material 1550 may be attached to the first panel 1574 or the second panel 1576 (e.g., via an adhesive) before or after attaching the first panel 1574 to the second panel 1576. In an example, the assembly porous material 1550 may merely be disposed in the chamber 1546 without attaching the assembly porous material 1550 to at least one of the first panel 1574 or the second panel 1576. In an embodiment, the assembly porous material 1550 may exhibit shapes other than a sheet, such as a hollow generally cylindrical shape.

Generally, the sheath 1570 is substantially flat when the penis is not in the penis receiving area 1578 and the sheath 1570 is resting on a flat surface. The sheath 1570 is substantially flat because the fluid impermeable barrier 1542 is formed from the first panel 1574 and the second panel 1576 instead of a generally tubular fluid impermeable barrier. Further, as previously discussed, the assembly porous material 1550 may be a sheet, which also causes the sheath 1570 to be substantially flat. The sheath 1570 may also be substantially flat because the fluid collection assembly 1540 may not include relatively rigid rings or caps that exhibit a rigidity that is greater than the portions of the fluid impermeable barrier 1542 thereabout since such rings and caps may inhibit the sheath 1570 being substantially flat. It is noted that the sheath 1570 is described as being substantially flat because at least one of the assembly porous material 1550 may cause a slight bulge to form in the sheath 1570 depending on the thickness of the assembly porous material 1550, the fluid outlet 1548 and/or conduit 1500 may cause a bulge thereabout, or the base 1572 may pull on portions of the sheath 1570 thereabout. It is also noted that the sheath 1570 may also be compliant and, as such, the sheath 1570 may not be substantially flat during use since, during use, the sheath 1570 may rest on a non-flat surface (e.g., may rest on the testicles, the perineum, and/or between the thighs) and the sheath 1570 may conform to the surface of these shapes.

The ability of the sheath 1570 to be substantially flat when the penis is not in the penis receiving area 1578 and the sheath 1570 is resting on a flat surface allows the fluid collection assembly 1540 to be used with a buried and a non-buried penis. For example, when the fluid collection assembly 1540 is being used with a buried penis, the penis does not extend into the penis receiving area 1578 which causes the sheath 1570 to lie relatively flat across the aperture 1580 of the base 1572. When the sheath 1570 lies relatively flat across the aperture 1580, the assembly porous material 1550 extends across the opening 1544 and the aperture 1580 and is in close proximity to the buried penis. As such, the assembly porous material 1550 prevents or inhibits pooling of bodily fluids discharged from the buried penis against the skin of the individual since the assembly porous material 1550 will receive and remove at least a significant portion of the bodily fluids that would otherwise pool against the skin of the individual. Thus, the skin of the individual remains dry thereby improving comfort of using the fluid collection assembly 1540 and preventing skin degradation. However, unlike other conventional fluid collection assemblies that are configured to be used with buried penises, the fluid collection assembly 1540 may still be used with a non-buried penis since the non-buried penis can still be received into the penis receiving area 1578, even when the penis is fully erect. Additionally, the ability of the sheath 1570 to be substantially flat allows the fluid collection assembly 1540 to be used more discretely than if the sheath 1570 was not substantially flat thereby avoiding possibly embarrassing scenarios.

When the sheath 1570 is substantially flat, the assembly porous material 1550 occupies substantially all of the chamber 1546 and the penis receiving area 1578 is collapsed (shown as being non-collapsed in FIG. 15B for illustrative purposes to show the penis receiving area 1578). In other words, the sheath 1570 may not define a region that is constantly unoccupied by the assembly porous material 1550. When the assembly porous material 1550 occupies substantially all of the chamber 1546, the bodily fluids discharged into the chamber 1546 are unlikely to pool for significant periods of time since pooling of the bodily fluids may cause sanitation issues, cause an odor, and/or may cause the skin of the individual to remain in contact with the bodily fluids which may cause discomfort and skin degradation.

As previously discussed, the first panel 1574, the second panel 1576, and the assembly porous material 1550 may be selected to be relatively flexible. The first panel 1574, the second panel 1576, and the assembly porous material 1550 are relatively flexible when the first panel 1574, the second panel 1576, and the assembly porous material 1550, respectively, are unable to maintain their shape when unsupported. The flexibility of the first panel 1574, the second panel 1576, and the assembly porous material 1550 may allow the sheath 1570 to be substantially flat, as discussed above. The flexibility of the first panel 1574, the second panel 1576, and the assembly porous material 1550 may also allow the sheath 1570 to conform to the shape of the penis even when the size and shape of the penis changes (e.g., becomes erect) and to minimize any unoccupied spaces in the chamber 1546 in which bodily fluids may pool.

As previously discussed, the fluid collection assembly 1540 includes a base 1572 that is configured to be attached to the sheath 1570. For example, the base 1572 is configured to be permanently attached to the sheath 1570. The base 1572 is configured to be permanently attached to the sheath 1570 when, for example, when the fluid collection assembly 1540 is provided with the base 1572 permanently attached to the sheath 1570 or the base 1572 is provided without being permanently attached to the sheath 1570 but is configured to be permanently attached to the sheath 1570 at some point in the future. Permanently attached means that the sheath 1570 cannot be detached from the base 1572 without damaging at least one of the sheath 1570 or the base 1572, using a blade to separate the sheath 1570 from the base 1572, and/or using chemicals to dissolve the adhesive that attaches the sheath 1570 from the base 1572. The base 1572 may be permanently attached to the sheath 1570 using an adhesive, sewing, heat sealing, RF welding, or US welding. In an embodiment, the base 1572 is configured to be reversibly attached to the sheath 1570. In an embodiment, the base 1572 is integrally formed with the sheath 1570.

As previously discussed, the base 1572 includes an aperture 1580. The base 1572 is permanently attached to the first end region 120 of the sheath 1570 such that the aperture 1580 is aligned with the opening 1544.

The base 1572 is sized, shaped, and made of a material to be coupled to the skin that surrounds the penis (e.g., mons pubis, thighs, testicles, and/or perineum) and have the penis disposed therethrough. For example, the base 1572 may define an aperture 1580 configured to have the penis positioned therethrough. In an example, the base 1572 may exhibit the general shape or contours of the skin surface that the base 1572 is configured to be coupled with. The base 1572 may be flexible, thereby allowing the base 1572 to conform to any shape of the skin surface and mitigate the base 1572 pulling the on skin surface. The base 1572 may extend laterally past the sheath 1570 thereby increasing the surface area of the skin of the individual to which the fluid collection assembly 1540 may be attached compared to a substantially similar fluid collection assembly 1540 that did not include a base.

Figure 17:
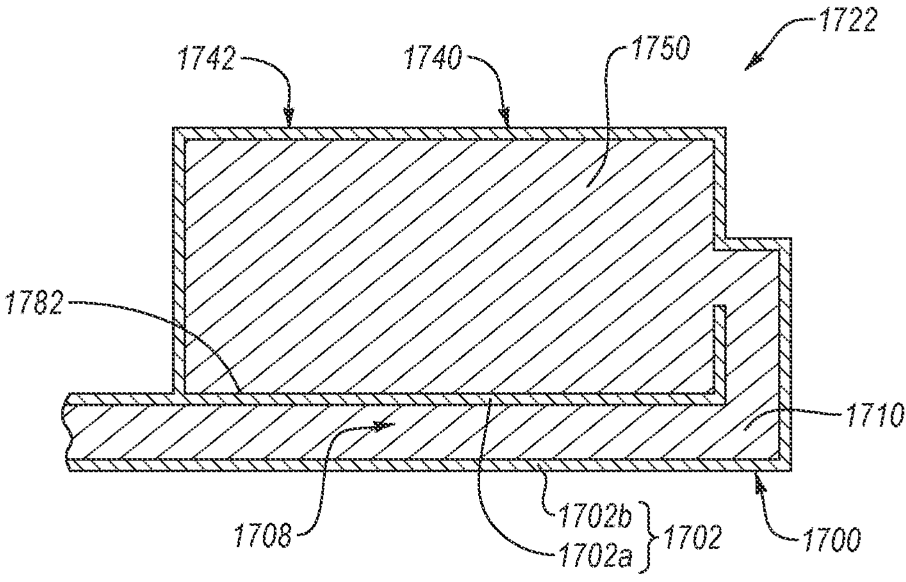
FIG. 17 is a cross-sectional schematic of a portion of a fluid collection system that includes a conduit in fluid communication with a fluid collection assembly, according to an embodiment.

As previously discussed, the fluid collection assembly 1540 includes the conduit 1500. The conduit 1500 may be the same or substantially similar to any of the conduits disclosed herein. For example, the conduit 1500 includes a conduit porous material 1510 disposed in the passageway 1508. The conduit porous material 1510 may be distinct from the assembly porous material 1550 (as shown) or may be integrally formed with the assembly porous material 1550 (as shown in FIGS. 10 and 17).

The inlet 1504 of the conduit 1500 may be located near the distal end region 1562 of the sheath 1570 which is expected to be the gravimetrically low point of the chamber 1546 when worn by a patient. Locating the inlet 1504 at or near the distal end region 1562 of the sheath 1570 enables the conduit 1500 to receive more of the bodily fluids than if the inlet of the conduit 1500 was located elsewhere and reduce the likelihood of pooling (e.g., polling of the bodily fluids may cause microbe growth and foul odors).

Figure 16:
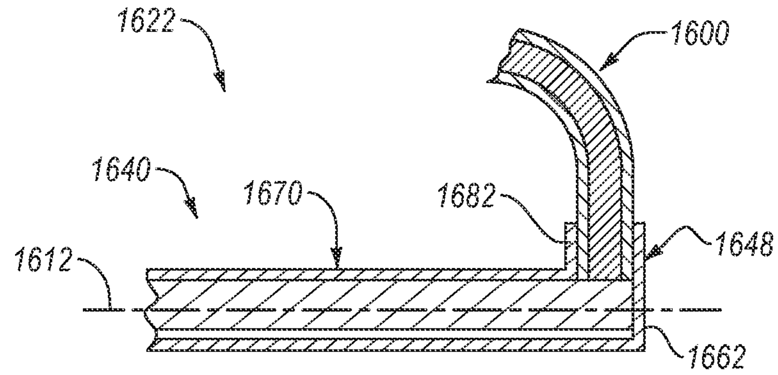
FIG. 16 is a cross-sectional schematic of a portion of a fluid collection system that includes a conduit in fluid communication with a fluid collection assembly, according to an embodiment.

The conduit 150 is illustrated as extending from the distal end region 1562 of the sheath 1570 in a direction that is generally parallel to a longitudinal axis of the sheath 1570 when the sheath 1570 is lying on a flat surface. However, due to the flexibility of the conduit 1500, the conduit 1500 may extend from the distal end region 1562 at an angle that is not generally parallel to the longitudinal axis of the sheath 1570. For example, FIG. 16 is a cross-sectional schematic of a portion of a fluid collection system 1622 that includes a conduit 1600 in fluid communication with a fluid collection assembly 1640, according to an embodiment. Except as otherwise disclosed herein, the conduit 1600 and the fluid collection assembly 1640 are the same or substantially similar to any of the conduits and fluid collection assemblies disclosed herein, respectively. The fluid collection assembly 1640 includes a sheath 1670 defining a fluid outlet 1648 at or near the distal end region 1662 of the sheath 1670. The fluid outlet 1648 is configured to allow the conduit 1600 to extend from the sheath 1670 at a direction that is not parallel to (e.g., perpendicular or oblique) relative to a longitudinal axis 1612 of the sheath 1670 when the sheath 1670 is lying on a flat surface. For example, the fluid outlet 1648 may include at least one wall 1682 that are configured to abut the conduit 1600. The wall 1682 may extend from the rest of the sheath 1670 in a direction that is not parallel to the longitudinal axis 1612 of the sheath 1670 thereby causing the conduit 1600 to extend from the sheath 1670 in a similar direction. The conduit 1600 may extend from the sheath 1670 in a direction that is not parallel to the longitudinal axis of the sheath 1670 since the conduit 1600 is able to be bent for the reasons previously disclosed herein.

The fluid impermeable barriers of the male fluid collection assemblies disclosed herein may form at least a portion of the wall (e.g., define at least a portion of the passageway) of the conduit attached thereto. For example, FIG. 17 is a cross-sectional schematic of a portion of a fluid collection system 1722 that includes a conduit 1700 in fluid communication with a fluid collection assembly 1740, according to an embodiment. Except as otherwise disclosed herein, the conduit 1700 and the fluid collection assembly 1740 are the same as or substantially similar to any of the conduits and fluid collection assemblies, respectively, disclosed herein. It is noted that FIGS. 15B to 16 are side cross-sectional schematics of at least a portion of a fluid collection system whereas FIG. 17 is a top cross-sectional schematic of a portion of the fluid collection system 1722.

Similar to the fluid collection system 922 illustrated in FIG. 9, the conduit 1700 extends along at least a portion of the fluid impermeable barrier 1742. The conduit 1700 may extend along a lateral side 1784 of the fluid collection assembly 1740 to prevent the weight of the conduit 1700 from resting on the penis of the patient which may increase patient discomfort. In an embodiment, not shown, the conduit 1700 is distinct from the fluid impermeable barrier 842 and is attached to the fluid impermeable barrier 1742. In an embodiment, the fluid impermeable barrier 1742 forms at least a portion (e.g., all) of the wall 1702 of the conduit 1700 and defines at least a portion of the passageway 1708. In such an embodiment, the conduit 1700 may be defined by at least one inner wall 1702*a* and at least one outer wall 1702*b*. In an example, one of the inner or outer wall 1702*a*, 1702*b* are distinct from the fluid impermeable barrier 1742. In such an example, the inner or outer wall 1702*a*, 1702*b* that is distinct from the fluid impermeable barrier 1742 may be formed from at least one fluid impermeable layer that is attached to the fluid impermeable barrier 1742.

Similar to the fluid collection system 1022 illustrated in FIG. 10, the conduit porous material 1710 and at least a portion of the assembly porous material 1750 are integrally formed together (e.g., exhibit single piece construction). For example, the conduit porous material 1710 and at least a portion of the assembly porous material 1750 may be formed from the same sheet with a cut or portion removed therefrom to allow for a portion of the walls 1702 and/or fluid impermeable barrier 1742 to be formed between a portion of the conduit porous material 1710 and the assembly porous material 1750.

Figure 18:
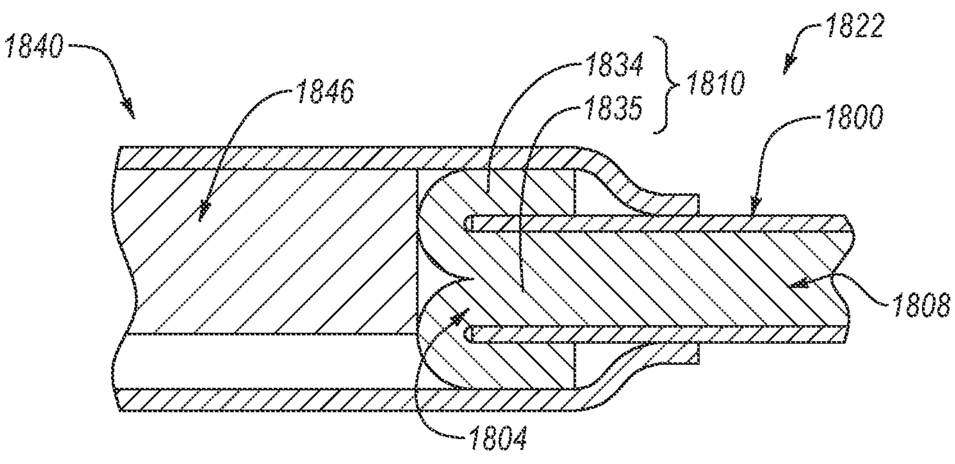
FIG. 18 is a cross-sectional schematic of a portion of a fluid collection system that includes a conduit in fluid communication with a fluid collection assembly, according to an embodiment.

The male fluid collection assemblies disclosed herein may be used with conduits including a porous of the conduit porous material extending from the inlets thereof. For example, FIG. 18 is a cross-sectional schematic of a portion of a fluid collection system 1822 that includes a conduit 1800 in fluid communication with a fluid collection assembly 1840, according to an embodiment. Except as otherwise disclosed herein, the conduit 1800 and the fluid collection assembly 1840 are the same or substantially similar to any of the conduits and fluid collection assemblies disclosed herein, respectively. The conduit 1800 includes a conduit porous material 1810 including a first portion 1834 and a second portion 1835. At least a portion of the first portion 1834 extends outwardly from the passageway 1808 (e.g., from the inlet 1804) and at least a portion of the second portion 1835 is disposed in the passageway 1808. In an embodiment, the first portion 1834 may be folded back which, as previously discussed, may inhibit collapse of the conduit 1800 at or near the inlet 1804. The conduit porous material 1810 may abut the assembly porous material 1850 to facilitate pulling the bodily fluids from the assembly porous material 1850 to the conduit porous material 1810 via hydrogen bonding. The conduit porous material 1810 may inhibit twisting and/or collapse of the chamber 1846, facilitate alignment of the conduit 1800, and, as previously discussed, may decrease the need to have the inlet 1804 of the conduit 1800 positioned at or near the expected gravimetric low point of the chamber 1846.

Figure 19:
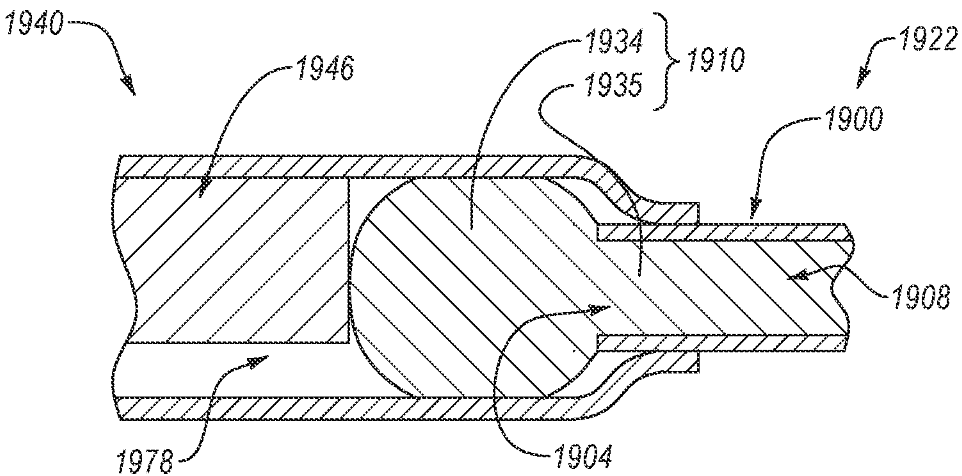
FIG. 19 is a cross-sectional schematic of a portion of a fluid collection system that includes a conduit in fluid communication with a fluid collection assembly, according to an embodiment.

FIG. 19 is a cross-sectional schematic of a portion of a fluid collection system 1922 that includes a conduit 1900 in fluid communication with a fluid collection assembly 1940, according to an embodiment. Except as otherwise disclosed herein, the conduit 1900 and the fluid collection assembly 1940 are the same or substantially similar to any of the conduits and fluid collection assemblies disclosed herein, respectively. The conduit 1900 includes a conduit porous material 1910 including a first portion 1934 and a second portion 1935. At least a portion of the first portion 1934 extends outwardly from the passageway 1908 and at least a portion of the second portion 1935 is disposed in the passageway 1908. The first portion 1934 may be configured to substantially occupy portions of the chamber 1946 near the inlet 1904 of the conduit 1900. For example, the first portion 1934 may be configure to exhibit substantially occupy the portions of the chamber 1946 that are not occupied by the assembly porous material 1950 or form part of the penis receiving area 1978. The conduit porous material 1910 may inhibit twisting and/or collapse of the chamber 1946, facilitate alignment of the conduit 1900, and, as previously discussed, may decrease the need to have the inlet 1904 of the conduit 1900 positioned at or near the expected gravimetric low point of the chamber 1946.

Figure 20:
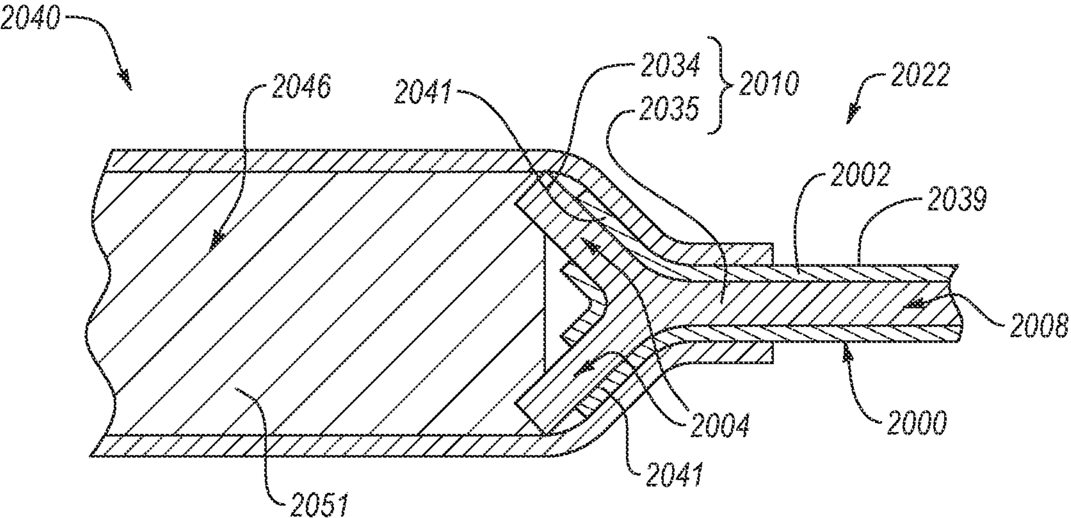
FIG. 20 is a cross-sectional schematic of a portion of a fluid collection system that includes a conduit in fluid communication with a fluid collection assembly, according to an embodiment.

FIG. 20 is a cross-sectional schematic of a portion of a fluid collection system 2022 that includes a conduit 2000 in fluid communication with a fluid collection assembly 2040, according to an embodiment. Except as otherwise disclosed herein, the conduit 2000 and the fluid collection assembly 2040 are the same or substantially similar to any of the conduits and fluid collection assemblies disclosed herein, respectively. The conduit 2000 includes a conduit porous material 2010 including a first portion 2034 and a second portion 2035. At least a portion of the first portion 2034 extends outwardly from the passageway 2008 and at least a portion of the second portion 2035 is disposed in the passageway 2008. The first portion 2034 may include a plurality of regions. The walls 2002 of the conduit 2000 may also include a primary branch 2039 and one or more secondary branches 2041 extending from the primary branch 2039. The plurality of regions 2034 may allow the conduit 2000 to receive bodily fluids from a plurality of different locations of the chamber 2046. In an embodiment, the plurality of regions 2034 may extend sufficiently into the chamber 2046 such that the plurality or regions enclose the sides of any penis disposed in the chamber 2046. In such an embodiment, the plurality of regions 2034 increases the likelihood that bodily fluids discharged from the penis are directly received by the conduit porous material 2010 which may allow the assembly porous material 2050 to be omitted from the fluid collection assembly 2040. The conduit porous material 2010 may inhibit twisting and/or collapse of the chamber 2046, facilitate alignment of the conduit 2000, and, as previously discussed, may decrease the need to have the inlet 2004 of the conduit 2000 positioned at or near the expected gravimetric low point of the chamber 2046.

The conduits disclosed herein may be used with fluid collection assemblies other than the fluid collection assemblies illustrated in FIG. 7A-20. For example, the conduits disclosed herein may be used with a Foley catheter, a condom-style male catheter, or wound dressing. Other examples of fluid collection assemblies that the conduits disclosed herein may be attached to are disclosed in U.S. patent application Ser. No. 16/433,773 filed on Jun. 6, 2019, the disclosure of which is incorporated herein, in its entirety, by this reference. It is also noted that at least some of the fluid collection assemblies may be used for wound care to receive one or more bodily fluids (e.g., blood, etc.) from a wound.

Figure 21:
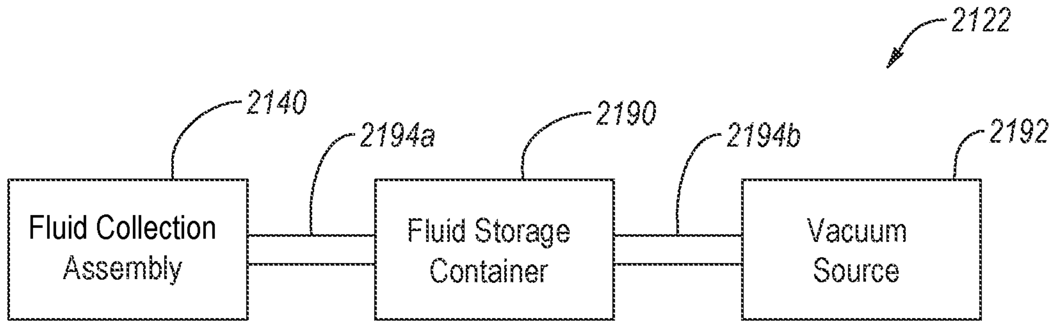
FIG. 21 is a block diagram of a fluid collection system for fluid collection, according to an embodiment.

FIG. 21 is a block diagram of a fluid collection system 2122 for fluid collection, according to an embodiment. The system 2122 includes a fluid collection assembly 2140, a fluid storage container 2190, and a vacuum source 2192. The fluid collection assembly 2140, the fluid storage container 2190, and the vacuum source 2192 may be fluidly coupled to each other via one or more conduits. For example, as illustrated, the conduits may include a first conduit **2194*a* extending from the fluid collection assembly 2140 to the fluid storage container 2190 and a second conduit 2194*b* extending from the fluid storage container 2190 to the vacuum source 2192**.

In an embodiment, the first conduit **2194*a* includes at least one conduit porous material. In an example, the conduit porous material may be disposed in all of the first conduit 2194*a* (e.g., extends from or near the inlet of the first conduit 2194*a* to or near the outlet of the first conduit 2194*a*). In an example, the conduit porous material may be disposed in only a portion of the first conduit 2194*a*. In an embodiment, the second conduit 2194*b* includes at least one conduit porous material. Similar to the first conduit 2194*a*, the conduit porous material of the second conduit 2194*b* may be disposed in all of the second conduit 2194*b* or only a portion of the second conduit 2194*b*. In an embodiment, one of the first or second conduit 2194*a*, 2194*b*** may include a hollow conduit.

In an embodiment, the fluid collection system 2122 may include at least one hollow conduit (not shown) in addition to the first conduit **2194*a* and/or the second conduit 2194*b*. In an example, the first conduit 2194*a* may be in direct fluid communication with the fluid collection assembly 2140 and may extend from the fluid collection assembly 2140 only part of the distance between the fluid collection assembly 2140 and the fluid storage container 2190. As such, the fluid collection system 2122 may include a hollow conduit that is connected to the outlet of the first conduit 2194***a* and extends from the first conduit 2194*a* to the fluid storage container 2190.

The fluid collection assembly 2140 may be similar or identical to any of the fluid collection assemblies disclosed herein in one or more aspects. The fluid collection assembly 2140 may be shaped and sized to be positioned adjacent to a female urethral opening or have a male urethral opening positioned therethrough (e.g., receive a penis therein). For example, the fluid collection assembly 2140 may include a fluid impermeable barrier at least partially defining a chamber (e.g., interior region) of the fluid collection assembly 2140. The fluid impermeable barrier also defines at least one opening extending therethrough from the external environment. The opening may be positioned adjacent to a female urethral opening or have a male urethral opening positioned therethrough. The fluid collection assembly 2140 may include porous material disposed in the chamber such as one or more of a fluid permeable support and a fluid permeable membrane. The fluid collection assembly 2140 includes one or more of any of the securement bodies disclosed herein.

The fluid storage container 2190 is sized and shaped to retain the bodily fluids therein. The fluid storage container 2190 may include a bag (e.g., drainage bag), a bottle or cup (e.g., collection jar), or any other enclosed container for storing bodily fluids such as urine. In some examples, the first conduit 2194*a* may extend from the fluid collection assembly 2140 and attach to the fluid storage container 2190 at a first point therein. The second conduit 2194*b* may attach to the fluid storage container 2190 at a second point thereon and may extend and attach to the vacuum source 2192. Accordingly, a vacuum (e.g., suction) may be drawn through fluid collection assembly 2140 via the fluid storage container 2190. Fluid, such as urine, may be drained from the fluid collection assembly 2140 using the vacuum source 2192.

The vacuum source 2192 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 2192 may provide a vacuum or suction to remove fluid from the fluid collection assembly 2140. In some examples, the vacuum source 2192 may be powered by one or more of a power cord (e.g., connected to a power socket), one or more batteries, or even manual power (e.g., a hand operated vacuum pump). In some examples, the vacuum source 2192 may be sized and shaped to fit outside of, on, or within the fluid collection assembly 2140. For example, the vacuum source 2192 may include one or more miniaturized pumps or one or more micro pumps. The vacuum source 2192 may include one or more of a switch, a button, a plug, a remote, or any other device suitable to activate the vacuum source 2192.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean±10%, ±5%, or +2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

I claim:

1. A conduit for use in a fluid collection system for collecting one or more bodily fluids, the conduit comprising:
- at least one wall at least partially defining at least:
  - an inlet;
  - an outlet; and
  - a passageway extending from the inlet to the outlet; and
- at least one conduit porous material disposed in at least a portion of the passageway, the at least one conduit porous material occupying a cross-sectional area of the passageway and extending at least from or near the inlet to or near the outlet, the at least one conduit porous material defining at least one of a central gap in a center of the at least one conduit porous material or an outer gap between opposing edges of the at least one conduit porous material.

2. The conduit of claim 1, wherein the at least one wall includes polyvinyl chloride.

3. The conduit of claim 1, wherein the at least one wall is formed from a film.

4. The conduit of claim 1, wherein the at least one conduit porous material includes spun nylon.

5. The conduit of claim 1, wherein the at least one conduit porous material is only disposed in the passageway.

6. The conduit of claim 1, wherein the at least one conduit porous material includes a first portion and a second portion, at least a portion of the first portion is not disposed in the passageway and at least a portion of the second portion is disposed in the passageway.

7. The conduit of claim 6, wherein the first portion exhibits a generally semi-spherical shape or a bulb-like shape.

8. The conduit of claim 6, wherein the first portion exhibits a maximum lateral dimension that is greater than a maximum lateral dimension of the at least one wall.

9. The conduit of claim 6, wherein the first portion includes a plurality of regions that form different and distinct flow paths for the one or more bodily fluids to flow through.

10. The conduit of claim 9, wherein the at least one wall includes a primary branch and one or more secondary branches, the passageway of the primary branch including at least a portion of the second portion of the at least one conduit porous material disposed therein, the passageway of the one or more secondary branches including a portion of one or more regions of the first portion of the at least one conduit porous material disposed therein.

11. The conduit of claim 1, wherein at least a portion of the at least one conduit porous material includes a rolled sheet.

12. The conduit of claim 1, wherein at least a portion of the at least one conduit porous material exhibits a generally circular cross-sectional shape.

13. The conduit of claim 1, wherein the conduit may exhibit a bend therein exhibiting an average radius of curvature of about 2 cm without kinking.

14. A fluid collection system, comprising:
- a fluid collection assembly including:
  - a fluid impermeable barrier defining at least a chamber, at least one opening, and a fluid outlet;
  - at least one assembly porous material disposed in the chamber; and a conduit in fluid communication with the chamber, the conduit including:

at least one wall at least partially defining at least:

an inlet;

and outlet; and a passageway extending from the inlet to the outlet; and at least one conduit porous material distinct from the at least one assembly porous material, the at least one conduit porous material disposed in at least a portion of the passageway, the at least one conduit porous material occupying a cross-sectional area of the passageway and extending at least from or near the inlet to or near the outlet, the at least one conduit porous material defining at least one of a central gap in a center of the at least one conduit porous material or an outer gap between opposing edges of the at least one conduit porous material.

15. The fluid collection assembly of claim 14, wherein the fluid impermeable barrier defines a reservoir, the inlet of the conduit is positioned adjacent to the reservoir, and the conduit extends through the fluid outlet.

16. The fluid collection assembly of claim 15, wherein the fluid impermeable barrier includes a distal end region and a proximal end region opposite the distal end region, the reservoir is at least partially defined by the distal end region of the fluid impermeable barrier and the fluid outlet is at or near the distal end region of the fluid impermeable barrier.

17. The fluid collection assembly of claim 14, wherein the conduit occupies substantially all of the chamber that is not occupied by the at least one assembly porous material.

18. The fluid collection assembly of claim 14, wherein the fluid impermeable barrier defines a reservoir, the fluid impermeable barrier includes a distal end region and a proximal end region opposite the distal end region, the reservoir is at least partially defined by the distal end region of the fluid impermeable barrier and the fluid outlet is at the proximal end region of the fluid impermeable barrier.

19. The fluid collection assembly of claim 14, wherein the fluid impermeable barrier extends along a longitudinal axis and the conduit extends from the fluid outlet so that it is generally parallel to the longitudinal axis.

20. The fluid collection assembly of claim 14, wherein the fluid impermeable barrier extends along a longitudinal axis and the conduit extends from the fluid outlet at an angle that is generally non-parallel to the longitudinal axis.

21. The fluid collection assembly of claim 14, wherein the fluid impermeable barrier of the fluid collection assembly forms at least a portion of the at least one wall of the conduit.

22. The fluid collection assembly of claim 14, wherein the conduit extends along at least one lateral surface of the fluid impermeable barrier.

23. The fluid collection assembly of claim 14, further comprising an adaptor, the adaptor including a conduit portion attached to the inlet of the conduit.

* * * * *